US012649784B2

(12) United States Patent
Muschler

(10) Patent No.: US 12,649,784 B2
(45) Date of Patent: Jun. 9, 2026

(54) MONOCLONAL ANTIBODIES FOR INTRACELLULAR DELIVERY OF PAYLOADS

(71) Applicant: Oregon Health & Science University, Portland, OR (US)

(72) Inventor: John L. Muschler, Lake Oswego, OR (US)

(73) Assignee: Oregon Health & Science University, Portland, OR (US)

( * ) Notice: Subject to any disclaimer, the term of this patent is extended or adjusted under 35 U.S.C. 154(b) by 812 days.

(21) Appl. No.: 17/907,534

(22) PCT Filed: Mar. 30, 2021

(86) PCT No.: PCT/US2021/024974
§ 371 (c)(1),
(2) Date: Sep. 27, 2022

(87) PCT Pub. No.: WO2021/202592
PCT Pub. Date: Oct. 7, 2021

(65) Prior Publication Data
US 2023/0140976 A1      May 11, 2023

Related U.S. Application Data

(60) Provisional application No. 63/002,029, filed on Mar. 30, 2020.

(51) Int. Cl.
*C07K 16/28*          (2006.01)
*G01N 33/533*          (2006.01)

(52) U.S. Cl.
CPC .......... *C07K 16/28* (2013.01); *G01N 33/533* (2013.01); *C07K 2317/565* (2013.01); *C07K 2317/77* (2013.01)

(58) Field of Classification Search
None
See application file for complete search history.

(56) References Cited

U.S. PATENT DOCUMENTS 8,655,035 B2      2/2014  Malon et al.
2012/0034208 A1      2/2012  Chang
(Continued)

FOREIGN PATENT DOCUMENTS

WO      WO2017196819 A2      11/2017

OTHER PUBLICATIONS

UniProtKB entry A0AOM2VCV5_9GAMM, Dec. 11, 2019 [online]; Esterase, VT06_09565; entire document (3 pages). Retrieved on 23 Aug. 1, 2021 at uniprot.org/uniprot/A0AOM2VCV5.
(Continued)

*Primary Examiner* — Aurora M Fontainhas
(74) *Attorney, Agent, or Firm* — Tanya M. Harding; Lee & Hayes, P.C.

(57) ABSTRACT

The present disclosure relates to delivering payloads to the interior of a cell. In particular, the present disclosure provides three monoclonal antibodies that bind dystroglycan (DG) on the surface of cells. The antibodies are internalized into endocytic vesicles inside the cells once they are bound to DG. Thus, these antibodies can be used to selectively target and deliver payloads to cells, such as epithelial cells in cancer. The disclosed antibodies bind to DG independent of variable DG glycosylation. The targeted delivery enables selective treatment, imaging, and surveillance of cells in cancer, such as bladder cancer, along with other uses.

17 Claims, 13 Drawing Sheets
Specification includes a Sequence Listing.

(56)        References Cited

U.S. PATENT DOCUMENTS

| | | |
|---|---|---|
| 2013/0224210 A1 | 8/2013 | Adamkewicz et al. |
| 2015/0374845 A1 | 12/2015 | Muschler et al. |
| 2016/0046725 A1 | 2/2016 | Beau-Larvor et al. |
| 2017/0281766 A1 | 10/2017 | Wiltzius |
| 2019/0194309 A1 | 6/2019 | Lane et al. |
| 2019/0352420 A1 | 11/2019 | Hofmann et al. |
| 2020/0023076 A1 | 1/2020 | Fotin-Mleczek et al. |
| 2020/0062832 A1 | 2/2020 | Sun et al. |

OTHER PUBLICATIONS

Humphrey, et al., "A new monoclonal antibody DAG-6F4 against human alpha-dystroglycan reveals reduced core protein in some, but not all, dystroglycanopathy patients," Neuromuscular Disorders, vol. 25, 2015, pp. 32-42.

Khursheed & Bashyam, "Apico-basal polarity complex and cancer," Journal of Biosciences, vol. 39, No. 1, 2014, pp. 145-155.

Kowalski, et al."A Phase II Study of Oportuzumab Monatox: An Immunotoxin Therapy for Patients with Noninvasive Urothelial Carcinoma In Situ Previously Treated with Bacillus Calmette-Guérin," The Journal of Urology, vol. 188, 2012, pp. 1712-1718.

Pan, et al., "Endoscopic molecular imaging of human bladder cancer using a CD47 antibody," Science Translation Medicine, vol. 6, No. 260, 2014, 10 pgs.

Scott, et al., "Antibody therapy of cancer," Nature Reviews Cancer, vol. 12, 2012, pp. 278-287.

Akhavan, et al., "Loss of Cell-Surface Laminin Anchoring Promotes Tumor Growth and Is Associated with Poor Clinical Outcomes," Cancer Research, vol. 72, No. 10, 2012, pp. 2578-2588.

Hara, et al., "Like-acetylglucosaminyltransferase (LARGE)-dependent modification of dystroglycan at Thr-317/319 is required for laminin binding and arenavirus infection," PNAS, vol. 108, No. 42, 2011, pp. 17426-17431.

Inamori, et al., "Dystroglycan Function Requires Xylosyl- and Glucuronyltransferase Activities of LARGE," Science, vol. 335, 2012, pp. 93-96.

Kanagawa, et al., "Molecular Recognition by LARGE Is Essential for Expression of Functional Dystroglycan," Cell, vol. 117, 2004, pp. 953-964.

Leonoudakis, et al., "Endocytic trafficking of laminin is controlled by dystroglycan and is disrupted in cancers," Journal of Cell Science, vol. 127, 2014, pp. 4894-4903.

Meyer, et al., "A simplified workflow for monoclonal antibody sequencing," PLOS One, 2019, pp. 1-19.

Muschler, et al., "A Role for Dystroglycan in Epithelial Polarization: Loss of Function in Breast Tumor Cells," Cancer Research, vol. 62, 2002, pp. 7102-7109.

Ohsawa, et al., "Cell Extrusion: A Stress-Responsive Force for Good or Evil in Epithelial Homeostasis," Dev Cell, vol. 44, 2018, pp. 284-296.

Royer, et al., "Epithelial cell polarity: a major gatekeeper against cancer?," Cell Death and Differentiation, vol. 18, 2011, pp. 1470-1477.

Singh, et al., "Proteolytic Enzymes and Altered Glycosylation Modulate Dystroglycan Function in Carcinoma Cells," Cancer Research, vol. 64, 2004, pp. 6152-6159.

Wilson, "Apico-basal polarity in polycystic kidney disease epithelia," Biochimica et Biophysica Acta, vol. 1812, 2011, pp. 1239-1248.

MONOCLONAL ANTIBODIES FOR INTRACELLULAR DELIVERY OF PAYLOADS

CROSS-REFERENCE TO RELATED APPLICATIONS

This is the U.S. National Phase of PCT/US2021/024974, filed Mar. 30, 2021, which claims priority to and the benefit of the earlier filing date of U.S. Provisional Patent Application No. 63/002,029 filed on Mar. 30, 2020, which is incorporated herein by reference in its entirety as if fully set forth herein.

STATEMENT REGARDING FEDERALLY SPONSORED RESEARCH OR DEVELOPMENT

This invention was made with government support under TR002369 awarded by the National Institutes of Health. The government has certain rights in the invention.

STATEMENT REGARDING SEQUENCE LISTING

The Sequence Listing associated with this application is provided in text format in lieu of a paper copy and is hereby incorporated by reference into the specification. The name of the text file containing the Sequence Listing is 2GS2206.txt. The text file is 145 KB, was created on Mar. 30, 2021, and is being submitted electronically via EFS-Web.

FIELD OF THE DISCLOSURE

The present disclosure relates to delivering payloads to the interior of a cell. In particular, the present disclosure provides compositions and methods for targeted delivery of payloads using antibodies that bind to dystroglycan independent of variable dystroglycan glycosylation. The targeted delivery enables selective treatment and imaging of cells, along with other uses.

BACKGROUND OF THE DISCLOSURE

Cell polarity refers to the intrinsic asymmetry observed in cells, including their shape, structure, and/or organization of cellular components. Most epithelial cells, migrating cells, and developing cells possess cell polarity for their function.

Epithelial cells have apical-basal polarity, defined by an apical membrane facing the lumen of internal cavities or facing the outside surface of the body, and a basal membrane oriented at the opposite end from the lumen and contacting the extracellular matrix. Epithelial cells adhere to each other at the lateral membrane sides through specialized structures such as tight junctions, desmosomes, and adherence junctions. The junctions contribute to the apical-basal polarity by restricting apical and basolateral proteins to their corresponding membrane side. The apical-basal polarity of an epithelial cell is fundamental to its function, including regulating the directional transport of ions across cell sheets for barrier function as well as ensuring directionality for secretory and absorptive functions.

The loss of apical-basal polarity is implicated in a number of diseases, including polycystic kidney disease, retinitis pigmentosa, cystic fibrosis, interstitial cystitis, actinic keratosis, and a number of cancers, exemplified by bladder cancer (Wilson, *Biochimica et Biophysica Acta—Mol Basis Dis* 1812:1239-1248, 2011; Royer & Lu, *Cell Death Diff* 18, 1470-1477, 2011).

Bladder cancer is the fifth most common cancer in the US, accounting for 3% of cancer deaths. About 75,000 cases occur per year, and 75% of these cases present as noninvasive disease. Currently, poor detection and treatment options lead to high recurrence rates, high treatment costs, and poor patient outcomes. Because of the high recurrence, repeated monitoring and treatment, bladder cancers are the costliest of all cancers to treat per capita.

Bladder cancer can be diagnosed using a variety of tests and procedures, including: cystoscopy, a method using a small narrow tube to view the urethra and bladder; biopsy, a procedure involving collection of a cell sample during cystoscopy; urine cytology, a procedure involving examining a urine sample under the microscope, and imaging tests, including computerized tomography (CT), that allow visualization of the structures in the urinary tract. Current imaging techniques can miss small lesions in the bladder, and the upper tract of the bladder is not easily detected. Therefore, detection and monitoring of bladder cancer is costly and arduous, with a lifetime cost to treat per capita of $100 k to $200 k.

Current treatments for bladder cancer include surgery, chemotherapy in the bladder (intravesical chemotherapy), bladder removal and reconstruction, systemic chemotherapy, radiation therapy, immunotherapy, or a combination of two or more of these treatments.

Immunotherapy drugs harness a patient's immune system to attack the cancer. Immunotherapy treatments include: *Bacillus* Calmette-Guerin (BCG), a tuberculosis vaccine; interferon alfa-2b (Intron A), a synthetic version of interferon, a protein the immune system makes to help fight infections; and atezolizumab (TECENTRIQ®) for locally advanced or metastatic bladder cancer that does not respond to chemotherapy. Yet 30% of bladder cancer patients are BCG unresponsive, and bladder cancer has high rates (50-70%) of recurrence.

An antibody-drug conjugate, VB4-845 (Vicinium™) is currently being evaluated in clinical trials for treatment of patients with high-grade non-muscle invasive bladder cancer who are BCG-unresponsive. VB4-845 targets epithelial cell adhesion molecule (EpCAM) on the surface of tumor cells to deliver a toxin, *Pseudomonas* exotoxin A. However, the effectiveness of VB4-845 is dependent on EpCAM overexpression, which is evident on only a subset of bladder cancers and bladder cancer cells.

Two key unmet needs in bladder cancer management are: 1) the more effective detection, diagnosis, and monitoring of bladder cancers; and 2) the more effective treatment of non-invasive disease to limit recurrence and progression. Bladder cancer detection and treatment could be greatly enhanced by the development of reagents that can be selectively internalized by early stage bladder cancer lesions. These could take the form of affinity reagents such as immune-targeted contrast agents and therapeutics. Early stage bladder cancers are particularly amenable to affinity-based immunotherapies and immunodiagnostics because these reagents can be introduced into the bladder directly (known as "intravesicular" delivery) to target the cancer without the need for systemic exposure to these reagents. Therefore, a strong opportunity for improved bladder cancer treatment lies in the development of new intravesicular affinity reagents that are effective at selectively binding bladder cancer cells in vivo and internalizing imaging and/or therapeutic compounds.

The present disclosure provides compositions and methods for more effective diagnosis, monitoring, and treatment of pre-invasive bladder cancers. Beyond the realm of bladder cancer, the compositions and methods can provide detection and treatment of multiple diseases, operating through the targeted delivery of compounds to select cell populations in patients.

SUMMARY OF THE DISCLOSURE

The current disclosure provides antibodies and antigen-binding fragments thereof, compositions containing at least one such antibody or fragment, and methods to target a payload to the interior of a cell. The compositions and methods make use of antibodies that bind to dystroglycan (DG) on the surface of a cell and allow internalization of the antibodies into endocytic vesicles of the cell. The binding of antibodies to DG is independent of variable DG glycosylation.

Antibodies of the present disclosure include monoclonal antibodies produced by hybridoma DG1A1 (deposited as ATCC Patent Deposit No. PTA-126595 on Jan. 23, 2020), produced by hybridoma DGH6 (deposited as ATCC Patent Deposit No. PTA-126593 on Jan. 23, 2020), and produced by hybridoma DG4H4 (deposited as ATCC Patent Deposit No. PTA-126594 on Jan. 23, 2020), and antigen binding fragments thereof. Particular embodiments include an isolated antibody or antigen binding fragment thereof that binds to DG including: a heavy chain including CDRH1 shown in SEQ ID NO: 1, CDRH2 shown in SEQ ID NO: 2, and CDRH3 shown in SEQ ID NO: 3; and a light chain including CDRL1 shown in SEQ ID NO: 4, CDRL2 shown in SEQ ID NO: 5, and CDRL3 shown in SEQ ID NO: 6. Particular embodiments include an isolated antibody or antigen binding fragment thereof that binds to DG including: a heavy chain including CDRH1 shown in SEQ ID NO: 11, CDRH2 shown in SEQ ID NO: 12, and CDRH3 shown in SEQ ID NO: 13; and a light chain including CDRL1 shown in SEQ ID NO: 14, CDRL2 shown in SEQ ID NO: 15, and CDRL3 shown in SEQ ID NO: 16. Particular embodiments include an isolated antibody or antigen binding fragment thereof that binds to DG including: a heavy chain including CDRH1 shown in SEQ ID NO: 21, CDRH2 shown in SEQ ID NO: 22, and CDRH3 shown in SEQ ID NO: 23; and a light chain including CDRL1 shown in SEQ ID NO: 24, CDRL2 shown in SEQ ID NO: 25, and CDRL3 shown in SEQ ID NO: 26. Any of these antibodies and fragments thereof are also provided in compositions, including for instance therapeutic compositions.

In particular embodiments, the compositions include an isolated antibody which is produced by hybridoma DG1A11, or an antigen-binding fragment thereof, or an antibody or binding fragment thereof that binds competitively with the antibody that is produced by that hybridoma. In particular embodiments, the compositions include an isolated antibody which is produced by hybridoma DGH6, or an antigen-binding fragment thereof, or an antibody or binding fragment thereof that binds competitively with the antibody that is produced by that hybridoma. In particular embodiments, the compositions include an isolated antibody which is produced by hybridoma DG4H4, or antigen-binding fragment thereof, or an antibody or binding fragment thereof that binds competitively with the antibody that is produced by that hybridoma.

In particular embodiments, the compositions include an isolated antibody or antigen-binding fragment thereof including: a variable heavy (VH) domain set forth in SEQ ID NO: 7 and/or a variable light (VL) domain set forth in SEQ ID NO: 9. In particular embodiments, the compositions include an isolated antibody or antigen-binding fragment thereof including: a heavy chain set forth in SEQ ID NO: 8 and/or a light chain set forth in SEQ ID NO: 10. In particular embodiments, the compositions include an isolated antibody or antigen-binding fragment thereof including: a variable heavy (VH) domain set forth in SEQ ID NO: 17 and/or a variable light (VL) domain set forth in SEQ ID NO: 19. In particular embodiments, the compositions include an isolated antibody or antigen-binding fragment thereof including: a heavy chain set forth in SEQ ID NO: 18 and/or a light chain set forth in SEQ ID NO: 20. In particular embodiments, the compositions include an isolated antibody or antigen-binding fragment thereof including: a variable heavy (VH) domain set forth in SEQ ID NO: 27 and/or a variable light (VL) domain set forth in SEQ ID NO: 29. In particular embodiments, the compositions include an isolated antibody or antigen-binding fragment thereof including: a heavy chain set forth in SEQ ID NO: 28 and/or a light chain set forth in SEQ ID NO: 30.

In particular embodiments, the compositions include an isolated antibody or antigen-binding fragment thereof including: a heavy chain encoded by SEQ ID NOs: 31 and 32 and/or a light chain encoded by SEQ ID NOs: 33 and 34. In particular embodiments, the compositions include an isolated antibody or antigen-binding fragment thereof including: a heavy chain encoded by SEQ ID NOs: 35 and 36 and/or a light chain encoded by SEQ ID NOs: 37 and 38. In particular embodiments, the compositions include an isolated antibody or antigen-binding fragment thereof including: a heavy chain encoded by SEQ ID NOs: 39 and 40 and/or a light chain encoded by SEQ ID NOs: 41 and 42.

Particular embodiments of the present disclosure provide a composition including an antibody or antigen-binding fragment thereof described herein attached to (or to which is attached) a payload. In particular embodiments, the payload is directly attached or indirectly attached to the antibody or antigen-binding fragment thereof. In particular embodiments, the payload is internalized by a cell. In particular embodiments, the payload includes a detectable agent or a biologically functional (e.g., therapeutic) molecule. In particular embodiments, the detectable agent includes a fluorescent tag, a bioluminescent tag, a chemiluminescent tag, a radioisotope, a magnetic resonance imaging contrast agent, and/or a nanoparticle. In particular embodiments, the biologically functional molecule includes a therapeutic agent. In particular embodiments, the biologically functional molecule includes a radioisotope, a toxin, a nanoparticle, a nanoparticle including a nucleic acid, a nucleic acid, and/or a small molecule drug.

In particular embodiments, the antibodies or antigen-binding fragments thereof bind to DG on the surface of living cells and are internalized into the cells. In particular embodiments, the antibodies or antigen-binding fragments thereof are internalized into endocytic vesicles. In particular embodiments, the endocytic vesicles include late endosomes and lysosomes.

Particular embodiments include using the antibodies or antigen-binding fragments thereof of the disclosure to target a therapeutic payload to a cell expressing DG. In particular embodiments, cells expressing DG include a non-epithelial cell, an epithelial cell, a non-polarized cell, a polarized cell, and/or a cell that has lost apical-basal polarity.

Particular embodiments include using the antibodies or antigen-binding fragments thereof of the disclosure to target a therapeutic payload to a cell to treat a disorder associated with loss of apical-basal polarity in epithelial cells. In particular embodiments, the antibodies or antigen-binding fragments thereof can be used to assess the efficacy of a treatment for a disorder associated with loss of apical-basal polarity in epithelial cells. In particular embodiments, the disorder associated with loss of apical-basal polarity in epithelial cells is bladder cancer. In particular embodiments, the bladder cancer is early stage bladder cancer. In particular embodiments, the antibodies or antigen-binding fragments thereof can provide detection and/or treatment of multiple diseases, operating through the targeted delivery of compounds to select cell populations in patients.

Particular embodiments include using the antibodies or antigen-binding fragments thereof of the disclosure to diagnose and/or monitor a disorder associated with loss of apical-basal polarity in epithelial cells. In particular embodiments, the disorder associated with loss of apical-basal polarity in epithelial cells is bladder cancer. In particular embodiments, the bladder cancer is early stage bladder cancer.

Particular embodiments include using the antibodies or antigen-binding fragments thereof of the disclosure to target a detectable agent to a cell to measure or detect DG protein level ex vivo and in vivo.

Particular embodiments include using the antibodies or antigen-binding fragments thereof of the disclosure to identify a cell as lacking apical-basal polarity and to identify test compounds that promote apical-basal polarity.

BRIEF DESCRIPTION OF THE DRAWINGS

One or more of the drawings submitted herein are better understood in color, which is not available in patent application publications at the time of filing. Applicant considers the color versions of the drawings as part of the original submission and reserve the right to present color images of the drawings in later proceedings.

(FIG. 8A) Immunofluorescence imaging of the antibody from hybridoma DG1A11 on UMUC5 cells from FIG. 7. Enlarged region (FIG. 8B) shows internalization of the antibody into endocytic vesicles that populate the cytoplasm but are excluded from the nucleus. (FIG. 8C) DAPI staining of nuclei of the cells.

Figures 10A, 10B, 10C:
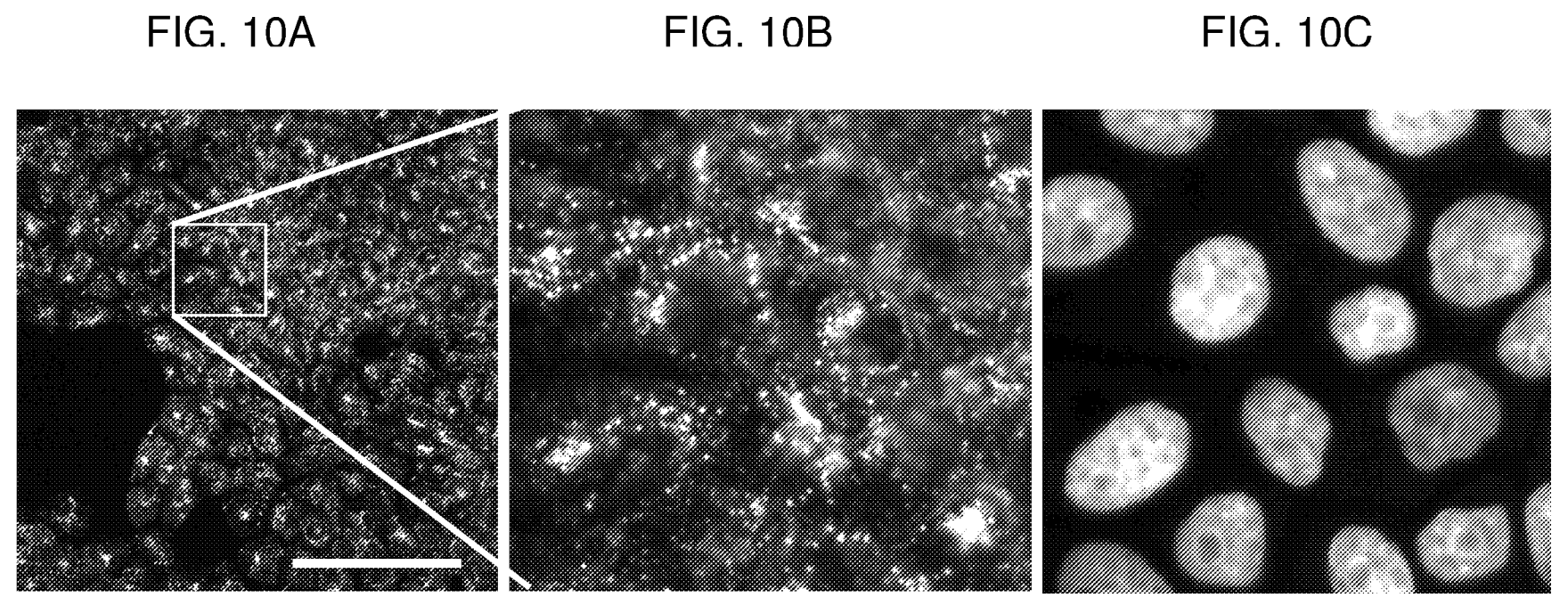

FIGS. 10A-10C. Immunofluorescence imaging of an antibody from hybridoma DG4H4 on live cells. (FIG. 10A) Immunofluorescence imaging of the antibody from hybridoma DG4H4 on UMUC5 cells from FIG. 9. Enlarged region (FIG. 10B) shows internalization of the antibody into endocytic vesicles that populate the cytoplasm but are excluded from the nucleus. (FIG. 10C) DAPI staining of nuclei of the cells.

FIGS. 11A-11C. Immunofluorescence imaging of binding and internalization of an antibody from hybridoma DG1A11 in live Jurkat cells. (FIG. 11A) Immunofluorescence imaging using a negative control monoclonal antibody followed by an Alexa-568-conjugated anti-mouse secondary antibody. (FIG. 11B) Immunofluorescence imaging using a monoclonal antibody from hybridoma DG1A11 followed by an Alexa-568-conjugated anti-mouse secondary antibody. (FIG. 11C) Immunofluorescence imaging using a monoclonal antibody from hybridoma DG1A11 followed by an Alexa-568-conjugated anti-mouse secondary antibody, followed by trypsin treatment. The cells were treated with a monoclonal antibody from hybridoma DG1A11 for 40 min, followed by incubation with an Alexa-568-conjugated anti-mouse secondary antibody for 6 hours, followed by treatment with trypsin for 20 min at 37° C. Treatment with trypsin in live cells removes all surface-bound antibodies.

(FIG. 12A) Immunofluorescence image from FIG. 11C. (FIG. 12B) Enlarged region shows internalization of the antibody into endocytic vesicles. The observed foci are endocytic vesicles.

FIGS. 13A, 13B. Immunofluorescence imaging of binding and internalization of an antibody from hybridoma DG4H4 in live Jurkat cells. (FIG. 13A) Immunofluorescence imaging using a monoclonal antibody from hybridoma DG4H4 followed by an Alexa-568-conjugated anti-mouse secondary antibody, followed by trypsin treatment. The cells were treated with a monoclonal antibody from hybridoma DG4H4 for 40 min, followed by incubation with an Alexa-568-conjugated anti-mouse secondary antibody for 6 hours, followed by treatment with trypsin for 20 min at 37° C. (FIG. 13B) Enlarged region shows internalization of the antibody into endocytic vesicles. The observed foci are endocytic vesicles.

SEQUENCE LISTING

Figure 1:
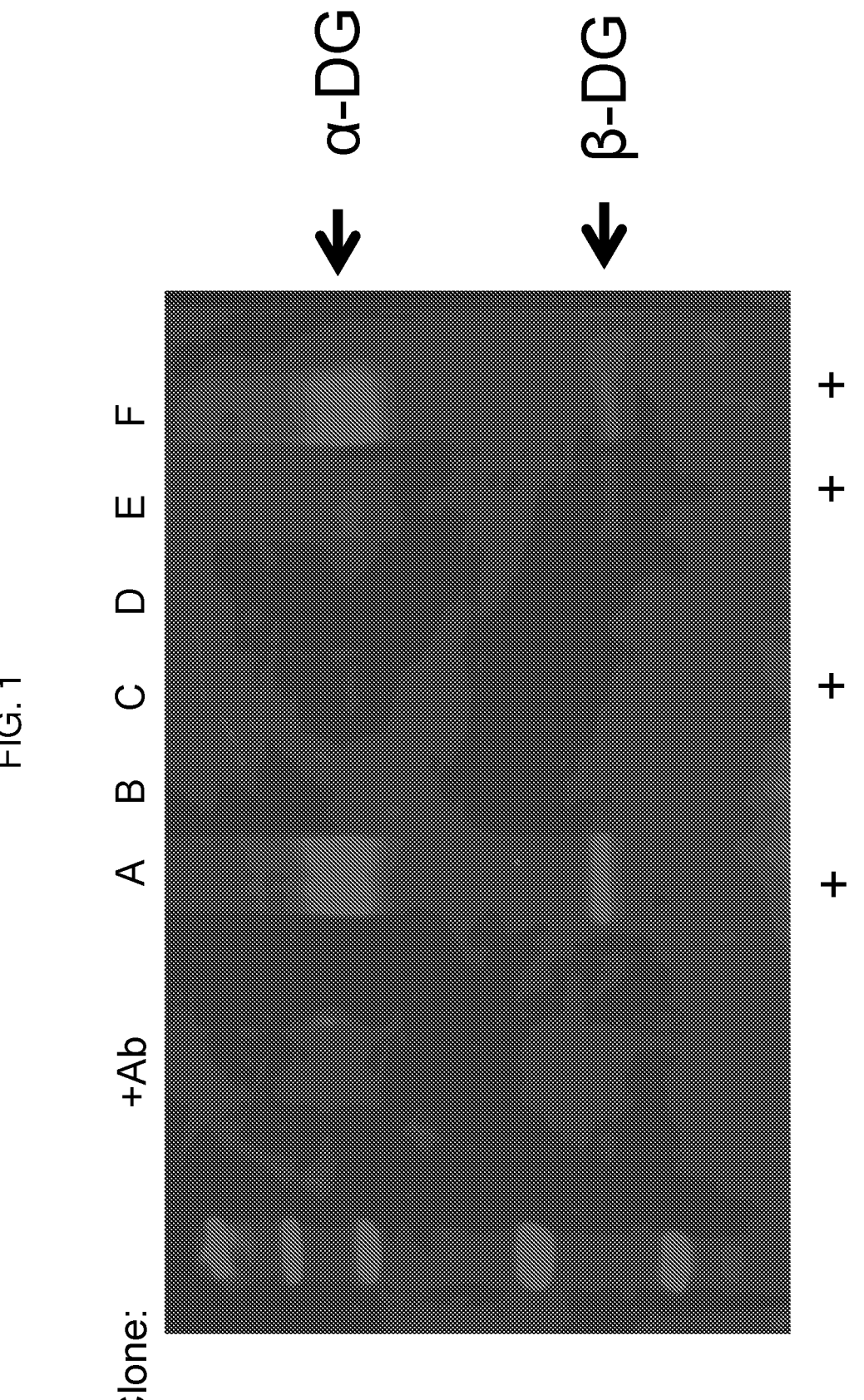
FIG. 1. Immunoprecipitation assays of antibodies from hybridomas DG1A11 (lane A), DGH6 (lane E), and DG4H4 (lane F) with dystroglycan (DG) heterodimer. The "+" indicates that the antibodies were positive by an immunofluorescence screen.

The nucleic acid and amino acid sequences provided herein and/or provided in the accompanying Sequence Listing are shown using letter abbreviations for nucleotide bases and amino acid residues, as defined in 37 C.F.R. § 1.822 and set forth in the tables in WIPO Standard ST.25 (1998), Appendix 2, Tables 1 and 3. Only one strand of each nucleic acid sequence is shown, but the complementary strand is understood as included in embodiments where it would be appropriate. A computer readable text file, entitled "O046-0034US_SeqList.txt" created on or about Sep. 27, 2022, with a file size of 144 KB, contains the sequence listing for this application and is hereby incorporated by reference in its entirety.

| SEQ ID NO: | Sequence Description |
|---|---|
| 1 | CDRH1 for antibody from hybridoma DG1A11 |
| 2 | CDRH2 for antibody from hybridoma DG1A11 |
| 3 | CDRH3 for antibody from hybridoma DG1A11 |
| 4 | CDRL1 for antibody from hybridoma DG1A11 |
| 5 | CDRL2 for antibody from hybridoma DG1A11 |
| 6 | CDRL3 for antibody from hybridoma DG1A11 |
| 7 | variable heavy domain (VH) amino acid sequence for antibody from hybridoma DG1A11 |
| 8 | heavy chain amino acid sequence for antibody from hybridoma DG1A11 |
| 9 | variable light domain (VL) amino acid sequence for antibody from hybridoma DG1A11 |
| 10 | DG1A11 light chain amino acid sequence for antibody from hybridoma DG1A11 |
| 11 | CDRH1 for antibody from hybridoma DGH6 |
| 12 | CDRH2 for antibody from hybridoma DGH6 |
| 13 | CDRH3 for antibody from hybridoma DGH6 |
| 14 | CDRL1 for antibody from hybridoma DGH6 |
| 15 | CDRL2 for antibody from hybridoma DGH6 |
| 16 | CDRL3 for antibody from hybridoma DGH6 |
| 17 | variable heavy domain (VH) amino acid sequence for antibody from hybridoma DGH6 |
| 18 | heavy chain amino acid sequence for antibody from hybridoma DGH6 |
| 19 | variable light domain (VL) amino acid sequence for antibody from hybridoma DGH6 |
| 20 | light chain amino acid sequence for antibody from hybridoma DGH6 |
| 21 | CDRH1 for antibody from hybridoma DG4H4 |
| 22 | CDRH2 for antibody from hybridoma DG4H4 |
| 23 | CDRH3 for antibody from hybridoma DG4H4 |
| 24 | CDRL1 for antibody from hybridoma DG4H4 |
| 25 | CDRL2 for antibody from hybridoma DG4H4 |
| 26 | CDRL3 for antibody from hybridoma DG4H4 |
| 27 | variable heavy domain (VH) amino acid sequence for antibody from hybridoma DG4H4 |
| 28 | DG4H4 heavy chain amino acid sequence for antibody from hybridoma DG4H4 |
| 29 | DG4H4 variable light domain (VL) amino acid sequence for antibody from hybridoma DG4H4 |
| 30 | DG4H4 light chain amino acid sequence for antibody from hybridoma DG4H4 |
| 31 | nucleotide sequence encoding heavy chain of antibody from hybridoma DG1A11 reverse translated from SEQ ID NO: 8 with most likely codons |
| 32 | nucleotide sequence encoding heavy chain of antibody from hybridoma DG1A11 reverse translated from SEQ ID NO: 8 with consensus codons |
| 33 | nucleotide sequence encoding light chain of antibody from hybridoma DG1A11 reverse translated from SEQ ID NO: 10 with most likely codons |
| 34 | nucleotide sequence encoding light chain of antibody from hybridoma DG1A11 reverse translated from SEQ ID NO: 10 with consensus codons |
| 35 | nucleotide sequence encoding heavy chain of antibody from hybridoma DGH6 reverse translated from SEQ ID NO: 18 with most likely codons |
| 36 | nucleotide sequence encoding heavy chain of antibody from hybridoma DGH6 reverse translated from SEQ ID NO: 18 with consensus codons |
| 37 | nucleotide sequence encoding light chain of antibody from hybridoma DGH6 reverse translated from SEQ ID NO: 20 with most likely codons |
| 38 | nucleotide sequence encoding light chain of antibody from hybridoma DGH6 reverse translated from SEQ ID NO: 20 with consensus codons |
| 39 | nucleotide sequence encoding heavy chain of antibody from hybridoma DG4H4 reverse translated from SEQ ID NO: 28 with most likely codons |
| 40 | nucleotide sequence encoding heavy chain of antibody from hybridoma DG4H4 reverse translated from SEQ ID NO: 28 with consensus codons |
| 41 | nucleotide sequence encoding light chain of antibody from hybridoma DG4H4 reverse translated from SEQ ID NO: 30 with most likely codons |
| 42 | nucleotide sequence encoding light chain of antibody from hybridoma DG4H4 reverse translated from SEQ ID NO: 30 with consensus codons |
| 43 | Human dystroglycan (UniProt Accession Q14118) |

-continued

| SEQ ID NO: | Sequence Description |
|---|---|
| 44 | Exemplary AviTag™ |
| 45 | Exemplary CBP (calmodulin binding peptide) |
| 46 | Exemplary polyglutamate tag |
| 47 | Exemplary E tag |
| 48 | Exemplary FLAG tag |
| 49 | Exemplary FLAG tag |
| 50 | Exemplary FLAG tag |
| 51 | Exemplary HA tag |
| 52 | Exemplary HA tag |
| 53 | Exemplary HA tag |
| 54 | Exemplary Myc tag |
| 55 | Exemplary poly His tag |
| 56 | Exemplary S tag |
| 57 | Exemplary SBP (streptavidin binding peptide) |
| 58 | Exemplary Softag 1 |
| 59 | Exemplary Softag 3 |
| 60 | Exemplary Strep tag |
| 61 | Exemplary Strep tag |
| 62 | Exemplary TC tag |
| 63 | Exemplary V5 tag |
| 64 | Exemplary VSV tag |
| 65 | Exemplary Xpress tag |

Nucleotide sequences showing in SEQ ID NOs: 31-42 have been reverse translated using the Sequence Manipulation Suite: Reverse Translate available on the World Wide Web at bioinformatics.org/sms2/rev_trans.html and a mouse codon usage table obtained from the World Wide Web at genscript.com/tools/codon-frequency-table. Reverse Translate accepts an amino acid sequence as input and generates a nucleotide sequence representing the most likely non-degenerate coding sequence given the provided codon usage table ('with most likely codons'). A consensus sequence derived from all the possible codons for each amino acid is also returned ('with consensus codons').

DETAILED DESCRIPTION

The compositions and methods of the present disclosure takes advantage of a pathway for the efficient delivery of agents to the interior of diseased cells, building upon previous work (Leonoudakis et al., *J Cell Sci.*, 127(22): 4894-4903, 2014; US 2015/0374845). This technology enables creation of a range of targeting bioconjugates with applications for imaging and detection of diseased cells, and also for targeted therapeutic (e.g., drug, nucleic acid, or nanoparticle) delivery for disease treatment. The targeting technology is particularly applicable for targeted topical treatment of superficial diseases, including pre-invasive cancers of the bladder and skin. In particular embodiments, a topical treatment in the present disclosure refers to treatment that includes administration of a composition described herein to a surface of living cells. In particular embodiments, the living cells are in vivo. In particular embodiments, the living cells are ex vivo. In particular embodiments, the surface is an epithelium cell layer lining an exterior surface of the body (for example, the skin) or a space, tube, cavity, or lumen of an internal tissue or organ that communicates with the outside environment (for example, the alimentary, respiratory, or genitourinary tracts). In particular embodiments, the tissue or organ having an epithelium cell layer lining a space, tube, cavity, or lumen includes bladder, kidney, ureter, urethra, uterus, fallopian tubes, vagina, digestive tract, mouth esophagus, stomach, small intestine, large intestine, colon, liver, pancreas, upper respiratory tract, pharynx, trachea, lung, exocrine glands, or exocrine gland ducts. In particular embodiments, the surface is on the lumenal or cavity side of a tissue or organ including cells that have lost apical-basal polarity. In particular embodiments, the tissue or organ includes bladder and the administration is intravesicular. In other particular embodiments, the tissue or organ includes uterus and the administration is intrauterine. In yet other particular embodiments, the administration is oral.

Bladder cancers are diagnosed in approximately 70,000 people each year and result in 15,000 deaths in the United States (US) alone, accounting for roughly 7% of all new cancers, and 3% of cancer deaths in the US. Among newly discovered bladder cancers, 75% present as noninvasive carcinoma (papillary and carcinoma in situ) and 25% as muscle invasive disease. Of the noninvasive bladder cancers detected and treated, 50% will recur, and 5% will progress to invasive disease. As a result, there are roughly 500,000 people living with bladder cancer in the US. Currently, the methods for detection, monitoring, and treatment of bladder cancers are costly and ineffective, as evidenced by the high rate of recurrence. Because of the high recurrence, repeated monitoring and treatment, bladder cancers are the costliest of all cancers to treat per capita. Outcomes for bladder cancer patients can be improved through the creation of a targeted therapeutic for more effective treatment of pre-invasive bladder cancers.

An important opportunity for improved bladder cancer treatment lies in the development of reagents that are selectively bound and internalized by bladder cancer cells when administered directly into the bladder. The targeted delivery can also improve diagnosis and monitoring of bladder cancers.

Aspects of the current disclosure are now described in additional detail, as follows: (1) Apical-Basal Polarity; (II) Dystroglycan; (Ill) Antibodies; (IV) Payloads; (V) Target Cells; (VI) Bladder Cancer; (VII) Assays and models to characterize anti-DG antibodies; (VIII) Controls and Test Samples; (IX) Compositions; (X) Methods of Use; (XI) Kits; (XII) Variants; (XIII) Exemplary Embodiments; and (XIV) Examples.

(I) APICAL-BASAL POLARITY

Epithelial cells are a basic cell type that line the internal or external surfaces of many organs and have specialized functions in the directional secretion or absorption of molecules to and from tissue cavities, and in the protection of underlying cell layers from the external environment. In accordance with their functions, these cells are inherently oriented or "polarized", have a distinct "top" and "bottom" referred to as the apical and basal (or basolateral) domains (for example, illustrated in a figure from World Wide Web at biology-pages.info/J/Junctions.html). The apical domain of the epithelium cell layer lining a space, tube, cavity, or lumen of an internal tissue or organ that communicates with the outside environment (for example, the alimentary, respiratory, or genitourinary tracts) faces the external environment, whereas the basal domain faces the internal tissues and blood supply. "Lumenal" and "luminal" can be used interchangeably and pertain to a lumen. This polarity is referred to as apical-basal polarity. This polarity is evident in many aspects of epithelial cell architecture, including the polarized distribution of organelles within the cells (e.g. the nucleus and Golgi apparatus), the polarized orientation of cell surface proteins and adhesion junctions, and the directional regulation of protein trafficking in accordance with the apical and basal domains. A hallmark of this apical-basal polarity is the separation of the cell's plasma membrane (or lipid bi-layer) into apical and basal domains, and the segregation of cell surface proteins between these domains. This molecular segregation is enabled by the formation and maintenance of cell-cell junctions, including adherens and tight junctions, which form a physical barrier to the diffusion of membrane proteins within the lipid bi-layer (or plasma membrane). With this barrier intact, proteins directed uniquely to the basolateral membrane domain are restricted from the apical domain, and vice versa. In particular embodiments, a cell that has apical-basal polarity includes a cell that: has polarized distribution of organelles within the cell; has polarized orientation of cell surface proteins; has polarized orientation of adhesion junctions; has directional regulation of protein trafficking in accordance with apical and basal domains; has separation of the plasma membrane into apical and basal domains; has segregation of cell surface proteins between apical and basal domains; has presence of cell-cell junctions; or a combination thereof.

The loss of apical-basal polarity is implicated in a number of diseases including polycystic kidney disease, retinitis pigmentosa, cystic fibrosis, interstitial cystitis and carcinomas (Wilson, *Biochimica et Biophysica Acta—Mol Basis Dis* 1812, 1239-1248, 2011; Royer & Lu, *Cell Death Diff* 18, 1470-1477, 2011). Loss of apical-basal polarity is a hallmark of disease and can be a driving force in disease progression. The adherens and tight junctions are targets of congenic protein signaling, and loss of integrity in these junctions is an early event in cancers (Khursheed & Bashyam, *J Biosci* 39, 145-155, 2014). Basal and lumenal extrusions of cells that have lost apical-basal polarity can lead to epithelial and lumen tumors (Ohsawa et al., *Developmental Cell,* 44(3): 284-296, 2018).

The loss of apical-basal polarity is most often detected by analysis of tissue biopsies, using fixed and stained tissue slices, and observing migration of cell nuclei toward the apical surface, migration of Golgi to the basal surface, and other markers such as the polarized secretion of extracellular molecules (U.S. Pat. No. 8,655,035). Other methods to detect loss of apical-basal polarity include assessing absence of apically polarized tight junctions between cells and/or assessing absence of polar distribution of cellular organelles and cell surface proteins. Loss of polarity in living tissues can also be observed in the redistribution of cell surface proteins that occurs with breakdown of the cell-cell junctions that establish the apical-basal membrane barrier. For example, the mixing or mis-localization of typically apical or basolateral proteins at the cell surface would indicate loss of polarity in the cell. In another example, loss of tight junctions can be observed by loss of discrete immunostaining of ZO-1, a tight junction scaffolding protein.

In particular embodiments, the antibodies or antigen-binding fragments thereof described herein do not bind to dystroglycan in cells that have apical-basal polarity if presented to the cells only from the lumenal (apical) side. In particular embodiments, the antibodies or antigen-binding fragments thereof described herein do bind to dystroglycan on the lumenal side in cells that have lost apical-basal polarity (e.g., cancer cells). Due to disruption of cell-cell junctions in cells that have lost apical-basal polarity, the restricted basolateral localization of dystroglycan is abolished, redistributing dystroglycan throughout the cell membrane including to the apical side. In particular embodiments, cells that have lost apical-basal polarity had apical-basal polarity at some point in their existence and have lost apical-basal polarity due to a biological dysfunction, e.g., altered expression of polarity proteins due to gene amplification, gene deletion, and/or epigenetic regulation. In particular embodiments, the loss of apical-basal polarity in cells leads to neoplasms. In particular embodiments, the loss of apical-basal polarity in cells is coincident with or associated with neoplasms.

In other particular embodiments, the antibodies or antigen-binding fragments thereof described herein bind to dystroglycan expressed on the surface of cells that are not normally polarized. In some embodiments, the antibodies or antigen-binding fragments thereof are used to administer a payload to a cell where the loss of apical-basal polarity of the cell is not required for delivery of the payload.

(II) DYSTROGLYCAN (DG)

Dystroglycan (DG), also known as Dystrophin-Associated Glycoprotein 1 (DAG1), is a prominent and widely expressed cell surface receptor that includes two subunits that result from cleavage of a single precursor protein: a transmembrane protein $\beta$-DG and its interacting extracellular peripheral glycoprotein $\alpha$-DG. The DG dimer is involved in a number of processes including laminin and basement membrane assembly, sarcolemmal stability, cell survival, peripheral nerve myelination, nodal structure, cell migration, and epithelial polarization. $\alpha$-DG binds to a number of proteins including: ECM proteins containing laminin-G domains, laminin-2 (LAMA2), and agrin in peripheral nerve Schwann cells. DG plays important roles in connecting the ECM to the cytoskeleton. DG functions in cell adhesion-mediated signaling and is implicated in cell polarity.

DG includes the following regions: amino acids 30-408 for laminin recognition; amino acids 316-485 as a mucin-like domain; amino acids 819-895 for interaction with caveolin-3 (CAV3); and amino acids 880-895 for binding dystrophin (DMD) and utrophin (UTRN), large cytoskeletal proteins. All amino acid positions are with reference to human dystroglycan protein sequence (SEQ ID NO: 43). DG includes a helical transmembrane region (amino acids 750-775), and a cytoplasmic region (amino acids 776-895). The $\alpha$-DG subunit includes amino acids 30-653, and the $\beta$-DG subunit includes amino acids 654-895. A signal peptide of DG includes amino acids 1-29. DG is a glycosylated protein, having O-glycosylation sites at positions including amino acids 63, 317, 319, 367, 369, 372, 379, 381, 388, and 455, and N-glycosylation sites at positions including amino acids 141, 641, 649, and 661. O-glycosylation also occurs in a region including amino acids 169-200 and 463-485. In particular embodiments, variable DG glycosylation includes variations in the carbohydrate modifications of the α-DG subunit that produce changes in the mass of the α-DG subunit, and lead to the addition or absence of functional carbohydrate modifications that are detectable by binding of the IIH6 monoclonal antibody (Kanagawa et al., Cell, 117 (7):953-64, 2004; and Inamori et al. Science, 335 (6064): 93-6, 2012. In particular embodiments, variable DG glycosylation includes at least one posttranslational modification of α-DG by the like-acetylglucosaminyltransferase (LARGE).

DG is a highly efficient mediator of endocytosis in a wide range of cell types, being more effective at internalization than related molecules such as the 31 integrins (Leonoudakis et al., *J Cell Sci.,* 127(22): 4894-4903, 2014).

DG can be a useful molecule in the selective targeting of reagents to cancers. DG exhibits an asymmetric localization in polarized epithelial cells, being restricted to the basolateral domain and not found at the apical domain of these cells. DG is redistributed in cancerous tissue upon loss of polarity by cancer cells. Consequently, the loss of tissue architecture in cancers where the apical-basal polarity is compromised provides unique opportunities for selective

14 proteins in the diseased cells. Consequently, therapeutic strategies using these existing reagents are not specific to cancer cells and can lead to off target effects. Moreover, resistance to the immunotoxins can develop based on the absence of the target. In contrast, in some embodiments, the compositions described herein target cancers by the characteristic changes in tissue architecture that accompany cancer progression, not by changes in gene expression. DG-binding antibodies or antigen-binding fragments thereof described herein can be used to selectively and efficiently target imaging agents to cells having DG localized on their cell surface for diagnostic or imaging purposes and/or target therapeutic agents to cells having DG localized on their cell surface for therapeutic purposes. Moreover, by combining cancer detection and treatment in a single composition, the antibodies or antigen-binding fragments thereof of the present disclosure also represent a "theranostic" for cancers.

In particular embodiments, the compositions described herein target cells that express DG. The cells that express DG can be diseased cells or healthy cells.

(III) ANTIBODIES. AN ANTIBODY OF THE PRESENT DISCLOSURE INCLUDES ANTIBODIES IN TABLE 1

TABLE 1

| Antibodies from hybridomas and associated SEQ ID NOs of the present disclosure | | | | | | |
| Hybridoma | ATCC§ Patent Deposit No. | VH CDR SEQ ID NOs | VL CDR SEQ ID NOs | VH SEQ ID NO | Heavy chain SEQ ID NOs | VL SEQ ID NO | Light chain SEQ ID NOs |
| --- | --- | --- | --- | --- | --- | --- | --- |
| DG1A11 | PTA-126595 | 1-3 | 4-6 | 7 | 8, 31, 32* | 9 | 10, 33, 34 |
| DGH6 | PTA-126593 | 11-13 | 14-16 | 17 | 18, 35, 36 | 19 | 20, 37, 38 |
| DG4H4 | PTA-126594 | 21-23 | 24-26 | 27 | 28, 39, 40 | 29 | 30, 41, 42 |

*Underlined SEQ ID NOs are nucleotide sequences; SEQ ID NOs not underlined are amino acid sequences
§American Type Culture Collection, ATTC ® Patent Depository, 10801 University Blvd, Manassas, Virginia, 20110, USA.

targeting of cancer cells. A labeled DG binding molecule, such as laminin-111, can detect whether there is an absence or loss of apical-basal polarity in a cell when introduced at the apical surface of the cell. The kinetics of internalization and trafficking are such that molecules internalized by DG have a long duration in the cell interior, allowing for a durable detection signal. It has been observed that DG traffics bound molecules to the lysosome, which is advantageous for the activation of certain drugs or drug conjugates. Therefore, DG-binding antibodies or antigen-binding fragments thereof described herein can be used to selectively and efficiently target imaging agents and/or therapeutic agents to cells expressing DG on their cell surface. In particular embodiments, the cells targeted by DG-binding antibodies or antigen-binding fragments thereof lack apical-basal polarity. In other embodiments, the DG is localized to the luminal side of cells lacking apical-basal polarity. In particular embodiments, an anti-DG antibody attached to a payload can be internalized into endocytic vesicles within a cell upon binding of the anti-DG antibody/payload complex to DG. In particular embodiments, endocytic vesicles include late endosomes and/or lysosomes. In particular embodiments, endocytic vesicles include acidic vesicles.

Immunotoxins currently in development target cancer cells based principally on over-expression of particular Although DG-binding antibodies for detection of the extracellular domains of DG are commercially available, including VIA4 and IIH6 monoclonal antibodies, these commercially available antibodies are sensitive to changes in α-DG glycosylation (Hara et al., *Proc Natl Acad Sci,* 108:17426-17431, 2011). Antibody generation efforts by other laboratories have demonstrated the challenge of creating antibodies that are not influenced by variations in DG glycosylation (e.g., see Humphrey et al., *Neuromuscul Disord.,* 1:32-42, 2015). The present disclosure is believed to be the first to describe anti-DG antibodies with a bound payload that bind DG and are internalized in living cells. In particular embodiments, the binding of the disclosed antibodies to DG is independent of variable DG glycosylation.

An antibody of the present disclosure includes any immunoglobulin or intact molecule as well as fragments thereof that bind to a specific epitope. Such antibodies include polyclonal, monoclonal, chimeric, humanized, single chain, Fab, Fab', F(ab')₂, and/or Fv portions of the whole antibody and variants thereof. Antibodies and antigen-binding fragments of the disclosure can include IgG, IgE, IgM, IgD, IgA and IgY isotypes and IgG1, IgG2, IgG3, IgG4, IgA1, and IgA2 subclasses.

An intact antibody can include at least two heavy (H) chains and two light (L) chains inter-connected by disulfide bonds. Each heavy chain is composed of a heavy chain variable region (abbreviated herein as VH or $V_H$) and a heavy chain constant region. The heavy chain constant region includes three domains, CH1, CH2 and CH3. Each light chain is composed of a light chain variable region (abbreviated herein as VL or $V_L$) and a light chain constant region. The light chain constant region includes one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The precise amino acid sequence boundaries of a given CDR or FR can be readily determined using any of a number of well-known schemes, including those described by: Kabat et al., (1991) "Sequences of Proteins of Immunological Interest," 5th Ed. Public Health Service, National Institutes of Health, Bethesda, MD (Kabat numbering scheme); Al-Lazikani et al., *J Mol Biol* 273: 927-948, 1997 (Chothia numbering scheme); Maccallum et al., *J Mol Biol* 262: 732-745, 1996 (Contact numbering scheme); Martin et al., *Proc. Natl. Acad. Sci.,* 86: 9268-9272, 1989 (AbM numbering scheme); Lefranc et al., *Dev Comp Immunol* 27(1): 55-77, 2003 (IMGT numbering scheme); and Honegger & Pluckthun, *J Mol Biol* 309(3): 657-670, 2001 ("Aho" numbering scheme). The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. In particular embodiments, the antibody CDR sequences disclosed herein are according to Chothia numbering.

A monoclonal antibody (mAb) of the present disclosure includes a preparation of antibody molecules of single molecular composition. A monoclonal antibody composition displays a single binding specificity and affinity for a particular epitope. In particular embodiments, a human monoclonal antibody refers to antibodies displaying a single binding specificity which have variable and constant regions (if present) derived from human germline immunoglobulin sequences. Particular embodiments include human monoclonal antibodies produced by a hybridoma which includes a B cell obtained from a transgenic non-human animal, e.g., a transgenic mouse, having a genome including a human heavy chain transgene and a light chain transgene fused to an immortalized cell. Monoclonal antibodies of the present disclosure include DG1A11, DGH6, and DG4H4 that bind to dystroglycan.

Human antibodies include antibodies having variable and constant regions (if present) derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). Such antibodies can be generated in non-human transgenic animals, e.g., as described in WO 01/14424 and WO 00/37504. Human antibodies do not include antibodies in which CDR sequences derived from the germline of another mammalian species, such as a mouse, have been grafted onto human framework sequences (e.g., humanized antibodies).

A humanized antibody includes at least one antibody molecule in which the amino acid sequence in the non-antigen-binding regions and/or the antigen-binding regions has been altered so that the antibody more closely resembles a human antibody, and still retains its original binding ability. In particular embodiments, humanized antibodies are antibody molecules from non-human species having one or more CDRs from the non-human species and a framework region from a human immunoglobulin molecule. Techniques have been developed for the production of humanized antibodies (see, e.g., U.S. Pat. Nos. 5,585,089 and 5,225, 539).

In particular embodiments, chimeric antibodies can be produced by splicing the genes from a mouse antibody molecule of appropriate antigen specificity together with genes from a human antibody molecule of appropriate biological activity (Morrison, et al., Proc Natl Acad Sci, 81:6851-6855, 1984). For example, the genes from a mouse antibody molecule specific for an autoinducer can be spliced together with genes from a human antibody molecule of appropriate biological activity. A chimeric antibody is a molecule in which different portions are derived from different animal species, such as those having a variable region derived from a murine mAb and a human immunoglobulin constant region.

In particular embodiments, recombinant immunoglobulins can be produced. See, Cabilly, U.S. Pat. No. 4,816,567, and Queen et al., *Proc Natl Acad Sci USA,* 86:10029-10033, 1989.

In particular embodiments, an antibody includes antigen-binding portions of an intact antibody that retain capacity to bind. An antibody fragment includes an incomplete or isolated portion of the full sequence of an antibody which retains the antigen-binding function of the parent antibody. Examples of fragments that retain capacity to bind include: (i) an Fab fragment, a monovalent fragment including the VL, VH, CL and CH1 domains; (ii) a $F(ab')_2$ fragment, a bivalent fragment including two Fab fragments linked by a disulfide bridge at the hinge region; (iii) an Fd fragment including the VH and CH1 domains; (iv) an Fv fragment including the VL and VH domains of a single arm of an antibody, (v) a single domain (dAb) fragment (Ward et al., Nature, 341:544-546, 1989), including a VH domain; (vi) an isolated complementarity determining region (CDR); and (vii) a single chain variable fragment including a variable heavy chain and a variable light chain connected through a flexible linker (e.g., a Gly-Ser linker). Other exemplary antibody fragments include Fab', diabodies, single chain antibody molecules, and multi-specific antibodies formed from antibody fragments.

Single chain antibodies or single chain Fv (scFv) includes an antibody fusion molecule of the two domains of the Fv fragment, VL and VH. Although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al., *Science*, 242:423-426, 1988; and Huston et al., *Proc Natl Acad Sci USA*, 85:5879-5883, 1988). In particular embodiments, such single chain antibodies are included in antibody fragments and can be prepared by recombinant techniques or enzymatic or chemical cleavage of intact antibodies.

Fab and F(ab')$_2$ portions of antibody molecules can be prepared by the proteolytic action of papain and pepsin, respectively, on substantially intact antibody molecules by methods that are well-known. See e.g., U.S. Pat. No. 4,342,566. Fab' antibody molecule portions are also well-known and are produced from F(ab')$_2$ portions followed by reduction of the disulfide bonds linking the two heavy chain portions with a reducing agent such as mercaptoethanol, and then followed by alkylation of the resulting protein mercaptan with a reagent such as iodoacetamide.

An antigen includes a substance that prompts the generation of antibody(s) and can cause an immune response. An antigen or fragment thereof can be a molecule (i.e., an epitope) that contacts a particular antibody. When a protein or a fragment of a protein is used to immunize a host animal, numerous regions of the protein can induce the production of antibodies (i.e., elicit the immune response), which bind specifically to the antigen (given regions or three-dimensional structures on the protein). In particular embodiments, antigens include substances that bind to specific antibodies. Antigen can be used interchangeably in the present disclosure with immunogen. In particular embodiments, immunogens include substances that elicit a response from the immune system.

An epitope includes the portion of the antigen bound by an antibody. Antigens can include multiple epitopes. Where the antigen is a protein, linear epitopes can range from 5 to 20 amino acids in length. Antibodies can also recognize conformational determinants formed by non-contiguous residues on an antigen, and an epitope can therefore require a larger fragment of the antigen to be present for binding, e.g. a protein domain, or substantially all of a protein sequence. It will therefore be appreciated that a protein, which can be several hundred amino acids in length, can include a number of distinct epitopes. Binding can also be detected by visualization of a label (such as a fluorescent label) conjugated to one of the molecules.

Once an antibody molecule of the present disclosure has been produced by an animal, a cell line, chemically synthesized, or recombinantly expressed, it can be purified (i.e., isolated) by any method known in the art for the purification of an immunoglobulin or polypeptide molecule, for example, by chromatography (e.g., ion exchange, affinity, particularly by affinity for dystroglycan, Protein A, and sizing column chromatography), centrifugation, differential solubility, or by any other standard technique for the purification of proteins. In addition, the antibodies or antigen-binding fragments thereof of the present disclosure can be fused to heterologous polypeptide sequences known in the art to facilitate purification.

The affinity between an antibody and a target or ligand (such as an antigen used to generate a given antibody) may be measured in terms of $K_D$ using one or more binding assays known in the art. Depending on the desired application for a given antibody, varying $K_D$ values may be desirable. High affinity antibodies typically form ligand bonds with a $K_D$ of $10^{-5}$ M or less, $10^{-6}$ M or less, $10^{-7}$ M or less, $10^{-8}$ M or less, $10^{-9}$ M or less, $10^{-10}$ M or less, $10^{-11}$ M, or less or $10^{-12}$ M or less.

(IV) PAYLOADS

Compositions of the present disclosure can include one or more payloads; the one or more payloads in some embodiments is attached to an antibody or antigen-binding fragment thereof as disclosed herein. In particular embodiments, an immunoconjugate includes one or more payloads attached to an antibody or antigen-binding fragment thereof as disclosed herein. Payloads can include agents for: detection or imaging of DG and/or DG-expressing cells; and diagnosing and treating disorders associated with loss of apical-basal polarity in cells. In particular embodiments, a payload can include a biologically functional molecule. A biologically functional molecule can function on a cell, inside a cell, or in an organism. Examples of biologically functional molecules include a nucleic acid (such as an siRNA, an mRNA, a microRNA (miRNA), or an oligonucleotide), a nanoparticle, a nanoparticle including a nucleic acid, enzymes, enzyme substrates, radioisotopes, toxins, small molecule drugs, and additional molecules, as described herein. In particular embodiments, one or more payloads can be attached to an anti-DG antibody.

In particular embodiments, a payload includes a therapeutic agent. The therapeutic agent can be detrimental to the growth or further survival of the cell to which the agent is targeted by the antibodies and antigen-binding fragments thereof of the present disclosure. Said toxicity would be selective due to the binding of the anti-DG antibody/payload complex on the cell surface and/or the internalization of the anti-DG antibody/payload complex into the cell. Therapeutic agents can include a cytotoxin, radioactive isotopes, chemotherapeutic, or other therapeutic agent. A cytotoxin or cytotoxic agent includes any agent that may be detrimental to cells. Examples include taxol, cytochalasin B, gramicidin D, ethidium bromide, emetine, mitomycin, etoposide, teniposide, vincristine, vinblastine, colchicine, doxorubicin, daunorubicin, dihydroxyanthracinedione, mitoxantrone, mithramycin, actinomycin D, 1-dehydrotestosterone, glucocorticoids, procaine, tetracaine, lidocaine, propranolol, puromycin, maytansinoids, e.g., maytansinol (U.S. Pat. No. 5,208,020), rachelmycin (CC-1065, U.S. Pat. Nos. 5,475,092; 5,585,499; and 5,846,545), and analogs or homologs thereof. Radioactive isotopes include iodine (e.g., iodine 125 or iodine 131), strontium 89, phosphorous, palladium, cesium, iridium, phosphate, cobalt, yttrium 90, samarium 153, and praseodymium. Other therapeutic agents include antimetabolites (e.g., methotrexate, 6-mercaptopurine, 6-thioguanine, cytarabine, 5-fluorouracil decarbazine), alkylating agents (e.g., mechlorethamine, thiotepa chlorambucil, rachelmycin (CC-1065), melphalan, carmustine (BSNU), lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). In particular embodiments, the therapeutic agent is paclitaxel. In particular embodiments, the therapeutic agent is maytansine DM1.

In particular embodiments, the payload includes a nucleic acid. In certain embodiments, the nucleic acid includes siRNA (small interfering RNA), mRNA, DNA, RNA, LNA, PNA, miRNA, chimeric nucleic acid, modified nucleic acid, single stranded nucleic acid, double stranded nucleic acid, aptamer, and/or chemically modified nucleic acid. In certain embodiments, the nucleic acid includes a nucleic acid barcode. A nucleic acid barcode includes a random stretch of nucleotides that serves as a unique tag to Identify a molecule that the barcode is attached to.

In particular embodiments, the payload may be a detectable agent. The detectable agent can be conjugated directly or indirectly to another molecule to facilitate detection of the detectable agent. In particular embodiments, detectable agents can be used to detect DG on a cell surface or DG internalized in endocytic vesicles within a cell. In particular embodiments, detectable agents include dyes, contrast agents, fluorescent tags, enzymes, radioactive isotopes, molecules that specifically bind other molecules (affinity tags, e.g., biotin or streptavidin) and compounds visible in MRI imaging such as MRI contrast agents. In particular embodiments, detectable agents include various organic small molecules, inorganic compounds, nanoparticles, enzymes or enzyme substrates (e.g., horseradish peroxidase (HRP), alkaline phosphatase (AP), glucose oxidase, luciferase, and β-galactosidase, which can be used in conjunction with colorimetric, fluorogenic, or chemiluminescent substrates for visualization), fluorescent materials, luminescent materials (e.g., luminol), bioluminescent materials (e.g., luciferase, luciferin, and aequorin), chemiluminescent materials, radioactive materials (e.g., $^{18}$F, $^{67}$Ga, $^{81m}$Kr, $^{82}$Rb, $^{111}$In, $^{123}$I, $^{133}$Xe, $^{201}$Tl, $^{125}$I, $^{35}$S, $^{14}$C $^3$H, or $^{99m}$Tc, and contrast agents (e.g., gold (e.g., gold nanoparticles), gadolinium (e.g., chelated Gd), iron oxides (e.g., superparamagnetic iron oxide (SPIO), monocrystalline iron oxide nanoparticles (MI-ONs), and ultrasmall superparamagnetic iron oxide (US-PIO)), manganese chelates (e.g., Mn-DPDP), barium sulfate, iodinated contrast media (iohexol), microbubbles, or perfluorocarbons). Optically detectable labels include 4-acetamido-4'-isothiocyanatostilbene-2,2'disulfonic acid; acridine and derivatives (e.g., acridine and acridine isothiocyanate); 5-(2'-aminoethyl)aminonaphthalene-1-sulfonic acid (EDANS); 4-amino-N-[3-vinylsulfonyl) phenyl]naphthalimide-3,5 disulfonate; N-(4-anilino-1-naphthyl)maleimide; anthranilamide; BODIPY; Brilliant Yellow; coumarin and derivatives (e.g., coumarin, 7-amino-4-methylcoumarin (AMC, Coumarin 120), and 7-amino-4-trifluoromethylcoumarin (Coumarin 151)); cyanine dyes; cyanosine; 4',6-diaminidino-2-phenylindole (DAPI); 5' 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]-naphthalene-1-sulfonyl chloride (DNS, dansylchloride); 4-dimethylaminophenylazophenyl-4'-isothiocyanate (DABITC); eosin and derivatives (e.g., eosin and eosin isothiocyanate); erythrosin and derivatives (e.g., erythrosin B and erythrosin isothiocyanate); ethidium; fluorescein and derivatives (e.g., 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, X-rhodamine-5-(and-6)-isothiocyanate (QFITC or XRITC), and fluorescamine); 2-[2-[3-[[1,3-dihydro-1,1-dimethyl-3-(3-sulfopropyl)-2H-benz[e]indol-2-ylidene]ethylidene]-2-[4-(ethoxycarbonyl)-1-piperazinyl]-1-cyclopenten-1-yl]ethenyl]-1,1-dimethyl-3-(3-sulforpropyl)-1H-benz[e]indolium hydroxide, inner salt, compound with n,n-diethylethanamine(1:1) (IR144); 5-chloro-2-[2-[3-[(5-chloro-3-ethyl-2(3H)-benzothiazol-ylidene)ethylidene]-2-(diphenylamino)-1-cyclopenten-1-yl] ethenyl]-3-ethyl benzothiazolium perchlorate (IR140); Malachite Green isothiocyanate; 4-methylumbelliferone orthocresolphthalein; nitrotyrosine; pararosaniline; Phenol Red; B-phycoerythrin; o-phthaldialdehyde; pyrene and derivatives (e.g., pyrene, pyrene butyrate, and succinimidyl 1-pyrene); butyrate quantum dots; Reactive Red 4 (CIBA-CRON™ Brilliant Red 3B-A); rhodamine and derivatives (e.g., 6-carboxy-X-rhodamine (ROX), 6-carboxyrhodamine (R6G), lissamine rhodamine B sulfonyl chloride rhodarnine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'tetramethyl-6-carboxyrhodamine (TAMRA) tetramethyl rhodamine, and tetramethyl rhodamine isothiocyanate (TRITC)); riboflavin; rosolic acid; terbium chelate derivatives; Cyanine-3 (Cy3); Cyanine-5 (Cy5); cyanine-5.5 (Cy5.5), Cyanine-7 (Cy7); IRD 700; IRD 800; Alexa 647; La Jolta Blue; phthalo cyanine; and naphthalo cyanine.

In particular embodiments, the detectable agent may be a non-detectable precursor that becomes detectable upon activation (e.g., fluorogenic tetrazine-fluorophore constructs (e.g., tetrazine-BODIPY FL, tetrazine-Oregon Green 488, or tetrazine-BODIPY TMR-X) or enzyme activatable fluorogenic agents (e.g., PROSENSE® (VisEn Medical))).

In particular embodiments, a payload can include affinity tags. Examples of affinity tags include: AviTag™ (Avidity, LLC, Aurora, CO, exemplified by SEQ ID NO: 44); biotin; calmodulin binding peptide (CBP, exemplified by SEQ ID NO: 45); cellulose binding domain; chitin binding domain; polyglutamate (exemplified by SEQ ID NO: 46); E tag (exemplified by SEQ ID NO: 47); FLAG tag (exemplified by SEQ ID NOs: 48-50); hemagglutinin antigen (HA) tag (exemplified by SEQ ID NOs: 51-53); Myc tag (exemplified by SEQ ID NO: 54); polyhistidine tag (exemplified by SEQ ID NO: 55); NE synthetic peptide tag; S tag (exemplified by SEQ ID NO: 56); Strep Tag® (e.g. from Novagen, Madison, WI; exemplified by SEQ ID NOs: 60, 61); streptavidin binding peptide (SBP) tag (exemplified by SEQ ID NO: 57); Softag™ (e.g., from Lucigen, Middleton, WI; exemplified by SEQ ID NOs: 58, 59); TC (tetracysteine) tag (exemplified by SEQ ID NO: 62); V5 tag (exemplified by SEQ ID NO: 63); VSV tag (exemplified by SEQ ID NO: 64); Xpress tag (exemplified by SEQ ID NO: 65); BCCP (biotin carboxyl carrier protein); Fc tag; glutathione S-transferase (GST); green fluorescent protein (GFP); HaloTag® (England et al., Bioconjug Chem., 26(6): 975-986, 2015); maltose binding protein (MBP); Nus (N-utilization substance) protein; PDZ domain; PDZ ligand; protein A; protein G; streptavidin; small ubiquitin-related modifier (SUMO); and thioredoxin (TRX).

Methods to detect a payload can include both in vitro and in vivo imaging methods, e.g., immunohistochemistry, flow cytometry, enzyme linked immunosorbent assays (ELISAs), immunoprecipitation assays, immunofluorescence, enzyme immunoassays (EIA), radioimmunoassays (RIA), Western blot analysis, bioluminescence imaging (BLI), magnetic resonance imaging (MRI), positron emission tomography (PET), electron microscopy, X-ray computed tomography, Raman imaging, optical coherence tomography, absorption imaging, thermal imaging, fluorescence reflectance imaging, fluorescence microscopy, fluorescence guided imaging systems, fluorescence molecular tomographic imaging, nuclear magnetic resonance imaging, X-ray imaging, ultrasound imaging, and photoacoustic imaging.

Antibodies and antigen-binding fragments thereof of the present disclosure can be attached to one or more payloads. The attachment can be direct or indirect. In particular embodiments, a direct attachment includes attachment of a portion, residue, or element of a payload to a portion, residue, or element of an antibody or antigen-binding fragment thereof. In particular embodiments, an indirect attachment includes attachment of a portion, residue, or element of a payload to a portion, residue, or element of an antibody or antigen-binding fragment thereof via at least one intervening moiety, e.g., a peptide, protein, nucleic acid, and/or nanoparticle. In particular embodiments, direct and indirect attachments can include covalent bonds or non-covalent interactions. Covalent bonds include the sharing of electrons in a chemical bond. Non-covalent interactions include dispersed electromagnetic interactions such as hydrogen bonds, ionic bonds, van der Waals interactions, and hydrophobic bonds.

In particular embodiments, a payload is directly conjugated to an anti-DG antibody by a linker in any useful orientation. For example, a linker having two ends is used to covalently attach one end to the payload and the other end to a residue on the DG-interacting antibody. The linker can be a cleavable linker. In particular embodiments, a drug may be attached to a DG-interacting antibody via a linker, and the drug may be fluorescently labeled to track the drug in vivo, e.g. intracellularly.

Direct, covalent attachment of a payload to an antibody or antigen-binding fragment thereof of the disclosure can use chemical cross-linking reagents. In particular embodiments, natural or engineered amino acids or carbohydrate moieties in the antibody are covalently linked to the payload. In particular embodiments, the chemical cross-linking reagents can include: N-hydroxysuccinimide (NHS); N-hydroxysulfosuccinimide (sulfo-NHS); N-succinimidyl-3-(2-pyridyldithio) propionate (SPDP); succinimidyl-4-(N-maleimidomethyl) cyclohexane-1-carboxylate (SMCC); N-(β-maleimidopropyloxy)succinimide ester (BMPS); N-ε-maleimidocaproyl-oxysuccinimide ester (EMCS); N-γ-maleimidobutyryl-oxysuccinimide ester (GMBS); m-maleimidobenzoyl-N-hydroxysuccinimide ester (MBS); 4-(4-N-maleimidophenyl)butyric acid hydrazide (MPBH); succinimidyl 3-(bromoacetamido)propionate) (SBAP), succinimidyl iodoacetate (SIA); succinimidyl (4-iodoacetyl) aminobenzoate (SIAB); succinimidyl 4-(p-maleimidophenyl)butyrate (SMPB); succinimidyl 6-((beta-maleimidopropionamido)hexanoate (SMPH); sulfo-EMCS; sulfo-GMBS; N-κ-maleimidoundecanoyl-oxysulfosuccinimide ester (sulfo-KMUS); sulfo-MBS; sulfo-SIAB; sulfo-SMCC; sulfo-SMPB; 1,6-Hexane-bis-vinylsulfone (HBVS); succinimidyl-(4-vinylsulfone)benzoate (SVSB); iminothiolane (IT); bifunctional derivatives of imidoesters (e.g., dimethyl adipimidate HCl); active esters (e.g., disuccinimidyl suberate); aldehydes (e.g., glutaraldehyde); bis-azido compounds (e.g., bis (p-azidobenzoyl) hexanediamine), bis-diazonium derivatives (e.g., bis-(p-diazoniumbenzoyl)-ethylenediamine), diisocyanates (e.g., toluene 2,6-diisocyanate), and bis-active fluorine compounds (e.g., 1,5-difluoro-2,4-dinitrobenzene). Cross-linking methods can include click strategies including [3+2] Azide-alkyne cycloaddition (AAC) reactions catalyzed by copper (I) (CuAAC), strain-promoted [3+2] azide-alkyne cycloaddition (SPAAC) reactions, typical [4+2] Diels-Alder (DA), and inverse electron demand hetero Diels-Alder (iEDDA) reactions. Carbon-14-labeled 1-isothiocyanato-benzyl-3-methyldiethylene triaminepentaacetic acid (MX-DTPA) is an exemplary chelating agent for conjugation of a radionuclide to an antibody (WO94/11026). Chemical cross-linking reagents are commercially available from, for example, Thermo Fisher Scientific, Waltham, MA In particular embodiments, payloads can be covalently attached to an antibody via a photoactivatable functionalized nucleotide derivative that covalently attaches to a nucleotide binding site of an antibody upon irradiation. Strategies for conjugation of a payload to an antibody are discussed in, for example, Juan et al. (2020) Pharmaceutics. 12(9):802 and Nobs et al. (2004). Journal of pharmaceutical sciences, 93(8), 1980-1992.

In particular embodiments, covalent attachment of a payload to an antibody or antigen-binding fragment thereof of the disclosure can be indirect, i.e., the payload is attached to a tag, which is covalently attached to the antibody or antigen-binding fragment thereof. In particular embodiments, conjugation via tags can include use of enzymes that convert specific amino acid tags engineered into antibodies to "handles" for payload attachment (e.g., enzymes can include formylglycin generating enzyme (FGE), sortase A (Srt A), and transglutaminases). In particular embodiments, payloads can be non-covalently attached to an antibody via affinity systems such as avidin/biotin or a functionalized nucleotide derivative that binds a nucleotide binding site of an antibody. In particular embodiments, indirect attachment of a payload includes attaching a payload, either covalently or non-covalently, to a nanoparticle carrier, that is covalently or non-covalently attached to the antibody or antigen-binding fragment thereof.

Attachment of a payload to an antibody or antigen-binding fragment thereof of the disclosure can be non-covalent. In particular embodiments, small domains that bind with high affinity to a conserved sequence in the Fc domain of antibodies can be used, e.g., a ZZ-domain, a dimer of the modified immunoglobulin binding site of protein A of *Staphylococcus aureus*. In particular embodiments, Fc binding domains can be photoactivatable to generate a covalent bond between the Fc binding domain and the antibody upon irradiation.

In particular embodiments, an anti-DG antibody and the payload are present as separate entities. For example, the anti-DG antibody can be bound to the cell and then a second reagent (directly attached to a payload) that binds the anti-DG antibody can be contacted with the cell. For example, a secondary antibody conjugated to a detectable agent and that binds the anti-DG antibody can be used, thereby labeling the DG or DG-expressing cell.

In particular embodiments, an anti-DG antibody and the payload are administered to a subject as separate entities in a pre-targeting strategy, and the anti-DG antibody/payload conjugate is formed in vivo (Patra et al. (2016) Chem. Soc. Rev. 45: 6415). A pre-targeting strategy includes temporarily separating targeting of a cell (e.g., cancer cell) by an antibody from delivery of the therapeutic or diagnostic payload to the cell. For example, an anti-DG antibody without a payload can be administered to a subject in a first step. After administration, sufficient time is allowed for blood circulation of the anti-DG antibody (if administered intravenously), accumulation of the anti-DG antibody at a site that includes target DG expressing cells (for example, if the administration is intravenous, intravesicular, or intrauterine), and subsequent elimination of excess anti-DG antibody from the body. A payload can then be administered to the subject in a subsequent step to attach to local anti-DG antibody at the target cell site. In particular embodiments, the pre-targeting strategy can limit toxicity of a payload on healthy tissues. In particular embodiments, the payload can attach to the antibody via a non-covalent interaction (e.g., strept(avidin)/biotin, hybridization of oligonucleotides) or via a covalent interaction (e.g., an inverse electron demand Diels-Alder reaction between tetrazines (Tz) and trans-cyclooctenes (TCO)) (Ruivo et al., *ACS Omega* 5(9): 4449-4456, 2020).

(V) TARGET CELLS

Cells that can be targeted by an anti-DG antibody or antigen-binding fragment thereof of the disclosure includes a cell that expresses DG. In particular embodiments, the cell is a non-epithelial cell. In particular embodiments, the cell is a non-polarized cell. A non-polarized cell includes: a cell that does not have apical-basal polarity, a cell that does not have any type of polarity, a cell that does not express cell-to-cell junctions, and a cell that has uniform (non-directional) distribution of apical and/or basolateral proteins in the plasma membrane. In particular embodiments, a cell that can be a target for an anti-DG antibody or antigen-binding fragment thereof includes an epithelial cell that has lost apical-basal polarity. In particular embodiments, a cell that can be a target for an anti-DG antibody or antigen-binding fragment thereof can be a normal cell or a diseased cell.

In particular embodiments, an anti-DG antibody or antigen-binding fragment thereof can target the tissues or cells of the following: the blood and immune system, including bone marrow, whole blood, serum, plasma, white blood cells, monocyte, neutrophil, T-lymphocyte, B-lymphocyte, CD4 T cell, CD8 T cell, natural killer cell, peripheral blood mononuclear cell, platelet, thymus, tonsil, lymph node, bone marrow stromal cell, and bone marrow mesenchymal stem cell; the nervous system, including brain, fetal brain, cortex, prefrontal cortex, cerebral cortex, cerebellum, cerebrospinal fluid, spinal cord, tibial nerve, retina, and retinal pigment epithelium; the musculoskeletal system including, heart, fetal heart, artery, bone, smooth muscle, skeletal muscle, and colon muscle; the internal system, including oral epithelium, nasopharynx, nasal respiratory epithelium, esophagus, stomach, cardia, gut, fetal gut, colon, colonic epithelial cell, small intestine, rectum, liver, fetal liver, liver secretome, kidney, spleen, lung, lung alveolar lavage, adipocyte, synovial fluid, and amniocyte; the secretory system, including vitreous humor, saliva, salivary gland, thyroid gland, adrenal gland, pituitary gland, breast, milk, pancreas, pancreatic juice, pancreatic islet, gall bladder, prostate, urine, urinary bladder, skin, hair follicle, and placenta; and the reproductive system including: uterus, uterine cervix, myometrium, ovary, fetal ovary, testis, fetal testis, and seminal vesicle. See DG expression data at World Wide Web at genecards.org/cgi-bin/carddisp.pl?gene=DAG1 and at proteomicsdb.org/proteomicsdb/#human/proteinDetails/Q14118/expression.

In other embodiments, an anti-DG antibody or antigen-binding fragment thereof can target a cell (a stem cell) with the unique ability to differentiate into specialized cell types in the body. Stem cells also proliferate indefinitely to produce additional stem cells (self-renew). Stem cells include embryonic stem cells, adult stem cells (such as hematopoietic stem cells, basal cells, and mesenchymal stem cells), and induced pluripotent stem cells. In some embodiments, an anti-DG antibody or antigen-binding fragment thereof can target a progenitor cell. A progenitor cell includes cells that are able to differentiate into specific cell types; however, a progenitor cell is already more differentiated in its development than a stem cell and does not proliferate indefinitely. Examples of progenitor cells include: satellite cells in muscle; intermediate progenitor cells formed in the subventricular zone of a vertebrate brain; bone marrow stromal cells that provide structural and physiological support for stem cells; cells in the periosteum (a dense layer of vascular connective tissue enveloping the bones except at the surfaces of the joints) that can differentiate into osteoblasts and chondroblasts; pancreatic progenitor cells; angioblasts; endothelial progenitor cells; blast cells; and hematopoietic progenitor cells.

In particular embodiments, an anti-DG antibody or antigen-binding fragment thereof can target cells of a cell line that expresses DG, such as the following cell lines that express DG: breast cancer (Hs-578T, MCF-7, MCF-7/adr, LCC2, HCC-1937, MFM-223, MDA-MB-453, BT-549, HMT-3522, T-47D, MDA-MB-231); breast/mammary epithelial (MCF-10A, HMEpC); cervical cancer (HeLa, HeLa S3); ovarian cancer (SKOV-3, OVCAR-4, OVCAR-8, OVCAR-8/ADR, IGROV-1, OVCAR-3); prostate cancer (LNCaP, PC-3, DU-145); colon cancer (SW-480, HT-29, RKO, Colo-205, HCT-15, SW-620, HCC-2998); gastrointestinal carcinoma (OVCAR-5); brain cancer (GaMG, U-251 MG, SNB-19, SNB-75, SF-539, SK-N-BE(2), SF-295, SF-268); lung cancer (NCI-H460, EKVX, HOP-92, NCI-H322M, A-549, NCI-H226, NCI-H23, HOP-62); kidney (HEK-293); kidney cancer (RXF-393, SN-12C, RCC 786-O); bone cancer (U2-OS); melanoma (A-375, MALME-3M, M14, SK-MEL-28, SK-MEL-2); liver cancer (Hep-G2, HuH-7); bladder cancer (MGHC3, UMUC3, UMUC5, UMUC9, UMUC10, UMUC11, and UMUC13); lymphoma (SR); T cell leukemia (JURKAT); myeloid leukemia (K562); and lymphoblastic leukemia (CCRF-CEM).

The present disclosure provides methods for collecting, optionally enriching for, and culturing cells prior to contacting the cells with an anti-DG antibody/payload of the disclosure and selecting for contacted cells that have internalized the anti-DG antibody/payload. The following describes exemplary methods for T cells and stem cells, but particular methods for collection, enrichment, and culture will depend upon the particular target cell(s), and appropriate methods would be known to one of skill in the art.

By way of example, T cells can be isolated from a sample such as blood or a blood-derived sample, an apheresis product, or a leukapheresis product. Exemplary samples include whole blood, peripheral blood mononuclear cells (PBMCs), leukocytes, bone marrow, thymus, cancer tissue, lymphoid tissue, spleen, or other appropriate sources. Isolation protocols for T cells include: flow activated cell sorting (FACS); density gradient centrifugation (e.g., Ficoll-Hypaque); immune precipitation by positive enrichment of T cells using one or more antibodies that binds to T cells; immune precipitation by negative depletion to deplete non-target cells (e.g., RosetteSep™, STEMCELL Technologies, Seattle, WA); immunomagnetic selection using antibody-immobilized magnetic beads to remove non T cells and enrich for T cells (e.g., EasySep™, STEMCELL Technologies, Seattle, WA); a microfluidic chip coated with anti-lymphocyte antibodies (Murthy et al., *Langmuir* 20:11649-11655, 2004); and a spiral microfluidic chip using different physical properties intrinsic to lymphocytes and other blood cells for separation (Chiu et al., *Scientific Reports* 9:8145, 2019).

Following isolation and/or enrichment, cells can be expanded to increase the number of cells. In particular embodiments, T cells can be activated and expanded before or after contacting with an anti-DG antibody/payload. For example, T cells can be activated by magnetic beads coated with anti-CD3/anti-CD28 monoclonal antibodies. Additional methods are described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and US 2006/0121005.

Cell culture media generally includes a buffer system, protein, trace elements, vitamins, inorganic salts, and energy sources. Culture media and conditions will be influenced by the particular target cell(s), and appropriate culture techniques, media, and conditions will be known to one of skill in the art. By way of example, there are many media to culture T cells, including RPMI 1640, X-VIVO 15 (Lonza, Inc., Basel, Switzerland), and CTS OpTimizer (ThermoFisher, Waltham, MA). In particular embodiments, the media may be supplemented with serum. In particular embodiments, the media may be supplemented with cytokines including IL-2, IL-4, IL-7, and/or IL-15.

Stem cells and progenitor cells can be isolated and enriched by one of skill in the art. For example, methods for isolation and enrichment of CD34+ and other cells are known in the art and disclosed for example in U.S. Pat. Nos. 4,965,204; 4,714,680; 5,061,620; 5,643,741; 5,677,136; 5,716,827; 5,750,397 and 5,759,793. In particular embodiments, CD34+ cells can be recovered from cord blood, bone marrow or from blood after mobilization by cytokines to cause movement of hematopoietic stem cells from the bone marrow space into the peripheral circulation.

Stem cells and progenitor cells can be selected by positive and negative selection techniques as described for T cells. In some embodiments, stem cells and progenitor cells can be selected using commercially available antibodies which bind to hematopoietic progenitor or stem cell surface antigens, e.g. CD34, using methods known to those of skill in the art. In some embodiments, negative selection can be utilized to select against substantially any desired cell marker.

Once progenitor or stem cells have been isolated, they may be propagated by growing in any suitable medium. For example, progenitor or stem cells can be grown in conditioned medium from stromal cells, such as those that can be obtained from bone marrow or liver associated with the secretion of factors, or in medium including cell surface factors supporting the proliferation of stem cells. In particular embodiments, purified progenitor or stem cells can be cultured in the presence of factors such as interleukin (IL)-3, thrombopoietin (TPO), stem cell factor (SCF), flt3 ligand (Flt-3L; the ligand of the flt3 gene product), or a combination thereof. It will be appreciated that other suitable cell culture and expansion methods can be used in accordance with the methods as well. Cells can also be grown in serum-free medium, as described in U.S. Pat. No. 5,945,337.

Representative assays to assess whether a cell contacted with an anti-DG antibody/payload has internalized the anti-DG antibody/payload are described herein. Where the payload includes a nucleic acid, methods are known in the art to select for cells that have internalized the nucleic acid. In particular embodiments, the nucleic acid encodes a selectable marker whose expression can be detected. Exemplary selectable markers include a fluorescent protein (e.g., green fluorescent protein, red fluorescent protein), a luminescent protein (e.g., firefly luciferase), a gene that confers resistance to an antibiotic (e.g. neomycin resistance gene), and a cell surface expressed protein (e.g., truncated epidermal growth factor receptor). In particular embodiments, a selectable marker can include a gene encoding a protein that confers resistance to blasticidin, geneticin, hygromycin B, puromycin, or zeocin.

(VI) BLADDER CANCER

Bladder cancer begins when healthy cells in the bladder lining, most commonly made up of urothelial cells, change and proliferate out of control. Urothelial cells also line the renal pelvis and ureters, and cancer that develops in these areas are called upper tract bladder cancer.

The three main types of bladder cancer include: urothelial carcinoma (UCC), squamous cell carcinoma, and adenocarcinoma. Urothelial carcinoma (or UCC), also known as transitional cell carcinoma (TCC), accounts for about 90% of all bladder cancers. In squamous cell carcinoma, squamous cells develop in the bladder lining in response to irritation and inflammation. Over time, these cells may become cancerous. Squamous cell carcinoma accounts for about 4% of all bladder cancers. Adenocarcinoma develops from glandular cells and accounts for about 2% of all bladder cancers.

Bladder cancer can also be described as noninvasive, non-muscle-invasive, or muscle-invasive. Noninvasive bladder cancer includes noninvasive papillary carcinoma and carcinoma in situ (CIS). Noninvasive papillary carcinoma includes a growth found on a small section of tissue that is easily removed and is considered stage 0a (stages of bladder cancer are further described below). CIS, or noninvasive flat carcinoma, is found only on or near the surface of the bladder and is considered stage 0is. Non-muscle-invasive bladder cancer typically has only grown into the lamina propria (the connective tissue that separates the lining of the bladder from the muscles beneath) and not into muscle and is considered stage I, although this type can spread into the bladder muscle or to other parts of the body. Muscle-invasive bladder cancer has grown into the bladder's wall muscle and sometimes into the fatty layers or surrounding tissue outside the bladder. All cell types of bladder cancer can metastasize.

The stage of bladder cancer can be determined based on examining the sample removed during a transurethral resection of bladder tumor (TURBT), a biopsy procedure.

A TNM (tumor, node, metastasis) staging system can be used to describe the stage of a cancer. The system takes into consideration factors including: the size and location of a primary tumor; whether the tumor has spread to the lymph nodes, and locations and numbers of tumors if spread has occurred; and whether metastasis has occurred, and locations and numbers of tumors if metastasis has occurred.

Bladder cancer can include 5 stages: stage 0 (zero) and stages I through IV (1 through 4). Staging can be clinical or pathological. Clinical staging is based on the results of tests done before surgery, while pathological staging is based on what is found during surgery. Tests can include physical examinations, imaging scans, and biopsies, and their results can represent the pathology of disease. Stages may also be divided into smaller groups that help describe the tumor in even more detail. A lowercase letter "in" (multiple) is indicated if there is more than one tumor. A lowercase "c" means that the tumor was staged clinically, while a lowercase "p" means that the tumor was staged pathologically.

Table 2 summarizes the TNM staging system for bladder cancer and upper tract bladder cancer (renal pelvis and ureters). Further details on bladder cancer stages are provided below.

TABLE 2

| TNM staging system for bladder cancer and upper tract bladder cancer | | |
|---|---|---|
| Size and Location of Tumor | Bladder cancer | Upper tract bladder cancer (renal pelvis and ureters) |
| Tumor^ | | |
| TX | The primary tumor cannot be evaluated. | The primary tumor cannot be evaluated. |
| T0 | There is no evidence of a primary tumor in the bladder. | There is no evidence of a primary tumor in the bladder. |
| Ta | noninvasive papillary carcinoma | noninvasive papillary carcinoma |
| Tis | carcinoma in situ (CIS) | carcinoma in situ (CIS) |
| T1 | The tumor has spread to the connective tissue that separates the lining of the bladder from the muscles beneath (the lamina propria), but it has not spread to the bladder wall muscle. | The tumor has spread to the connective tissue beneath the lining of the renal pelvis or ureter. |
| T2 | The tumor has spread to the muscle of the bladder wall. | The tumor has spread to the muscle. |
| T2a | The tumor has spread to the inner half of the bladder wall muscle (the superficial muscle). | |
| T2b | The tumor has spread to the outer half of the bladder wall muscle (the deep muscle). | |
| T3 | The tumor has grown into the perivesical tissue (the fatty tissue that surrounds the bladder). | The tumor has grown into the peripelvic fat (layers of fat around the kidney), into the renal parenchyma (the part of the kidney that filters blood and makes urine), or into the fat around the ureter. |
| T3a | The tumor has grown into the perivesical tissue, as seen through a microscope. | |
| T3b | The tumor has grown into the perivesical tissue macroscopically, i.e., is large enough to be seen during imaging tests or to be seen or felt by the doctor. | |
| T4 | The tumor has spread to any of the following: the abdominal wall, the pelvic wall, prostate or seminal vesicle, uterus or vagina. | The tumor has spread to nearby organs or into the outer layer of fat on the kidney. |
| T4a | The tumor has spread to the prostate, seminal vesicles, uterus, or vagina. | |
| T4b | The tumor has spread to the pelvic wall or the abdominal wall. | |
| Node* | | |
| NX | The regional lymph nodes cannot be evaluated. | The regional lymph nodes cannot be evaluated. |
| N0 | The cancer has not spread to the regional lymph nodes. | The cancer has not spread to the regional lymph nodes. |
| N1 | The cancer has spread to a single regional lymph node in the pelvis. | The cancer is 2 centimeters (cm) or smaller in a single lymph node. |
| N2 | The cancer has spread to 2 or more regional lymph nodes in the pelvis. | The cancer is larger than 2 cm in a single lymph node, or it has spread to more than 1 lymph node. |
| N3 | The cancer has spread to the common iliac lymph nodes, which are located behind the major arteries in the pelvis, above the bladder. | |
| Metastasis† | | |
| M0 | The disease has not metastasized. | The disease has not metastasized. |
| M1 | There is distant metastasis. | There is distant metastasis. |

TABLE 2-continued

TNM staging system for bladder cancer and upper tract bladder cancer

| Size and Location of Tumor | Bladder cancer | Upper tract bladder cancer (renal pelvis and ureters) |
|---|---|---|
| M1a | The cancer has spread only to lymph nodes outside of the pelvis. | |
| M1b | The cancer has spread other parts of the body. | |

^According to the TNM (Tumor, Node, Metastasis) system, the "T" plus a letter and/or number (0 to 4) is used to describe the size and location of the tumor.
*Regional lymph nodes are near where the cancer starts, within the true pelvis (hypogastric, obturator, iliac, perivesical, pelvic, sacral, and presacral lymph nodes). Lymph nodes in other parts of the body are called distant lymph nodes.
†Describes whether the cancer has spread to other parts of the body (distant metastasis). Adpated from Cancer.net.

Stage 0a in bladder cancer includes an early cancer that is only found on the surface of the inner lining of the bladder and has not invaded the muscle or connective tissue of the bladder wall. Cancer cells are grouped together and can often be easily removed. In particular embodiments, stage 0a bladder cancer can be noninvasive papillary urothelial carcinoma (Ta, N0, M0).

Stage 0is in bladder cancer includes cancer found only on the inner lining of the bladder. It has not grown in toward the hollow part of the bladder, and it has not spread to the thick layer of muscle or connective tissue of the bladder. In particular embodiments, stage 0is bladder cancer can be a flat tumor or carcinoma in situ (CIS) (Tis, N0, M0). In particular embodiments, stage 0is bladder cancer is considered an aggressive, high-grade cancer because it can often lead to muscle-invasive disease.

Stage I in bladder cancer includes cancer that has grown through the inner lining of the bladder and into the lamina propria but has not spread to the thick layer of muscle in the bladder wall or to lymph nodes or other organs. In particular embodiments, stage I bladder cancer can be T1, N0, M0.

Stage II in bladder cancer includes cancer that has spread into the thick muscle wall of the bladder, but the tumor(s) has not reached the fatty tissue surrounding the bladder and has not spread to the lymph nodes or other organs. It is also called invasive cancer or muscle-invasive cancer. In particular embodiments, stage II bladder cancer can be T2, N0, M0.

Stage III in bladder cancer includes cancer that has spread throughout the muscle wall to the fatty layer of tissue surrounding the bladder (perivesical tissue), to the prostate, or to the uterus or vagina. In particular embodiments, stage III bladder cancer has spread to the regional lymph nodes.

Stage IIIA in bladder cancer includes cancer that has grown into the perivesical tissue or has spread to the prostate, uterus, or vagina, but has not spread to the lymph nodes or other organs (T3a, T3b, or T4a; N0; M0), or the cancer has spread to a single regional lymph node (T1 to T4a, N1, M0).

Stage IIIB in bladder cancer includes cancer that has spread to 2 or more regional lymph nodes or to the common iliac lymph nodes (T1 to T4a, N2 or N3, M0).

Stage IV in bladder cancer includes cancer that has spread into the pelvic wall or abdominal wall, or the cancer has spread to lymph nodes outside of the pelvis or to other parts of the body.

Stage IVA in bladder cancer includes cancer that has spread to the pelvic wall or the abdominal wall but not to other parts of the body (T4b, any N, M0), or the cancer has spread to lymph nodes located outside of the pelvis (any T, any N, M1a).

Stage IVB in bladder cancer includes cancer that has spread to other parts of the body (any T, any N, M1b).

Stage 0a in upper tract bladder cancer includes an early cancer that is only found on the surface of the inner lining of the renal pelvis or ureter. Cancer cells are grouped together and can often be easily removed. In particular embodiments, stage 0a upper tract bladder cancer can be noninvasive papillary urothelial carcinoma (Ta, N0, M0).

Stage 0is in upper tract bladder cancer is found only on the inner lining of the renal pelvis or ureter. In particular embodiments, stage 0is upper tract bladder cancer can be a flat tumor or carcinoma in situ (CIS) (Tis, N0, M0).

Stage I in upper tract bladder cancer includes cancer that has grown into the inner lining of the renal pelvis or ureter but has not spread to the lymph nodes or other parts of the body. In particular embodiments, stage I upper tract bladder cancer can be T1, N0, M0.

Stage II in upper tract bladder cancer includes cancer that has grown into the muscle behind the inner lining of the renal pelvis or ureter. The cancer has not spread to the lymph nodes or other parts of the body. In particular embodiments, stage II upper tract bladder cancer can be T2, N0, M0.

Stage III in upper tract bladder cancer includes cancer that has grown past the muscle and into the fat surrounding the kidney or ureter or into the renal parenchyma. The cancer has not spread to the lymph nodes or other parts of the body. In particular embodiments, stage III upper tract bladder cancer can be T3, N0, M0.

Stage IV in upper tract bladder cancer includes cancer that has invaded nearby organs or to the outer layer of fat of the kidney (T4, NX or N0, M0), or the cancer involves the lymph nodes (any T, N1 or N2, M0), or there is distant metastasis (any T, any N, M1).

In particular embodiments, compositions and methods of the present disclosure are provided to diagnose, monitor, and treat early stage bladder cancer. In this context, early stage bladder cancer includes: urothelial carcinoma (UCC); squamous cell carcinoma; adenocarcinoma; noninvasive bladder cancer; noninvasive upper tract bladder cancer; non-muscle-invasive bladder cancer; non-muscle-invasive upper tract bladder cancer; stage 0a bladder cancer; stage 0a upper tract bladder cancer; noninvasive papillary urothelial carcinoma (Ta, N0, M0) of the bladder; noninvasive papillary urothelial carcinoma (Ta, N0, M0) of the upper tract of the bladder; a flat tumor or carcinoma in situ (CIS) (Tis, N0, M0) of the bladder; a flat tumor or carcinoma in situ (CIS) (Tis, N0, M0) of the upper tract of the bladder; stage I bladder cancer (T1, N0, M0); stage I upper tract bladder cancer (T1, N0, M0); an early stage micropapillary urothelial carcinoma (MPUC) (T3 or lower, N0, M0) of the bladder; and a micropapillary urothelial carcinoma (MPUC) (T3 or lower, N0, M0) of the upper tract of the bladder.

(VII) ASSAYS AND MODELS TO CHARACTERIZE ANTI-DG ANTIBODIES

Antibodies of the present disclosure can be tested using in vitro, ex vivo, and in vivo assays known in the art.

In particular embodiments, activity of anti-DG antibodies of the present disclosure can be assessed by measuring antibody binding to the surface of living cells expressing the human DG protein. In particular embodiments, an assay can include the following steps. Positive cell populations expressing human DG protein and negative control cell populations not expressing human DG protein can be co-cultured in wells of micro-plates, incubated with an anti-DG antibody for 60 min, washed after anti-DG antibody incubation, and incubated with a labeled secondary antibody that binds to the anti-DG antibody. The cells labeled with secondary antibody can be washed, fixed with formalin, stained with nuclei staining reagent (e.g., DAPI), and visualized for antibody binding and nuclei staining. In particular embodiments, cells are not fixed in formalin for live cell imaging. In particular embodiments, anti-DG antibodies are considered to have good activity if they demonstrate selective staining of positive (human DG-expressing) cells and little or no staining of negative control cells. In particular embodiments, cells expressing the human DG protein can come from: cell lines including a murine MEpG cell line and its variants (Weir et al. J. Cell Sci., 119(19): 4047-58, 2006); normal human bladder cell lines; human breast cancer cell lines including MDA-MB-231 (low level of α-DG glycosylation) and T47D (high level of α-DG glycosylation); and human bladder cancer cell lines including MGHC3, UMUC3, UMUC5, UMUC9, UMUC10, UMUC11, and UMUC13. In particular embodiments, a negative control includes cells from a cell line that does not express human DG protein, including murine MEpG line expressing green fluorescent protein (GFP) and not the human DG protein, created as previously described in Oppizzi et al., *Traffic*, 9(12): 2063-72, 2008. In particular embodiments, a negative control includes use of a labeled secondary antibody alone, omitting the primary anti-DG antibody.

In particular embodiments, internalization of antibodies (bound to DG) into endocytic vesicles of living cells can be assessed by incubating antibodies with cells in culture for longer times (e.g., 2 to 4 hours longer) prior to fixation in formalin or live cell imaging. With longer incubation times, the bound antibodies have an extended opportunity to enter the endocytic pathway and accumulate in endocytic vesicles. In particular embodiments, internalization of antibodies into endocytic vesicles is recognizable as the accumulation of discrete fluorescent foci in the cellular cytoplasm that is excluded from the nucleus. In particular embodiments, these foci are observed to be highly mobile and rapidly move about the cell cytoplasm, as is characteristic of endocytic vesicles, with live cell imaging.

In particular embodiments, antibody recognition of DG can be assessed by immunoprecipitation studies. DG is present on the cell surface as a non-covalently bound heterodimer composed of the transmembrane β-DG subunit and the extracellular α-DG subunit. In particular embodiments, the β-DG appears at a mass of 42 kDa and the α-DG subunit appears at a broad mass range of 100 kDa to 180 kDa. In particular embodiments, cell surface biotinylation and immunoprecipitation methods follow protocols as reported in Singh et al., (Cancer Res., 64(17):6152-6159, 2004). Cells can be cultured and then incubated with NHS-PEO$_4$-biotin (e.g., for 30 min at room temperature). Subsequently, cells can be washed with PBS and then lysed in immunoprecipitation buffer (e.g., 50 mM Tris-HCl (pH 7.4), 100 mM NaCl, 0.1% (v/v) Nonidet P-40, 1 mM dithiothreitol, 1 mM phenylmethylsulfonyl fluoride, and protease inhibitor mixture). Cleared lysate can be incubated with monoclonal antibodies (e.g., overnight at 4° C.), followed by the addition of protein A/G-agarose beads and a further incubation (e.g., for 3 hours with continuous rocking at 4° C.). The beads can subsequently be washed, directly resuspended in protein gel sample buffer, boiled, and processed for SDS-PAGE and immunoblotting for proteins conjugated with biotin using HRP-conjugated streptavidin. The signals can be imaged by chemiluminescence. In particular embodiments, cells that can be used in immunoprecipitation studies include: murine MEpG cells expressing human DG (Weir et al., *J. Cell Sci.* 119(19): 4047-58, 2006); normal human bladder cells; human breast cancer cells from lines including MDA-MB-231 and T47D; and human bladder cancer cells from lines including MGHC3, UMUC3, UMUC5, UMUC9, UMUC10, UMUC11, and UMUC13.

In particular embodiments, antibody recognition of DG and/or DG localization can be assessed by immunostaining of tissue sections. DG has been shown to be localized to the basolateral surface of epithelial cell layers. In particular embodiments, adjacent sections of formalin fixed and paraffin embedded (FFPE) human bladder tissue can be stained by Hematoxylin and Eosin (H&E) using standard histochemical methods or immunostained for DG using standard immunochemical methods. In particular embodiments, immunostaining can be performed by tissue de-paraffinization in xylene, followed by re-hydration, pressure cooker for 30 minutes in DAKO buffer (PH 8.0), and blocked in blocking buffer for 1 hour. An anti-DG antibody can be diluted into blocking buffer and incubated on the slide overnight at 4° C. The slide can subsequently be washed with PBS, incubated with a fluorescently labeled secondary antibody, and mounted under a glass coverslip in mounting medium containing DAPI. The slide can be imaged on a slide scanner. In particular embodiments, immunostaining can be performed on normal human bladder tissue or human bladder carcinoma tissue.

In particular embodiments, anti-DG antibody function can be assessed by molecular imaging of bladder cancer tissue ex vivo as described by Pan et al. (*Sci Transl. Med.*, 6(260): 148, 2014). In particular embodiments, the disclosed anti-DG antibodies can be labeled with a fluorescent tag such as a quantum dot. Radical cystectomy can be performed to obtain an intact bladder. After radical cystectomy, an ex vivo intact bladder can be instilled with a fluorescently labeled anti-DG antibody via a urinary catheter. The fluorescently labeled anti-DG antibody can be incubated (e.g., for 30 min) to allow antibody binding. The labeled bladder can be irrigated with saline and any bound anti-DG antibody can be detected by endoscopic imaging of the bladder mucosa. Normal and suspicious regions can be biopsied for histopathological analysis.

Each antibody or antigen-binding fragment thereof showing selective cancer targeting activity in the initial testing can be further studied to determine optimal targeting conditions. Recombinant versions of each antibody or antigen-binding fragment thereof can be generated and tested with the goal of optimizing large scale production as well as effectiveness.

The most effective antibodies or antigen-binding fragments thereof identified through in vitro assays, ex vivo assays, and/or imaging assays can be coupled to a cytotoxin or other therapeutic compound and applied in intravesicular treatment of bladder cancers in an animal model. In particular embodiments, pre-clinical testing in animals allow rapid advancement of candidate anti-DG antibodies or antigen-binding fragments thereof into clinical trials for imaging and treatment.

Preclinical testing of the antibodies or antigen-binding fragments thereof described herein can be performed in an animal model of bladder cancer where normal tissue architecture remains intact, and cancers are focal in origin. In particular embodiments, animal cancer models can be used to test antibody compositions for selective targeting of bladder cancer cells in vivo. In particular embodiments, in vivo or ex vivo testing of antibody binding and internalization in the bladder can be assessed by fluorescence or positron emission tomography (PET) imaging, or through biodistribution of radiolabeled antibodies following necropsy.

Although mouse bladder cancer models exist, the antibodies or antigen-binding fragments thereof described herein do not bind to mouse or dog DG (MDCK cells) but do bind to Rhesus monkey and human cells. Consequently, in particular embodiments, in vivo testing of the disclosed antibodies can be performed in humans, monkeys, and/or pigs. In particular embodiments, antibody testing can be performed in the bladder of living non-human primates (NHP; e.g., monkeys) with or without bladder cancer or pre-cancerous lesions. These studies can include intravesicular exposure to a labeled antibody, followed by imaging. In particular embodiments, the antibodies or antigen-binding fragments thereof described herein can be conjugated to a fluorophore or to a positron-emitting radioligand, then instilled into the bladder by catheterization. Internalization of labeled antibodies or antigen-binding fragments thereof can be assessed by any method known of one of ordinary skill in the art and described in the present disclosure. Examples of such methods include visual assessment by fluorescence microscopy or PET imaging and quantitative assessment by flow cytometry. In particular embodiments, the non-human primates, such as monkeys, can be euthanized and bladders removed to test for the selective incorporation of the labeled antibodies or antigen-binding fragments into bladder cancer cells. In particular embodiments, antibody testing can be performed in a clinical trial, such as, a phase 0 study in human bladder cancer patients, with assessment of antibodies by fluorescence detection or PET imaging. In particular embodiments, the labeled antibodies or antigen-binding fragments thereof are internalized at high levels in the carcinoma cells of the bladder and at undetectable levels in normal bladder epithelium.

(VIII) CONTROLS AND TEST SAMPLES

Particular embodiments of the present disclosure provide for a reference level that is derived from values obtained from a population of control cells and/or samples. Reference levels can include "normal" or "control" levels or values, defined according to, e.g., discrimination limits or risk defining thresholds, in order to define cut-off points and/or abnormal values for subjects having a disorder associated with loss of apical-basal polarity in epithelial cells (e.g., bladder cancer). The reference level then is the DG protein level typically found in a subject not afflicted by a disorder associated with loss of apical-basal polarity in epithelial cells (e.g., bladder cancer). Other terms for "reference levels" include "index," "baseline", "standard", "healthy", "afflicted", etc. Such normal levels can vary, based on whether a DG protein level is used alone or in a formula combined with other indications of a disorder associated with loss of apical-basal polarity in epithelial cells to output a score. Alternatively, the reference level can be a database of DG protein levels from previously tested subjects who were identified as not having a disorder associated with loss of apical-basal polarity in epithelial cells (e.g., bladder cancer). Reference levels can also be derived from, e.g., a control subject or population whose diagnosis regarding a disorder associated with loss of apical-basal polarity in epithelial cells (e.g., bladder cancer) is known. In some embodiments, the reference value can be derived from one or more subjects who are at risk of a disorder associated with loss of apical-basal polarity in epithelial cells (e.g., bladder cancer), or from subjects who have shown improvements in DG protein levels as a result of exposure to a treatment for a disorder associated with loss of apical-basal polarity in epithelial cells (e.g., bladder cancer). In particular embodiments, the reference level can be derived from one or more subjects who have not been exposed to treatment for a disorder associated with loss of apical-basal polarity in epithelial cells (e.g., bladder cancer). A reference level can also be derived from disease activity algorithms or computed indices from population studies.

In particular embodiments, "reference level" can refer to a standardized value for an DG protein level which represents a level indicative of a disorder associated with loss of apical-basal polarity in epithelial cells (e.g., bladder cancer); a level associated with a mild form of a disorder associated with loss of apical-basal polarity in epithelial cells (e.g., bladder cancer); or a level associated with a severe form of a disorder associated with loss of apical-basal polarity in epithelial cells (e.g., bladder cancer). The reference level can be a universal reference level which is useful across a variety of testing locations. In some embodiments, the reference level or reference signal is derived from normal cells having apical-basal polarity that are adjacent to/found in the same tissue as the cells exhibiting a loss of apical-basal polarity. In particular embodiments, the reference level and/or reference weighted score is derived from (i) an individual who does not have a disorder associated with loss of apical-basal polarity in epithelial cells (e.g., bladder cancer); (ii) a group of individuals who do not have a disorder associated with loss of apical-basal polarity in epithelial cells (e.g., bladder cancer); (iii) a subject before diagnosis with a disorder associated with loss of apical-basal polarity in epithelial cells (e.g., bladder cancer); or (iv) a subject at the time of diagnosis, at the beginning of a treatment regimen for a disorder associated with loss of apical-basal polarity in epithelial cells (e.g., bladder cancer), or at particular time points during a treatment. Reference levels for a subject can also be related to time points of a subject not undergoing treatments for a disorder associated with loss of apical-basal polarity in epithelial cells (e.g., bladder cancer) to monitor the natural progression or regression of the disorder.

In particular embodiments, a control sample includes a population of control cells. In particular embodiments, a control sample can be derived from a healthy subject. A healthy subject can include a subject who does not have a disorder associated with loss of apical-basal polarity in epithelial cells, who does not have bladder cancer, and/or who has no known cancers. In particular embodiments, control cells can include cells that have apical-basal polarity.

In particular embodiments, control cells can include cells that have lost apical-basal polarity.

In particular embodiments, a test sample can include cells derived from a subject: suspected of having or who has bladder cancer; whose bladder cancer status is unknown; who has a disorder associated with loss of apical-basal polarity in epithelial cells; or who does not have a disorder associated with loss of apical-basal polarity in epithelial cells.

Quantification of DG protein level in a subject or test sample can be relative or absolute. An index, ratio, percentage or any other indication of the level or amount, or presence or absence, of DG protein in a subject or test sample can be measured, for example, relative to a reference level. Conclusions can be drawn based on whether a subject or sample value is statistically significantly different or not statistically significantly different from a reference level. A measure is not statistically significantly different if the difference is within a level that would be expected to occur based on chance alone. In contrast, a statistically significant difference or increase is one that is greater than what would be expected to occur by chance alone. Statistical significance or lack thereof can be determined by any of various methods well-known in the art. Examples of commonly used measures of statistical significance include the t-test, the p-value, and other tests described herein. The p-value represents the probability of obtaining a given result equivalent to a particular datapoint, where the datapoint is the result of random chance alone. A result is often considered significant (not random chance) at a p-value less than or equal to 0.05.

(IX) COMPOSITIONS

The antibodies or antigen-binding fragments thereof disclosed herein can be formulated into compositions for direct administration to a subject. In particular embodiments, more than one antibody or antigen-binding fragment thereof disclosed herein can be administered to the same subject in concert, whether sequentially or simultaneously. In particular embodiments, a composition includes an antibody or antigen-binding fragment thereof attached to a payload. In particular embodiments, the payload is attached directly or indirectly to the antibody or antigen-binding fragment thereof. In particular embodiments, the payload includes a detectable agent and/or a biologically functional molecule. In particular embodiments, the payload includes one or more of a fluorescent tag, a bioluminescent tag, a chemiluminescent tag, a nucleic acid, a nucleic acid barcode, an affinity tag, an enzyme, a radioisotope, a magnetic resonance imaging contrast agent, a toxin, a nanoparticle, a nanoparticle including a nucleic acid, an mRNA, an siRNA, and/or a small molecule drug.

The compositions disclosed herein can be formulated for administration by injection, inhalation, infusion, perfusion, lavage, or ingestion. The compositions disclosed herein can further be formulated for infusion via catheter, intravenous, intramuscular, intratumoral, intradermal, intraarterial, intranodal, intralymphatic, intraperitoneal, intralesional, intraprostatic, intravaginal, intrarectal, topical, intrathecal, intraparenchymal, intravesicular, intracerebroventricular, subpial, intravitreal, subretinal, transgastric, transduodenal, intracystic, bronchoscopic, aerosol, direct injection into ligament or tendon, oral and/or subcutaneous administration. In particular embodiments, administration is intravesicular. In particular embodiments, intravesicular administration refers to administrating directly into the bladder through a urinary catheter. The urinary catheter is inserted through the urethra (the tube which carries urine from the bladder to the outside of the body). A formulation of the present disclosure can be injected into the catheter, which is then clamped. Clamping the catheter allows the formulation to remain in the bladder. The patient can be encouraged to roll from side to side and to lie on their backs to help the medication reach all areas of the bladder. After a predetermined time (e.g., 1 to 2 hours) the catheter is unclamped and the fluid is drained. The catheter is then removed. In particular embodiments, intravesicular administration is an outpatient procedure.

For injection and infusion, compositions can be formulated as aqueous solutions, such as in buffers including Hanks' solution, Ringer's solution, or physiological saline. The aqueous solutions can contain formulatory agents such as suspending, stabilizing and/or dispersing agents. Alternatively, the formulation can be in lyophilized and/or powder form for constitution with a suitable vehicle, e.g., sterile pyrogen-free water, before use.

Any composition or formulation disclosed herein can advantageously include any other pharmaceutically acceptable carriers which include those that do not produce significantly adverse, allergic, or other untoward reactions that outweigh the benefit of administration, whether for research, prophylactic and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety and purity standards as required by United States FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants. In particular embodiments, a pharmaceutically acceptable carrier includes buffered saline. Buffered saline can include exemplary buffering agents described herein.

Exemplary buffering agents include citrate buffers, succinate buffers, malate buffers, tartrate buffers, fumarate buffers, gluconate buffers, aspartate buffers, glutamate buffers, α-ketoglutarate buffers, oxalate buffers, lactate buffers, acetate buffers, phosphate buffers, histidine buffers and/or trimethylamine salts.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol and 3-pentanol.

Exemplary isotonic agents include polyhydric sugar alcohols including trihydric or higher sugar alcohols, such as glycerin, erythritol, arabitol, xylitol, sorbitol, or mannitol.

Exemplary stabilizers include organic sugars, polyhydric sugar alcohols, polyethylene glycol; sulfur-containing reducing agents, amino acids, low molecular weight polypeptides, proteins, immunoglobulins, hydrophilic polymers, or polysaccharides.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as sparingly soluble salts.

Additionally, compositions can be formulated as sustained-release systems utilizing semipermeable matrices of solid polymers containing at least one active ingredient. Various sustained-release materials have been established and are well known by those of ordinary skill in the art. Sustained-release systems may, depending on their chemical nature, release active ingredients following administration for two weeks to 1 month. In particular embodiments, a sustained-release system could be utilized, for example, if a human patient were to miss a weekly administration.

(X) METHODS OF USE

The formulations disclosed herein can be used for treating subjects (humans, veterinary animals (dogs, cats, reptiles, birds, etc.), livestock (horses, cattle, goats, pigs, chickens, etc.), and research animals (monkeys, rats, mice, fish, etc.). In particular embodiments, a subject is a human patient having or suspected of having a disease characterized at least in part by the loss of apical-basal polarity in epithelial cells. Treating subjects includes delivering therapeutically effective amounts. Therapeutically effective amounts include those that provide effective amounts, prophylactic treatments, and/or therapeutic treatments.

An "effective amount" is the amount of a pharmaceutical composition including an anti-DG antibody or antigen-binding fragment thereof attached to a payload that is sufficient to generate a desired response, such as slowing the growth of a cancer cell. Effective amounts are often administered for research purposes.

A "prophylactic treatment" includes a treatment administered to a subject who does not display signs or symptoms of a condition to be treated or displays only early signs or symptoms of the condition to be treated such that treatment is administered for the purpose of diminishing, preventing, or decreasing the risk of developing the condition. Thus, a prophylactic treatment functions as a preventative treatment against a condition. In particular embodiments, a prophylactic treatment reduces the amount of epithelial cells that have lost apical-basal polarity in a subject. Determination of whether epithelial cells have lost apical-basal polarity can be determined by methods described herein. In particular embodiments, a prophylactic treatment reduces the risk of developing early stage bladder cancer.

A "therapeutic treatment" includes a treatment administered to a subject who displays symptoms or signs of a condition and is administered to the subject for the purpose of reducing the severity or progression of the condition. In particular embodiments, a therapeutic treatment reduces the amount of epithelial cells that have lost apical-basal polarity in a subject. Determination of whether epithelial cells have lost apical-basal polarity can be determined by methods described herein. In particular embodiments, a therapeutic treatment reduces tumor growth or size. In particular embodiments, a therapeutic treatment prevents or reduces tumor growth or size in early stage bladder cancer. In particular embodiments, DG-interacting antibodies described herein may be used to deliver chemotherapeutic agents to kill cancer cells.

Cancer can include a disease or condition in which abnormal cells divide without control and are able to invade other tissues. Cancer cells spread to other body parts through the blood and lymphatic systems. Cancer is a term for many diseases. There are more than 100 different types of cancer in humans. Most cancers are named after the organ in which they originate. For instance, a cancer that begins in the bladder may be called a bladder cancer. However, the characteristics of a cancer, especially with regard to the sensitivity of the cancer to therapeutic compounds, are not limited to the organ in which the cancer originates. A cancer cell is any cell derived from any cancer, whether in vitro or in vivo.

In particular embodiments, cancer is a malignant tumor characterized by abnormal or uncontrolled cell growth. The "pathology" of cancer includes all phenomena that compromise the well-being of the subject. This includes abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc. "Metastatic disease" or "metastasis" refers to cancer cells that have left the original tumor site and have migrated to other parts of the body, for example, via the bloodstream or lymph system.

Most carcinomas (cancers of epithelial origin) are characterized by the loss of apical-basal polarity that arises during cancer progression. Such carcinomas can include lung cancers, breast cancers, skin cancers (such as actinic keratosis which leads to squamous cell carcinomas) bladder cancers, and colon cancers, among others (Liu & Chen, *J Cancer Res Ther* Suppl 2, S80-S85, 2013; Hinck & Nathke, *Curr Opin Cell Biol* 26, 87-95, 2014; and Nese et al., *J Natl Compr Canc Netw* 7, 48-67, 2009).

The actual dose and amount of compositions, including antibodies or antigen-binding fragments thereof described herein, administered to a particular subject can be determined by a physician, veterinarian, or researcher taking into account parameters such as physical and physiological factors including target; body weight; type of condition; severity of condition; upcoming relevant events, when known; previous or concurrent therapeutic interventions; idiopathy of the subject; and route of administration, for example. In addition, in vitro and in vivo assays can optionally be employed to help identify optimal dosage ranges.

Therapeutically effective amounts of compositions described herein to administer can include doses ranging from, for example, 0.5 mg/kg to 25 mg/kg, or 1 mg/kg to 20 mg/kg. In particular embodiments, doses can include 0.5 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 5.5 mg/kg, 6 mg/kg, 6.5 mg/kg, 7 mg/kg, 7.5 mg/kg, 8 mg/kg, 8.5 mg/kg, 9 mg/kg, 9.5 mg/kg, 10 mg/kg, 10.5 mg/kg, 11 mg/kg, 11.5 mg/kg, 12 mg/kg, 12.5 mg/kg, 13 mg/kg, 13.5 mg/kg, 14 mg/kg, 14.5 mg/kg, 15 mg/kg, 15.5 mg/kg, 16 mg/kg, 16.5 mg/kg, 17 mg/kg, 17.5 mg/kg, 18 mg/kg, 18.5 mg/kg, 19 mg/kg, 19.5 mg/kg, 20 mg/kg, or greater. In particular embodiments, doses can include 50 mg/m² to 1000 mg/m², or 100 mg/m² to 800 mg/m². In particular embodiments, doses can include 50 mg/m², 100 mg/m², 150 mg/m², 200 mg/m², 250 mg/m², 300 mg/m², 350 mg/m², 400 mg/m², 450 mg/m², 500 mg/m², 550 mg/m², 600 mg/m², 650 mg/m², 700 mg/m², 750 mg/m², 800 mg/m², or greater. In particular embodiments, doses can include 0.5 mg/bladder instillation, 1 mg/bladder instillation, 5 mg/bladder instillation, 10 mg/bladder instillation, 15 mg/bladder instillation, 20 mg/bladder instillation, 25 mg/bladder instillation, 30 mg/bladder instillation, or greater.

Therapeutically effective amounts can be administered through any appropriate administration route such as by injection, infusion, lavage, and more particularly by administration intravesicularly.

Particular embodiments provide methods of treating a disorder. In particular embodiments, the disorder is associated with loss of apical-basal polarity in epithelial cells in a subject in need thereof, including administering to the subject a therapeutically effective amount of at least one antibody or antigen-binding fragment thereof including: (A) a heavy chain including CDRH1 shown in SEQ ID NO: 1, CDRH2 shown in SEQ ID NO: 2, and CDRH3 shown in SEQ ID NO: 3; and a light chain including CDRL1 shown in SEQ ID NO: 4, CDRL2 shown in SEQ ID NO: 5, and CDRL3 shown in SEQ ID NO: 6; or (B) a heavy chain including CDRH1 shown in SEQ ID NO: 11, CDRH2 shown in SEQ ID NO: 12, and CDRH3 shown in SEQ ID NO: 13; and a light chain including CDRL1 shown in SEQ ID NO: 14, CDRL2 shown in SEQ ID NO: 15, and CDRL3 shown in SEQ ID NO: 16; or (C) a heavy chain including CDRH1 shown in SEQ ID NO: 21, CDRH2 shown in SEQ ID NO: 22, and CDRH3 shown in SEQ ID NO: 23; and a light chain including CDRL1 shown in SEQ ID NO: 24, CDRL2 shown in SEQ ID NO: 25, and CDRL3 shown in SEQ ID NO: 26, attached to one or more payloads including a therapeutic agent. Particular embodiments provide administering the at least one antibody or antigen-binding fragment thereof to the subject, and subsequently administering to the subject a therapeutically effective amount of one or more payloads including a therapeutic agent. In particular embodiments, the one or more payloads bind the at least one antibody or antigen-binding fragment thereof in vivo after the administering of the one or more payloads. In particular embodiments, the one or more payloads bind covalently or non-covalently to the at least one antibody or antigen-binding fragment thereof. In particular embodiments, the covalent binding of the one or more payloads to the at least one antibody or antigen-binding fragment thereof occurs by a Diels-Alder reaction. In particular embodiments, the non-covalent binding of the one or more payloads to the at least one antibody or antigen-binding fragment thereof occurs through an affinity tag (e.g., a streptavidin, an avidin, or a biotin tag). In particular embodiments, the disorder includes oral cancers, esophageal cancers, stomach cancers, pancreatic cancers, lung cancers, breast cancers, skin cancers, colon cancers, uterine cancers, fallopian tube cancers, and bladder cancers. In particular embodiments, the disorder is a pancreatic cyst. In particular embodiments, the disorder is early stage bladder cancer and the administering is intravesicularly. In particular embodiments, the early stage bladder cancer is an early stage micropapillary urothelial carcinoma (MPUC) of the bladder or an MPUC of the upper tract of the bladder.

Particular embodiments provide methods of diagnosing, determining efficacy of a treatment for, and/or monitoring a disorder associated with loss of apical-basal polarity in epithelial cells in a subject, including delivering into the subject at least one antibody or antigen-binding fragment thereof including: (A) a heavy chain including CDRH1 shown in SEQ ID NO: 1, CDRH2 shown in SEQ ID NO: 2, and CDRH3 shown in SEQ ID NO: 3; and a light chain including CDRL1 shown in SEQ ID NO: 4, CDRL2 shown in SEQ ID NO: 5, and CDRL3 shown in SEQ ID NO: 6; or (B) a heavy chain including CDRH1 shown in SEQ ID NO: 11, CDRH2 shown in SEQ ID NO: 12, and CDRH3 shown in SEQ ID NO: 13; and a light chain including CDRL1 shown in SEQ ID NO: 14, CDRL2 shown in SEQ ID NO: 15, and CDRL3 shown in SEQ ID NO: 16; or (C) a heavy chain including CDRH1 shown in SEQ ID NO: 21, CDRH2 shown in SEQ ID NO: 22, and CDRH3 shown in SEQ ID NO: 23; and a light chain including CDRL1 shown in SEQ ID NO: 24, CDRL2 shown in SEQ ID NO: 25, and CDRL3 shown in SEQ ID NO: 26, to which is attached a payload; and measuring a signal from the payload, wherein the signal is indicative of or correlated with DG protein level on the surface of and/or inside cells. In particular embodiments, the payload is directly attached or indirectly attached to the antibody or antigen-binding fragment thereof. In particular embodiments, the payload includes a detectable agent or biologically functional molecule. In particular embodiments, the detectable agent includes a dye, a contrast agent, a fluorescent tag, a bioluminescent tag, a chemiluminescent tag, a nucleic acid barcode, an affinity tag, an enzyme, a radioisotope, a nanoparticle, or a combination thereof. In particular embodiments, measuring the signal from the payload includes using bioluminescence imaging (BLI), magnetic resonance imaging (MRI), positron emission tomography (PET), X-ray computed tomography, Raman imaging, optical coherence tomography, absorption imaging, thermal imaging, fluorescence reflectance imaging, fluorescence microscopy, fluorescence guided imaging systems, fluorescence molecular tomographic imaging, nuclear magnetic resonance imaging, X-ray imaging, ultrasound imaging, photoacoustic imaging, or a combination thereof. In particular embodiments, the biologically functional molecule includes a radioisotope, a toxin, a nanoparticle, a nanoparticle comprising a nucleic acid, a nucleic acid, an mRNA, an siRNA, a miRNA, a small molecule drug, or a combination thereof. In particular embodiments, the disorder includes oral cancers, esophageal cancers, stomach cancers, pancreatic cancers, lung cancers, breast cancers, skin cancers, colon cancers, uterine cancers, fallopian tube cancers, and bladder cancers. In particular embodiments, the disorder is a pancreatic cyst. In particular embodiments, the disorder is early stage bladder cancer. In particular embodiments, the early stage bladder cancer is an early stage micropapillary urothelial carcinoma (MPUC) of the bladder or an MPUC of the upper tract of the bladder.

In particular embodiments, the anti-DG antibody/payload can bind on the surface of cells expressing DG in the subject. In particular embodiments, the surface of cells expressing DG in the subject is the lumenal surface. The anti-DG antibody/payload can also be internalized into the cell, for example, via endocytic vesicles of the cells following binding. Thus, in particular embodiments, binding and/or internalization of the anti-DG antibody/payload can be measured as a signal from the payload. In particular embodiments, the signal from the payload is indicative of or correlated with DG protein level on the surface and/or inside the cells. In particular embodiments, an increase in the signal indicates an increase in the dystroglycan protein level, and a decrease in the signal indicates a decrease in the dystroglycan protein level, as compared to a reference signal from reference cells. In particular embodiments, binding and/or internalization of the anti-DG antibody/payload can be measured as expression of a protein encoded by a nucleic acid (e.g., an mRNA) of the payload. In particular embodiments, binding and/or internalization of the anti-DG antibody/payload can be measured as a reduction in expression or absence of a protein in the targeted cell due to downregulation of its expression by a nucleic acid (e.g., siRNA) of a payload. In particular embodiments, the cells targeted by the anti-DG antibody/payload are mammalian cells. In particular embodiments, the cells targeted by the anti-DG antibody/payload are human cells. In particular embodiments, the cells targeted by the anti-DG antibody/payload are cancer cells. In particular embodiments, the cells targeted by the anti-DG antibody/payload are cells that have lost apical-basal polarity.

In a method of diagnosing a disorder associated with loss of apical-basal polarity in epithelial cells in a subject, the method can further include comparing the DG protein level obtained from the measuring to the corresponding level from a reference; and diagnosing the subject with the disorder associated with loss of apical-basal polarity in the epithelial cells when the signal is higher than the reference level. In particular embodiments, a subject is diagnosed as having a disorder associated with loss of apical-basal polarity in epithelial cells in a subject when the DG protein level in the subject is 1%, 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 400%, 500%, 600%, 700%, 800%, 900%, 1000%, 2000%, 3000%, 4000%, 5000%, 6000%, 7000%, 8000%, 9000%, 10,000%, 100,000%, 1,000,000%, or higher than the reference level. In particular embodiments, a subject is diagnosed as having a disorder associated with loss of apical-basal polarity in epithelial cells in a subject when the DG protein level in the subject is 2×, 3×, 4×, 5×, 6×, 7×, 8×, 9×, 10×, 15×, 20×, 25×, 30×, 35×, 40×, 45×, 50×, 55×, 60×, 65×, 70×, 75×, 80×, 85×, 90×, 95×, 100×, 200×, 300×, 400×, 500×, 600×, 700×, 800×, 900×, 1000×, 2000×, 3000×, 4000×, 5000×, 6000×, 7000×, 8000×, 9000×, 10,000×, 20,000×, or higher than the reference level. In particular embodiments, a subject is diagnosed as having a disorder associated with loss of apical-basal polarity in epithelial cells in a subject when the measured signal is higher than a reference signal. In particular embodiments, the reference DG protein level or reference signal can be zero. In particular embodiments, the reference level or reference signal is derived from one or more subjects who are healthy or who do not have a disorder associated with loss of apical-basal polarity in epithelial cells. In other embodiments, the reference level or reference signal is derived from normal cells having apical-basal polarity that are adjacent to/found in the same tissue as the cells exhibiting a loss of apical-basal polarity. In particular embodiments, the disorder is early stage bladder cancer. In particular embodiments, the early stage bladder cancer is an early stage micropapillary urothelial carcinoma (MPUC) of the bladder or an MPUC of the upper tract of the bladder.

In a method of determining efficacy of a treatment for a disorder associated with loss of apical-basal polarity in epithelial cells in a subject, the method can further include performing the delivering and the measuring prior to treatment and during and/or after treatment; and determining that the treatment is effective if the DG protein level during or after the treatment is lower than the DG protein level prior to the treatment; or determining that the treatment is not effective if the DG protein level during or after the treatment is equal or higher than the DG protein level prior to the treatment. In particular embodiments, the treatment can be maintained or ceased if the treatment is effective or adjusted if the treatment is not effective. In particular embodiments, the disorder is early stage bladder cancer. In particular embodiments, the early stage bladder cancer is an early stage micropapillary urothelial carcinoma (MPUC) of the bladder or an MPUC of the upper tract of the bladder.

In a method of monitoring a subject for a disorder associated with loss of apical-basal polarity in epithelial cells in a subject, the method can further include comparing the DG protein level obtained from the measuring to the corresponding level from a reference; and repeating the delivering, measuring, and comparing steps. In particular embodiments, the reference level is derived from one or more subjects who are healthy or who do not have a disorder associated with loss of apical-basal polarity in epithelial cells. In other embodiments, the reference level or reference signal is derived from adjacent normal cells having apical-basal polarity. In particular embodiments, the disorder is early stage bladder cancer. In particular embodiments, the early stage bladder cancer is an early stage micropapillary urothelial carcinoma (MPUC) of the bladder or an MPUC of the upper tract of the bladder.

Particular embodiments include methods of measuring or detecting DG protein level in cells ex vivo or in vivo by contacting a cell with or delivering into a subject at least one antibody or antigen-binding fragment thereof described herein attached to a payload. In particular embodiments, methods described herein include contacting a cell with at least one anti-DG antibody or antigen-binding fragment thereof described herein attached to a payload. In particular embodiments, contacting a cell ex vivo with at least one anti-DG antibody or antigen-binding fragment thereof described herein attached to a payload allows specific targeting ex vivo of the payload to a cell or cell population expressing DG. In particular embodiments, contacting a cell in vivo by local administration (e.g., catheter, intravenous, intramuscular, intratumoral, intradermal, intraarterial, intranodal, intralymphatic, intraperitoneal, intralesional, intraprostatic, intravaginal, intrauterine, intrarectal, topical, intrathecal, intraparenchymal, intravesicular, intracerebroventricular, subpial, intravitreal, subretinal, transgastric, transduodenal, intracystic, bronchoscopic, aerosol, direct injection into ligament or tendon, oral and/or subcutaneous) with at least one anti-DG antibody or antigen-binding fragment thereof described herein attached to a payload allows specific targeting in vivo of the payload to a cell or cell population expressing DG.

In particular embodiments, contacting includes placement in direct physical association, including contacting of a solid with a solid, a liquid with a liquid, a liquid with a solid, or either a liquid or a solid with a cell or tissue, whether in vitro or in vivo. Contacting can occur in vitro with isolated cells or tissue or in vivo by administering to a subject. As used herein, the term "in vitro" can refer to events that occur in an artificial environment, e.g., in a test tube or reaction vessel, in cell culture, in a Petri dish, etc., rather than within an organism (e.g., animal, plant, or microbe). As used herein, the term "ex vivo" can refer to events that occur outside of an organism. As used herein, the term "in vivo" refers to events that occur within an organism (e.g., animal, plant, or microbe or cell or tissue thereof).

The method further includes observing binding of the payload on the surface of a cell or observing internalization of the payload into the cell, for example, via endocytic vesicles. The method can further include observing both the binding of the payload on the surface of the cell and the internalization of the payload into endocytic vesicles. The techniques used in observing the binding of the payload on the surface of the cell and/or observing the internalization of the payload in the endocytic vesicles will depend on the type of payload used and whether or not the observation is of the binding, the internalization, or both. For example, a fluorescent tag can be observed assembling on the surface of a cell by fluorescence microscopy. Internalization of a fluorescent tag can be observed using flow cytometry. Binding or internalization of an MRI contrast agent can be observed using magnetic resonance imaging. Internalization of a nucleic acid can be assessed by selecting for cells that express a protein encoded by the nucleic acid (e.g., mRNA) or detecting cells that have a reduction in or absence of a protein downregulated in its expression by the nucleic acid (e.g., siRNA), for instance. One of ordinary skill in the art would be able to select the detection method appropriate for the type of payload used.

In particular embodiments, measuring DG protein level in a subject includes recording the DG protein level appropriately so that the subject receives or does not receive appropriate treatment or disease management based upon the DG protein level. The recording can include physically marking a container that a test sample derived from the subject resides in with appropriate information or putting such appropriate information about the test sample derived from the subject into a computer. In particular embodiments, appropriate information includes whether the test sample derived from the subject has a lower level of DG protein, a higher level of DG protein, or a same level of DG protein as compared to a level of DG protein in a control sample or as compared to a reference level.

Particular embodiments include methods of transfecting a cell with a payload using the compositions disclosed herein. Particular embodiments include methods of targeting a payload to the lysosome using the compositions disclosed herein.

Particular embodiments include methods of identifying a cell as lacking apical-basal polarity. In particular embodiments, the methods include exposure of an apical cell surface to an antibody that binds DG (an anti-DG antibody), typically localized at the basolateral side of a polarized cell. In this scenario, the absence of binding at the apical cell surface can indicate the maintenance of apical-basal polarity (i.e. intact segregation of the apical and basal membrane domains), and the presence of binding would indicate the loss of polarity (i.e. a breakdown in the barrier between the two membrane domains). The coupling of an imaging or contrast agent to the anti-DG antibody can enable detection of binding by a variety of methods as described herein. The anti-DG antibody, conjugated to a detectable agent, would therefore include a molecular sensor for the loss of polarity.

Measurement of sensor binding to the apical cell surface can be achieved by detecting the binding at the cell surface and also by detecting the internalization of the sensor into the cell interior. Membrane proteins on the cell surface, and the ligands that bind them, can be internalized through various mechanisms of endocytosis. Endocytic internalization of cell surface proteins and their ligands occurs at different rates and efficiencies and pass through different endocytic pathways (Duncan & Richardson, *Mol Pharm* 9, 2380-2402, 2012). Importantly for measures of sensor binding, the abundance of the surface protein, the efficiency of endocytosis, the kinetics of endocytosis and the pathways of endocytosis can each be either advantageous or disadvantageous to signal detection. For example, a high rate of internalization and a long duration of retention within the cell could, in many cases, enhance a detection signal. Conversely, a low rate of internalization and/or a rapid degradation or recycling of the signal (either by chemical degradation or release from the cell) could reduce the detection signal.

The identification of a cell that lacks apical-basal polarity through observing binding and/or internalization of an anti-DG antibody or antigen-binding fragment thereof attached to a payload can be used for any number of downstream purposes. For example, identification of a cell that has lost apical-basal polarity using an anti-DG antibody or antigen-binding fragment thereof labeled with an MRI contrast agent can indicate recurrence of bladder cancer. Alternatively, identification of a cell that has lost apical-basal polarity using a fluorescent label can signal cancerous tissue that can further be removed using fluorescence-guided surgery (Pan et al., *Sci Transl Med,* 6, 260ra148, 2014). In particular embodiments, measuring DG protein level in a subject includes recording the amount of fluorescence in a cell, in a lesion, in a tumor, or in a region of a tissue or organ.

Particular embodiments provide methods of identifying test compounds that restore apical-basal polarity including contacting a test compound to a cell that lacks apical-basal polarity and contacting the cell with an antibody or antigen-binding fragment thereof (attached to a payload) that specifically binds DG. Binding of the payload on the cell surface and/or internalization of the payload into endocytic vesicles can be observed as described above. Test compounds that prevent binding of the payload on the surface and internalization of the payload into endocytic vesicles are identified as compounds that restore apical-basal polarity.

A test compound can be any small molecule, natural product, protein, aptamer, siRNA, or any other molecule that could be used to contact a cell. A test compound is generally provided in a vehicle, such as a solvent. The vehicle can be any appropriate solvent including compositions including water, ions, or organic compounds. Examples of vehicles include buffered saline or other buffered solvents or DMSO or other organic solvents. A test compound can include a compound known to restore apical-basal polarity and that can is used as a positive control. A test compound can include a compound known not to restore apical-basal activity and that is used as a negative control. In particular embodiments, the vehicle alone can be used as a negative control. The methods herein can be used to screen a plurality of test compounds, also described as a library of test compounds. The methods herein can be further adapted to high throughput screening of a set of test compounds in batches of 96, 384, or 1048 on assay plates adapted for such screening.

In particular embodiments, a therapeutic, such as a nucleic acid encoding a therapeutic gene, a siRNA to downregulate a target gene (such as a disease-causing gene), or a kinase inhibitor, can be delivered to the cell interior for the correction of a cellular defect. In certain embodiments, a cell exhibiting intact apical-basal polarity will be unable (or resistant) to internalizing the therapeutic from the apical domain when targeting a typically basolateral cell surface molecule, and vice versa. Upon loss of apical-basal polarity, this resistance would disappear, and selective targeting of the diseased cell would result. In another scenario, a cell with or without apical-basal polarity would be able to internalize the therapeutic due to contact with an anti-DG antibody/therapeutic ex vivo or due to contact with an anti-DG antibody/therapeutic in vivo by local administration.

(XI) KITS

The systems and methods disclosed herein include kits. Disclosed kits include materials and reagents necessary to assay a sample obtained from a subject for diagnosis and/or monitoring of a disorder (e.g., early stage bladder cancer). In particular embodiments, a kit includes at least one antibody or antigen-binding fragment thereof including: (A) a heavy chain including CDRH1 shown in SEQ ID NO: 1, CDRH2 shown in SEQ ID NO: 2, and CDRH3 shown in SEQ ID NO: 3; and a light chain including CDRL1 shown in SEQ ID NO: 4, CDRL2 shown in SEQ ID NO: 5, and CDRL3 shown in SEQ ID NO: 6; or (B) a heavy chain including CDRH1 shown in SEQ ID NO: 11, CDRH2 shown in SEQ ID NO: 12, and CDRH3 shown in SEQ ID NO: 13; and a light chain including CDRL1 shown in SEQ ID NO: 14, CDRL2 shown in SEQ ID NO: 15, and CDRL3 shown in SEQ ID NO: 16; or (C) a heavy chain including CDRH1 shown in SEQ ID NO: 21, CDRH2 shown in SEQ ID NO: 22, and CDRH3 shown in SEQ ID NO: 23; and a light chain including CDRL1 shown in SEQ ID NO: 24, CDRL2 shown in SEQ ID NO: 25, and CDRL3 shown in SEQ ID NO: 26. In particular embodiments, a kit includes at least one antibody or antigen-binding fragment thereof including: (A) a VH domain set forth in SEQ ID NO: 7 and/or a VL domain set forth in SEQ ID NO: 9; (B) a VH domain set forth in SEQ ID NO: 17 and/or a VL domain set forth in SEQ ID NO: 19; and/or (C) a VH domain set forth in SEQ ID NO: 27 and/or a VL domain set forth in SEQ ID NO: 29. In particular embodiments, a kit includes at least one antibody or antigen-binding fragment thereof including: (A) a heavy chain set forth in SEQ ID NO: 8 and/or a light chain set forth in SEQ ID NO: 10; (B) a heavy chain set forth in SEQ ID NO: 18 and/or a light chain set forth in SEQ ID NO: 20; and/or (C) a heavy chain set forth in SEQ ID NO: 28 and/or a light chain set forth in SEQ ID NO: 30. In particular embodiments, a kit includes at least one antibody or antigen-binding fragment thereof including: (A) a heavy chain encoded by SEQ ID NOs: 31 and/or 32, and/or a light chain encoded by SEQ ID NOs: 33 and/or 34; (B) a heavy chain encoded by SEQ ID NOs: 35 and/or 36, and/or a light chain encoded by SEQ ID NOs: 37 and/or 38; and/or (C) a heavy chain encoded by SEQ ID NOs: 39 and/or 40, and/or a light chain encoded by SEQ ID NOs: 41 and/or 42. In particular embodiments, the at least one antibody or antigen-binding fragment thereof is conjugated or labeled with one or more payload. In particular embodiments, the payload can include a therapeutic agent. In particular embodiments, the therapeutic agent includes a cytotoxin, a radioactive isotope, a chemotherapeutic agent, and/or a nanoparticle (for instance, a nanoparticle including a nucleic acid, such as a nucleic acid encoding a therapeutic protein). In particular embodiments, the at least one antibody or antigen-binding fragment thereof is conjugated to a detectable agent. In particular embodiments, the detectable agent includes a fluorescent label, a nucleic acid barcode, a radioactive isotope, an affinity tag, an enzyme, a nanoparticle, and a contrast agent. In particular embodiments, the at least one antibody or antigen-binding fragment thereof is conjugated to paclitaxel or maytansinoid DM1. In particular embodiments, the at least one antibody or antigen-binding fragment thereof can be bound to a solid support such as beads, cellulose, or an array.

The components of the kits can be packaged either in aqueous media or in lyophilized form. The container means of the kits can include at least one vial, test tube, flask, bottle, syringe or other container means, into which a component may be placed, and preferably, suitably aliquoted. Where there is more than one component in the kit, the kit can include a second, third or other additional container into which the additional components may be separately placed. The kits may also include a second container means for containing a sterile, pharmaceutically acceptable buffer and/or other diluent. In particular embodiments, various combinations of components may be included in a vial.

A kit may include instructions for employing the kit components as well the use of any other reagent not included in the kit. Instructions may include variations that can be implemented.

(XII) VARIANTS

Variants of antibodies or antigen-binding fragments thereof and proteins disclosed and referenced herein are also included. Guidance in determining which amino acid residues can be substituted, inserted, or deleted without abolishing biological activity can be found using computer programs well known in the art, such as DNASTAR™ (Madison, Wisconsin) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al., *Molecular Biology of the Gene,* 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (lie), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, lie, Phe, Met, and Trp; Group 11 (aliphatic): Gly, Ala, Val, Leu, and lie; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W. H. Freeman and Company.

In making such changes, the hydropathic index of amino acids may be considered. The importance of the hydropathic amino acid index in conferring interactive biologic function on a protein is generally understood in the art (Kyte & Doolittle, *J. Mol. Biol.* 157(1), 105-32, 1982). Each amino acid has been assigned a hydropathic index on the basis of its hydrophobicity and charge characteristics (Kyte & Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3);

Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul et al., *J. Mol. Biol.*, 215:403-410,1990; DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M NaH$_2$PO$_4$; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

(XIII) EXEMPLARY EMBODIMENTS

1. An isolated antibody or antigen-binding fragment thereof that binds to dystroglycan (DG), including: (A) a heavy chain including: CDRH1 set forth in SEQ ID NO: 1, CDRH2 set forth in SEQ ID NO: 2, and CDRH3 set forth in SEQ ID NO: 3; and a light chain including: CDRL1 set forth in SEQ ID NO: 4, CDRL2 set forth in SEQ ID NO: 5, and CDRL3 set forth in SEQ ID NO: 6; or (B) a heavy chain including: CDRH1 set forth in SEQ ID NO: 11, CDRH2 set forth in SEQ ID NO: 12, and CDRH3 set forth in SEQ ID NO: 13; and a light chain including: CDRL1 set forth in SEQ ID NO: 14, CDRL2 set forth in SEQ ID NO: 15, and CDRL3 set forth in SEQ ID NO: 16; or (C) a heavy chain including: CDRH1 set forth in SEQ ID NO: 21, CDRH2 set forth in SEQ ID NO: 22, and CDRH3 set forth in SEQ ID NO: 23; and a light chain including: CDRL1 set forth in SEQ ID NO: 24, CDRL2 set forth in SEQ ID NO: 25, and CDRL3 set forth in SEQ ID NO: 26; wherein the binding is independent of variable DG glycosylation.

2. The isolated antibody or antigen-binding fragment thereof of embodiment 1(A), including: a variable heavy (VH) domain set forth in SEQ ID NO: 7; a heavy chain set forth in SEQ ID NO: 8; a variable light (VL) domain set forth in SEQ ID NO: 9; and/or a light chain set forth in SEQ ID NO: 10.

3. The isolated antibody or antigen-binding fragment thereof of embodiment 1(B), including: a variable heavy (VH) domain set forth in SEQ ID NO: 17; a heavy chain set forth in SEQ ID NO: 18; a variable light (VL) domain set forth in SEQ ID NO: 19; and/or a light chain set forth in SEQ ID NO: 20.

4. The isolated antibody or antigen-binding fragment thereof of embodiment 1(C), including: a variable heavy (VH) domain set forth in SEQ ID NO: 27; a heavy chain set forth in SEQ ID NO: 28; a variable light (VL) domain set forth in SEQ ID NO: 29; and/or a light chain set forth in SEQ ID NO: 30.

5. The isolated antibody or antigen-binding fragment thereof of embodiment 1(A), including: a heavy chain encoded by SEQ ID NOs: 31 and 32; and/or a light chain encoded by SEQ ID NOs: 33 and 34.

6. The isolated antibody or antigen-binding fragment thereof of embodiment 1(B), including: a heavy chain encoded by SEQ ID NOs: 35 and 36; and/or a light chain encoded by SEQ ID NOs: 37 and 38.

7. The isolated antibody or antigen-binding fragment thereof of embodiment 1(C), including: a heavy chain encoded by SEQ ID NOs: 39 and 40; and/or a light chain encoded by SEQ ID NOs: 41 and 42.

8. The isolated antibody or antigen-binding fragment thereof of embodiment 1(A), which is produced by hybridoma DG1A11 or binds competitively with the antibody that is produced by that hybridoma.

9. The isolated antibody or antigen-binding fragment thereof of embodiment 1(B), which is produced by hybridoma DGH6 or binds competitively with the antibody that is produced by that hybridoma.

10. The isolated antibody or antigen-binding fragment thereof of embodiment 1(C), which is produced by hybridoma DG4H4 or binds competitively with the antibody that is produced by that hybridoma.

11. The isolated antibody or antigen-binding fragment thereof of embodiment 1, which binds to DG that is expressed on the surface of a living cell.

12. The isolated antibody or antigen-binding fragment thereof of embodiment 1, wherein the DG is human or non-human primate.

13. A method of measuring DG protein level in cells in vivo, including: delivering into a subject the antibody or antigen-binding fragment thereof of embodiment 1, to which is attached a payload; and measuring a signal from the payload, wherein the signal is indicative of or correlated with DG protein level on the surface of and/or inside cells.

14. The method of embodiment 13, wherein the surface is the lumenal surface.

15. The method of embodiment 13 or 14, wherein the delivering is intravesicularly.

16. A method of targeting a payload to a cell, including contacting a cell with the antibody or antigen-binding fragment thereof of embodiment 1, to which is attached a payload.

17. A method of measuring DG protein level in cells ex vivo, including: contacting a cell with the antibody or antigen-binding fragment thereof of embodiment 1, to which is attached a payload; and measuring a signal from the payload, wherein the signal is indicative of or correlated with DG protein level on the surface of and/or inside the cell.

18. A method of targeting a payload to a cell lacking apical-basal polarity, including: contacting a cell with the antibody or antigen-binding fragment thereof of embodiment 1, to which is attached a payload; and measuring a signal from the payload, wherein the signal is indicative of or correlated with DG protein level on the surface of and/or inside the cell.

19. A method of identifying a cell as lacking apical-basal polarity, including: contacting a cell with the antibody or antigen-binding fragment thereof of embodiment 1, to which is attached a payload; and measuring a signal from the payload, wherein the signal is indicative of or correlated with DG protein level on the surface of and/or inside the cell.

20. A method of identifying a test compound that promotes apical-basal polarity in a cell lacking apical-basal polarity, including contacting a cell with the antibody or antigen-binding fragment thereof of embodiment 1, to which is attached a payload; and measuring a signal from the payload, wherein the signal is indicative of or correlated with DG protein level on the surface of and/or inside the cell.

21. The method of embodiment 20, further including contacting the cell with the test compound, wherein an absence or decrease in the DG protein level on the surface of and/or inside the cell as compared to a reference level indicates that the test compound promotes apical-basal polarity.

22. The method of embodiment 20 or 21, wherein the reference level is derived from cells that lack apical-basal polarity.

23. The method of any one of embodiments 16-22, wherein the cell is in a population of cells in a test sample.

24. The method of any one of embodiments 13-23, wherein the cells are mammalian cells.

25. The method of any one of embodiments 13-24, wherein the cells are human cells.

26. The method of any one of embodiments 13-15, and 17-25, wherein an increase in the signal indicates an increase in the DG protein level and wherein a decrease in the signal indicates a decrease in the DG protein level.

27. The method of any one of embodiments 13-15, and 17-19, further comparing the DG protein level obtained from the measuring to the corresponding level from a reference DG protein level.

28. The method of embodiment 27, wherein the reference DG protein level is derived from one or more healthy subjects.

29. The method of embodiment 27 or 28, wherein the reference DG protein level is derived from cells in adjacent normal tissue.

30. The method of any one of embodiments 27-29, wherein the reference DG protein level is derived from cells that have apical-basal polarity.

31. The method of embodiment 27, wherein the reference DG protein level is derived from cells that have lost apical-basal polarity.

32. A method of diagnosing a disorder associated with loss of apical-basal polarity in epithelial cells in a subject, including: delivering into a subject: the antibody or antigen-binding fragment thereof of embodiment 1, to which is attached a payload; measuring a signal from the payload, wherein the signal is indicative of or correlated with DG protein level on the surface of and/or inside cells; and comparing the DG protein level obtained from the measuring to the corresponding level from a reference DG protein level or a reference signal.

33. The method of embodiment 32, further including diagnosing the subject with the disorder associated with loss of apical-basal polarity in the epithelial cells when the signal is higher than the reference DG protein level or the reference signal.

34. The method of embodiment 33, wherein the DG protein level in the subject is 2× to 20,000× higher than the reference DG protein level.

35. A method of monitoring a subject for a disorder associated with loss of apical-basal polarity in epithelial cells in a subject, including: delivering into a subject the antibody or antigen-binding fragment thereof of embodiment 1, to which is attached a payload; measuring a signal from the payload, wherein the signal is indicative of or correlated with DG protein level on the surface of and/or inside cells; and comparing the DG protein level obtained from the measuring to the corresponding level from a reference DG protein level or a reference signal.

36. The method of embodiment 35, further including: repeating the delivering, measuring, and comparing, thereby monitoring the disorder associated with loss of apical-basal polarity in the epithelial cells in the subject.

37. The method of any one of embodiments 32-36, wherein the reference DG protein level is zero.

38. The method of any one of embodiments 32-36, wherein the reference signal is zero.

39. The method of any one of embodiments 32-38, wherein the reference DG protein level or the reference signal is derived from one or more individuals not having the disorder associated with loss of apical-basal polarity in the epithelial cells or is derived from adjacent normal tissue in the subject.

40. A method of determining efficacy of a treatment in a subject being treated for a disorder associated with loss of apical-basal polarity in epithelial cells in the subject, including: delivering into a subject the antibody or antigen-binding fragment thereof of embodiment 1, to which is attached a payload; and measuring a signal from the payload, wherein the signal is indicative of or correlated with DG protein level on the surface of and/or inside cells.

41. The method of embodiment 40, further including: performing the delivering and the measuring prior to treatment and during and/or after treatment; and determining that the treatment is effective when the DG protein level during or after the treatment is lower than the DG protein level prior to the treatment; or determining that the treatment is not effective when the DG protein level during or after the treatment is equal to or higher than the DG protein level prior to the treatment.

42. The method of embodiment 41, further including maintaining or ceasing the treatment when the treatment is effective or adjusting the treatment when the treatment is not effective.

43. The method of any one of embodiments 32-42, wherein the delivering is intravesicularly.

44. The method of any one of embodiments 32-43, wherein the disorder is early stage bladder cancer.

45. The method of any one of embodiments 32-44, wherein the early stage bladder cancer is an early stage micropapillary urothelial carcinoma (MPUC) of the bladder or an MPUC of the upper tract of the bladder.

46. The method of any one of embodiments 13-45, wherein the payload is directly attached or indirectly attached to the antibody or antigen-binding fragment thereof.

47. The method of any one of embodiments 13-46, wherein the antibody or antigen-binding fragment thereof binds DG on the surface of the cells.

48. The method of any one of embodiments 13-47, wherein the payload is internalized by the cells.

49. The method of any one of embodiments 13-48, wherein the cells are cancer cells.

50. The method of any one of embodiments 13-49, wherein the payload includes a detectable agent and/or a biologically functional molecule.

51. The method of embodiment 50, wherein the detectable agent includes a fluorescent tag, a bioluminescent tag, a chemiluminescent tag, a nucleic acid barcode, an affinity tag, an enzyme, a radioisotope, a magnetic resonance imaging contrast agent, and/or a nanoparticle.

52. The method of embodiment 50, wherein the biologically functional molecule includes a radioisotope, a toxin, a nanoparticle including a nucleic acid, a nucleic acid, an mRNA, an siRNA, and/or a small molecule drug.

53. The method of any one of embodiments 13-15, and 17-52, wherein measuring the signal from the payload includes using optical imaging, fluorescence imaging, radio-isotope imaging, or magnetic resonance imaging.

54. The method of any one of embodiments 13-15, and 17-53, wherein measuring the signal from the payload includes recording a level of the signal in a cell, in a lesion, in a tumor, or in a region of a tissue or organ.

55. A method of treating a disorder in a subject in need thereof, including: administering to the subject a therapeutically effective amount of at least one antibody or antigen-binding fragment thereof attached to one or more payloads including a therapeutic agent, wherein the at least one antibody or antigen-binding fragment thereof binds to dystroglycan (DG) and includes: (A) a heavy chain including: CDRH1 set forth in SEQ ID NO: 1, CDRH2 set forth in SEQ ID NO: 2, and CDRH3 set forth in SEQ ID NO: 3; and a light chain including: CDRL1 set forth in SEQ ID NO: 4, CDRL2 set forth in SEQ ID NO: 5, and CDRL3 set forth in SEQ ID NO: 6; (B) a heavy chain including: CDRH1 set forth in SEQ ID NO: 11, CDRH2 set forth in SEQ ID NO: 12, and CDRH3 set forth in SEQ ID NO: 13; and a light chain including: CDRL1 set forth in SEQ ID NO: 14, CDRL2 set forth in SEQ ID NO: 15, and CDRL3 set forth in SEQ ID NO: 16; and/or (C) a heavy chain including: CDRH1 set forth in SEQ ID NO: 21, CDRH2 set forth in SEQ ID NO: 22, and CDRH3 set forth in SEQ ID NO: 23; and a light chain including: CDRL1 set forth in SEQ ID NO: 24, CDRL2 set forth in SEQ ID NO: 25, and CDRL3 set forth in SEQ ID NO: 26; wherein the binding is independent of variable DG glycosylation, thereby treating a disorder in the subject.

56. A method of treating a disorder associated with loss of apical-basal polarity in epithelial cells in a subject in need thereof, including: administering to the subject a therapeutically effective amount of at least one antibody or antigen-binding fragment thereof attached to one or more payloads including a therapeutic agent, wherein the at least one antibody or antigen-binding fragment thereof binds to dystroglycan (DG) and includes: (A) a heavy chain including: CDRH1 set forth in SEQ ID NO: 1, CDRH2 set forth in SEQ ID NO: 2, and CDRH3 set forth in SEQ ID NO: 3; and a light chain including: CDRL1 set forth in SEQ ID NO: 4, CDRL2 set forth in SEQ ID NO: 5, and CDRL3 set forth in SEQ ID NO: 6; (B) a heavy chain including: CDRH1 set forth in SEQ ID NO: 11, CDRH2 set forth in SEQ ID NO: 12, and CDRH3 set forth in SEQ ID NO: 13; and a light chain including: CDRL1 set forth in SEQ ID NO: 14, CDRL2 set forth in SEQ ID NO: 15, and CDRL3 set forth in SEQ ID NO: 16; and/or (C) a heavy chain including: CDRH1 set forth in SEQ ID NO: 21, CDRH2 set forth in SEQ ID NO: 22, and CDRH3 set forth in SEQ ID NO: 23; and a light chain including: CDRL1 set forth in SEQ ID NO: 24, CDRL2 set forth in SEQ ID NO: 25, and CDRL3 set forth in SEQ ID NO: 26; wherein the binding is independent of variable DG glycosylation, thereby treating a disorder associated with loss of apical-basal polarity in the epithelial cells in the subject.

57. The method of embodiment 55 or 56, wherein the one or more payloads are directly or indirectly attached to the at least one antibody or antigen-binding fragment thereof.

58. A method of treating a disorder in a subject in need thereof, including: administering to the subject a therapeutically effective amount of at least one antibody or antigen-binding fragment thereof that binds to dystroglycan (DG);

and administering to the subject a therapeutically effective amount of one or more payloads including a therapeutic agent, wherein the at least one antibody or antigen-binding fragment thereof includes: (A) a heavy chain including: CDRH1 set forth in SEQ ID NO: 1, CDRH2 set forth in SEQ ID NO: 2, and CDRH3 set forth in SEQ ID NO: 3; and a light chain including: CDRL1 set forth in SEQ ID NO: 4, CDRL2 set forth in SEQ ID NO: 5, and CDRL3 set forth in SEQ ID NO: 6; (B) a heavy chain including: CDRH1 set forth in SEQ ID NO: 11, CDRH2 set forth in SEQ ID NO: 12, and CDRH3 set forth in SEQ ID NO: 13; and a light chain including: CDRL1 set forth in SEQ ID NO: 14, CDRL2 set forth in SEQ ID NO: 15, and CDRL3 set forth in SEQ ID NO: 16; and/or (C) a heavy chain including: CDRH1 set forth in SEQ ID NO: 21, CDRH2 set forth in SEQ ID NO: 22, and CDRH3 set forth in SEQ ID NO: 23; and a light chain including: CDRL1 set forth in SEQ ID NO: 24, CDRL2 set forth in SEQ ID NO: 25, and CDRL3 set forth in SEQ ID NO: 26; wherein the binding is independent of variable DG glycosylation, thereby treating a disorder in the subject.

59. A method of treating a disorder associated with loss of apical-basal polarity in epithelial cells in a subject in need thereof, including: administering to the subject a therapeutically effective amount of at least one antibody or antigen-binding fragment thereof that binds to dystroglycan (DG); and administering to the subject a therapeutically effective amount of one or more payloads including a therapeutic agent, wherein the at least one antibody or antigen-binding fragment thereof includes: (A) a heavy chain including: CDRH1 set forth in SEQ ID NO: 1, CDRH2 set forth in SEQ ID NO: 2, and CDRH3 set forth in SEQ ID NO: 3; and a light chain including: CDRL1 set forth in SEQ ID NO: 4, CDRL2 set forth in SEQ ID NO: 5, and CDRL3 set forth in SEQ ID NO: 6; (B) a heavy chain including: CDRH1 set forth in SEQ ID NO: 11, CDRH2 set forth in SEQ ID NO: 12, and CDRH3 set forth in SEQ ID NO: 13; and a light chain including: CDRL1 set forth in SEQ ID NO: 14, CDRL2 set forth in SEQ ID NO: 15, and CDRL3 set forth in SEQ ID NO: 16; and/or (C) a heavy chain including: CDRH1 set forth in SEQ ID NO: 21, CDRH2 set forth in SEQ ID NO: 22, and CDRH3 set forth in SEQ ID NO: 23; and a light chain including: CDRL1 set forth in SEQ ID NO: 24, CDRL2 set forth in SEQ ID NO: 25, and CDRL3 set forth in SEQ ID NO: 26; wherein the binding is independent of variable DG glycosylation, thereby treating a disorder associated with loss of apical-basal polarity in the epithelial cells in the subject.

60. The method of embodiment 58 or 59, wherein the one or more payloads bind the at least one antibody or antigen-binding fragment thereof in vivo after the administering of the one or more payloads.

61. The method of embodiment 60, wherein the one or more payloads binds covalently or non-covalently to the at least one antibody or antigen-binding fragment thereof.

62. The method of embodiment 61, wherein the covalent binding of the one or more payloads to the at least one antibody or antigen-binding fragment thereof occurs by a Diels-Alder reaction.

63. The method of embodiment 60, wherein the non-covalent binding of the one or more payloads to the at least one antibody or antigen-binding fragment thereof occurs through an affinity tag.

64. The method of any one of embodiments 55-63, wherein the therapeutic agent includes one or more of a radioisotope, a toxin, a nanoparticle, a nanoparticle including a nucleic acid, an mRNA, an siRNA, and/or a small molecule drug.

65. The method of any one of embodiments 55-64, wherein the disorder is polycystic kidney disease, retinitis pigmentosa, cystic fibrosis, interstitial cystitis, actinic keratosis, or cancer.

66. The method of any one of embodiments 55-65, wherein the disorder is early stage bladder cancer.

67. The method of any one of embodiments 55-66, wherein the early stage bladder cancer is an early stage micropapillary urothelial carcinoma (MPUC) of the bladder or an MPUC of the upper tract of the bladder.

68. The method of any one of embodiments 55-65, wherein the administering is locally administering.

69. The method of embodiment 68, wherein the locally administering includes: delivery by catheter; intravenous delivery; intramuscular delivery; intratumoral delivery; intradermal delivery; intraarterial delivery; intranodal delivery; intralymphatic delivery; intraperitoneal delivery; intralesional delivery; intraprostatic delivery; intravaginal delivery; intrauterine delivery; intrarectal delivery; topical delivery; intrathecal delivery; intraparenchymal delivery; intravesicular delivery; intracerebroventricular delivery; subpial delivery; intravitreal delivery; subretinal delivery; transgastric delivery; transduodenal delivery; intracystic delivery; bronchoscopic delivery; aerosol delivery; direct injection into ligament or tendon; oral delivery; subcutaneous delivery; or a combination thereof.

70. The method of any one of embodiments 55-69, wherein the administering is intravesicularly.

71. A pharmaceutical composition including: at least one antibody or antigen-binding fragment thereof that binds to dystroglycan (DG), including: (A) a heavy chain including: CDRH1 set forth in SEQ ID NO: 1, CDRH2 set forth in SEQ ID NO: 2, and CDRH3 set forth in SEQ ID NO: 3; and a light chain including: CDRL1 set forth in SEQ ID NO: 4, CDRL2 set forth in SEQ ID NO: 5, and CDRL3 set forth in SEQ ID NO: 6; (B) a heavy chain including: CDRH1 set forth in SEQ ID NO: 11, CDRH2 set forth in SEQ ID NO: 12, and CDRH3 set forth in SEQ ID NO: 13; and a light chain including: CDRL1 set forth in SEQ ID NO: 14, CDRL2 set forth in SEQ ID NO: 15, and CDRL3 set forth in SEQ ID NO: 16; and/or (C) a heavy chain including: CDRH1 set forth in SEQ ID NO: 21, CDRH2 set forth in SEQ ID NO: 22, and CDRH3 set forth in SEQ ID NO: 23; and a light chain including: CDRL1 set forth in SEQ ID NO: 24, CDRL2 set forth in SEQ ID NO: 25, and CDRL3 set forth in SEQ ID NO: 26, wherein the binding is independent of variable DG glycosylation, and wherein the at least one antibody or antigen-binding fragment thereof is attached to one or more payloads.

72. The pharmaceutical composition of embodiment 71(A), wherein the at least one antibody or antigen-binding fragment thereof includes: a variable heavy (VH) domain set forth in SEQ ID NO: 7; a heavy chain set forth in SEQ ID NO: 8; a variable light (VL) domain set forth in SEQ ID NO: 9; and/or a light chain set forth in SEQ ID NO: 10.

73. The pharmaceutical composition of embodiment 71(B), wherein the at least one antibody or antigen-binding fragment thereof includes: a variable heavy (VH) domain set forth in SEQ ID NO: 17; a heavy chain set forth in SEQ ID NO: 18; a variable light (VL) domain set forth in SEQ ID NO: 19; and/or a light chain set forth in SEQ ID NO: 20.

74. The pharmaceutical composition of embodiment 71(C), wherein the at least one antibody or antigen-binding fragment thereof includes: a variable heavy (VH) domain set forth in SEQ ID NO: 27; a heavy chain set forth in SEQ ID NO: 28; a variable light (VL) domain set forth in SEQ ID NO: 29; and/or a light chain set forth in SEQ ID NO: 30.

75. The pharmaceutical composition of embodiment 71(A), wherein the at least one antibody or antigen-binding fragment thereof includes: a heavy chain encoded by SEQ ID NOs: 31 and 32; and/or a light chain encoded by SEQ ID NOs: 33 and 34.

76. The pharmaceutical composition of embodiment 71(B), wherein the at least one antibody or antigen-binding fragment thereof includes: a heavy chain encoded by SEQ ID NOs: 35 and 36; and/or a light chain encoded by SEQ ID NOs: 37 and 38.

77. The pharmaceutical composition of embodiment 71(C), wherein the at least one antibody or antigen-binding fragment thereof includes: a heavy chain encoded by SEQ ID NOs: 39 and 40; and/or a light chain encoded by SEQ ID NOs: 41 and 42.

78. The pharmaceutical composition of embodiment 71(A), wherein the at least one antibody or antigen-binding fragment thereof is produced by hybridoma DG1A11 or binds competitively with the antibody that is produced by that hybridoma.

79. The pharmaceutical composition of embodiment 71(B), wherein the at least one antibody or antigen-binding fragment thereof is produced by hybridoma DGH6 or binds competitively with the antibody that is produced by that hybridoma.

80. The pharmaceutical composition of embodiment 71(C), wherein the at least one antibody or antigen-binding fragment thereof is produced by hybridoma DG4H4 or binds competitively with the antibody that is produced by that hybridoma.

81. The pharmaceutical composition of any one of embodiments 71-80, wherein the one or more payloads are attached directly or indirectly to the at least one antibody or antigen-binding fragment thereof.

82. The pharmaceutical composition of any one of embodiments 71-81, wherein the one or more payloads include a fluorescent tag, a bioluminescent tag, a chemiluminescent tag, a nucleic acid, a nucleic acid barcode, an affinity tag, an enzyme, a radioisotope, a magnetic resonance imaging contrast agent, a nanoparticle, a nanoparticle including a nucleic acid, a toxin, an mRNA, an siRNA, and/or a small molecule drug.

83. The pharmaceutical composition of any one of embodiments 71-82, wherein the at least one antibody or antigen-binding fragment thereof binds to DG that is expressed on the surface of a living cell.

84. The pharmaceutical composition of any one of embodiments 71-83, wherein the DG is human or non-human primate.

85. A kit including: at least one isolated antibody or antigen-binding fragment thereof that binds to dystroglycan (DG), including: (A) a heavy chain including: CDRH1 set forth in SEQ ID NO: 1, CDRH2 set forth in SEQ ID NO: 2, and CDRH3 set forth in SEQ ID NO: 3; and a light chain including: CDRL1 set forth in SEQ ID NO: 4, CDRL2 set forth in SEQ ID NO: 5, and CDRL3 set forth in SEQ ID NO: 6; (B) a heavy chain including: CDRH1 set forth in SEQ ID NO: 11, CDRH2 set forth in SEQ ID NO: 12, and CDRH3 set forth in SEQ ID NO: 13; and a light chain including: CDRL1 set forth in SEQ ID NO: 14, CDRL2 set forth in SEQ ID NO: 15, and CDRL3 set forth in SEQ ID NO: 16; and/or (C) a heavy chain including: CDRH1 set forth in SEQ ID NO: 21, CDRH2 set forth in SEQ ID NO: 22, and CDRH3 set forth in SEQ ID NO: 23; and a light chain including: CDRL1 set forth in SEQ ID NO: 24, CDRL2 set forth in SEQ ID NO: 25, and CDRL3 set forth in SEQ ID NO: 26; and instructions on use of the at least one isolated antibody or antigen-binding fragment thereof to detect DG, wherein the binding is independent of variable DG glycosylation.

86. The kit of embodiment 85(A), wherein the at least one isolated antibody or antigen-binding fragment thereof includes: a variable heavy (VH) domain set forth in SEQ ID NO: 7; a heavy chain set forth in SEQ ID NO: 8; a variable light (VL) domain set forth in SEQ ID NO: 9; and/or a light chain set forth in SEQ ID NO: 10.

87. The kit of embodiment 85(B), wherein the at least one isolated antibody or antigen-binding fragment thereof includes: a variable heavy (VH) domain set forth in SEQ ID NO: 17; a heavy chain set forth in SEQ ID NO: 18; a variable light (VL) domain set forth in SEQ ID NO: 19; and/or a light chain set forth in SEQ ID NO: 20.

88. The kit of embodiment 85(C), wherein the at least one isolated antibody or antigen-binding fragment thereof includes: a variable heavy (VH) domain set forth in SEQ ID NO: 27; a heavy chain set forth in SEQ ID NO: 28; a variable light (VL) domain set forth in SEQ ID NO: 29; and/or a light chain set forth in SEQ ID NO: 30.

89. The kit of embodiment 85(A), wherein the at least one isolated antibody or antigen-binding fragment thereof includes: a heavy chain encoded by SEQ ID NOs: 31 and 32; and/or a light chain encoded by SEQ ID NOs: 33 and 34.

90. The kit of embodiment 85(B), wherein the at least one isolated antibody or antigen-binding fragment thereof includes: a heavy chain encoded by SEQ ID NOs: 35 and 36; and/or a light chain encoded by SEQ ID NOs: 37 and 38.

91. The kit of embodiment 85(C), wherein the at least one isolated antibody or antigen-binding fragment thereof includes: a heavy chain encoded by SEQ ID NOs: 39 and 40; and/or a light chain encoded by SEQ ID NOs: 41 and 42.

92. The kit of embodiment 85(A), wherein the at least one isolated antibody or antigen-binding fragment thereof is produced by hybridoma DG1A11 or binds competitively with the antibody that is produced by that hybridoma.

93. The kit of embodiment 85(B), wherein the at least one isolated antibody or antigen-binding fragment thereof is produced by hybridoma DGH6 or binds competitively with the antibody that is produced by that hybridoma.

94. The kit of embodiment 85(C), wherein the at least one isolated antibody or antigen-binding fragment thereof is produced by hybridoma DG4H4 or binds competitively with the antibody that is produced by that hybridoma.

95. The kit of any one of embodiments 85-94, wherein the antibody or antigen-binding fragment thereof is conjugated to one or more of a fluorescent tag, a bioluminescent tag, a chemiluminescent tag, a nucleic acid, a nucleic acid barcode, an affinity tag, an enzyme, a radioisotope, a magnetic resonance imaging contrast agent, a nanoparticle, a nanoparticle including a nucleic acid, a toxin, an mRNA, an siRNA, and/or a small molecule drug.

96. The kit of embodiment 95, wherein the conjugation is direct or indirect.

97. The kit of any one of embodiments 85-96, wherein the at least one isolated antibody or antigen-binding fragment thereof binds to DG that is expressed on the surface of a living cell.

98. The kit of any one of embodiments 85-97, wherein the DG is human or non-human primate.

(XIV) EXAMPLES

Example 1. Generation and purification of antibodies. Antibody generation was achieved by immunization of Balb/c mice (Charles River Laboratories, Wilmington, MA) with a living murine mammary epithelial cell line expressing a cDNA encoding the human dystroglycan (DG) protein. The murine cell line, MEpG, was generated as previously described in Weir et al., J. Cell Sci., 119(19): 4047-4058, 2006, along with the creation of its variants expressing the human DG cDNA. The mice to be immunized were first treated for subtractive immunization against the control (non-DG-expressing) murine cell line by intraperitoneally (i.p.) injecting 4 million cells per mouse of the control cell line on Day 0, followed by cyclophosphamide injections (100 mg per kg, i.p.) on Days 1 and 2. The mice were next immunized with the human DG-expressing version of the same cell line (4 million cells per mouse) on Days 19 and 40. On Day 44 the splenocytes were isolated from the immunized mice and subject to standard hybridoma fusion using the Sp2/0 myeloma cell line, the ClonaCell™-HY Hybridoma Kit (STEMCELL Technologies, Cambridge MA, Catalog #03800), and methods provided by STEMCELL Technologies. The fusion products were cultured for colony formation in ClonaCell™-HY Medium D (STEMCELL Technologies, Cambridge MA).

The resulting hybridoma colonies were picked and clonally isolated in 96 well plates 2 weeks after fusion. These clones were propagated in DMEM (Gibco, Cat #11995) supplemented with 10% FBS (Hyclone, Cat #SH30396.03), 1% Pen Strep (Gibco, Cat #15140-122), 1% Sodium Pyruvate (Gibco, Cat #11360-070), 1% L-Glutamine (Gibco, Cat #25030-081), 1% MEM Vitamin (Gibco, Cat #11120-052), 1% HEPES (Gibco, Cat #15630-080), and 0.1% 2-ME (Gibco, Cat #21985-023). After 4 days, the supernatants were collected from the 96 well plates and screened for activity.

Figure 3:
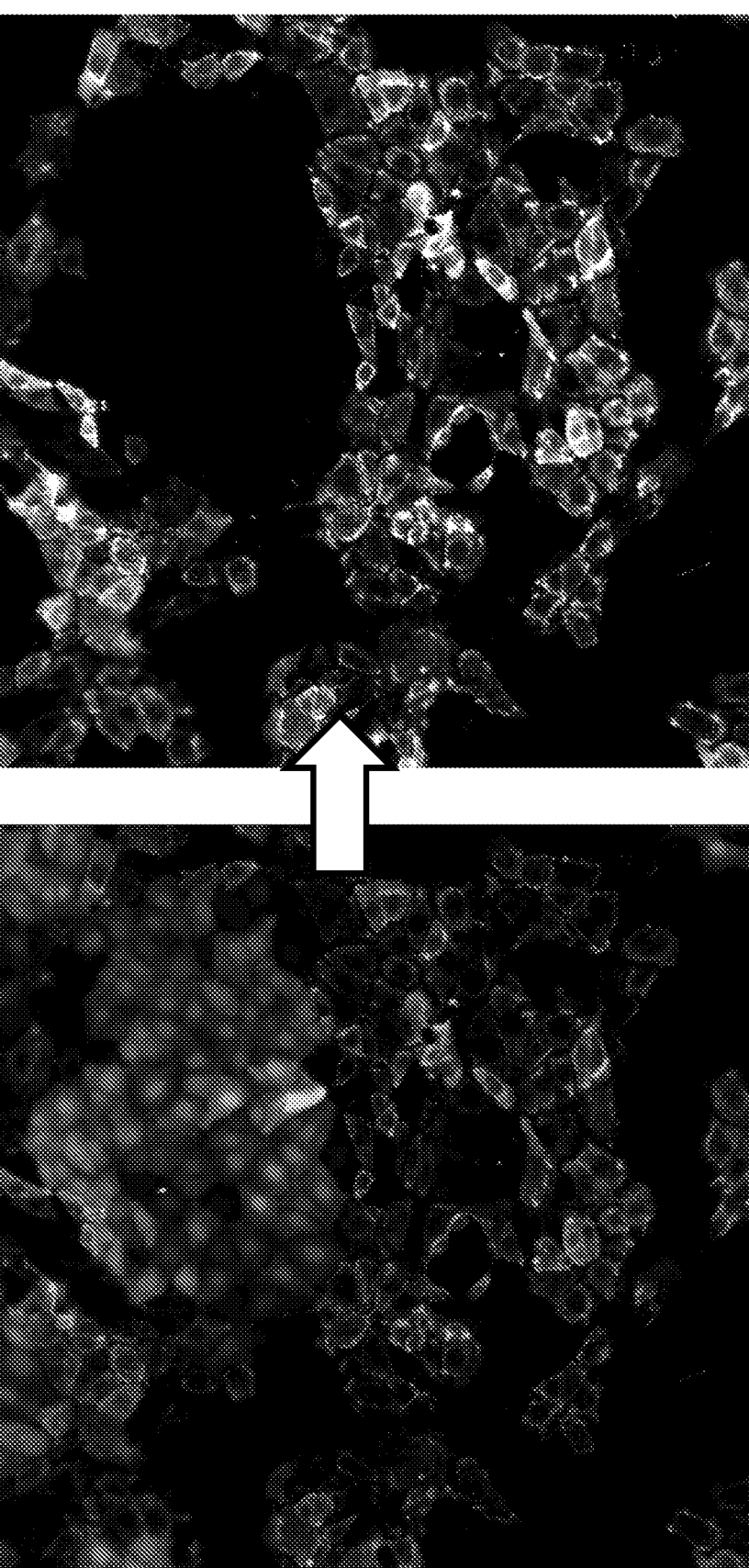
FIG. 3. Immunofluorescence imaging of an antibody from hybridoma DG1A11 on live cells. The left panel shows antibody binding to DG-expressing cells but not to DG-deficient cells. The right panel is the same image with the channel showing DG-deficient cells removed and the channel showing antibody binding to DG-expressing cells enhanced.

Example 2. Screening for antibodies of interest by live cell binding and internalization. Antibody activity was measured as binding to the surface of living cells expressing the human DG protein ("positive" cells) but not to negative controls (cells derived from an engineered conditional DG knockout mouse lacking human DG expression). The positive population was the same cell line used for immunization, MEpG cells expressing the human DG protein. The negative population was the murine MEpG line expressing green fluorescent protein (GFP) and not the human DG protein, created as previously described in Oppizzi et al., Traffic, 9(12): 2063-2072, 2008. The positive and negative populations were co-cultured in wells of Ibidi 96-well micro-plates (Ibidi, catalog #89626) and distinguishable by GFP expression. Hybridoma supernatants to be tested were diluted 1:1 with plain DMEM:F12 cell culture medium (Gibco) and added to cell-containing wells of the 96-well Ibidi plates. Each well was incubated for 60 minutes at 37° C. with the hybridoma supernatants to be tested, washed with DMEM:F12 medium, and incubated 30 minutes at 37° C. with an anti-mouse secondary antibody conjugated to the Alexa-568 fluorescent dye (Jackson Immunochemicals) diluted 1:1000 in DMEM:F12 medium. Lastly, each well was washed with DMEM:F12 medium, fixed with 10% formalin for 30 minutes, stained 5 minutes with DAPI dye diluted in phosphate buffered saline (PBS) plus 0.1% Triton X-100, washed with PBS and screened by automated imaging of the blue (DAPI), green (GFP) and red (Alexa-568) channels using an IN Cell Analyzer 6000 cell imaging system from General Electric. Hybridoma supernatants considered to have good activity were those that demonstrated selective staining of the positive (human DG-expressing) cells in the red channel and not for the control GFP-expressing cells (detected in green channel) as shown in FIG. 3. These clones were further propagated and re-screened by the same methods.

Figure 4:
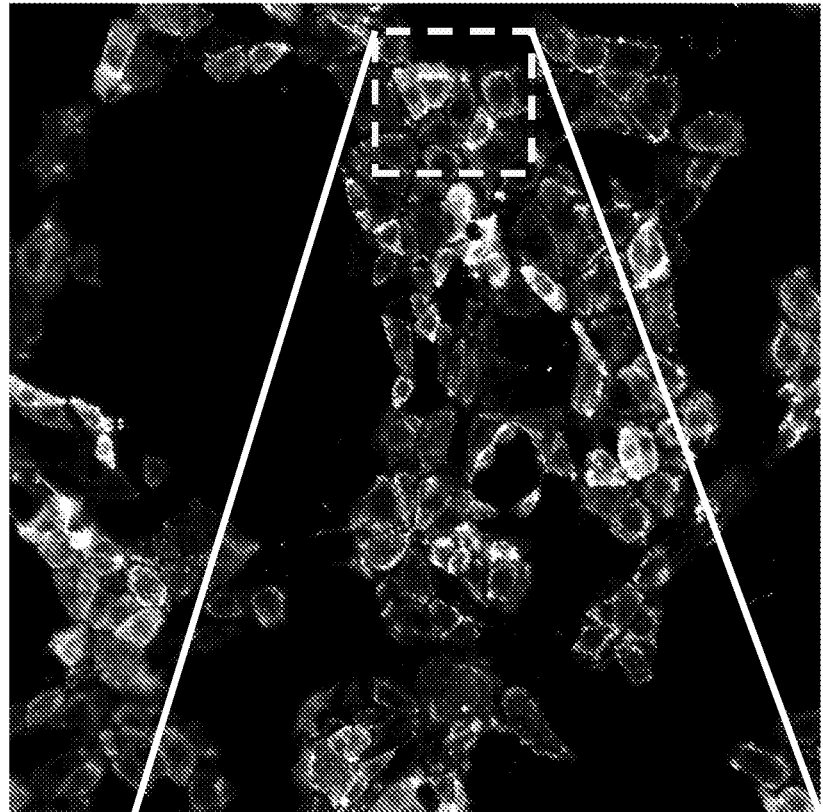
FIG. 4. Immunofluorescence imaging of an antibody from hybridoma DG1A11 on live cells. Enlarged region (left) shows internalization of the antibody into endocytic vesicles that populate the cytoplasm but are excluded from the nucleus.
Figure 4:
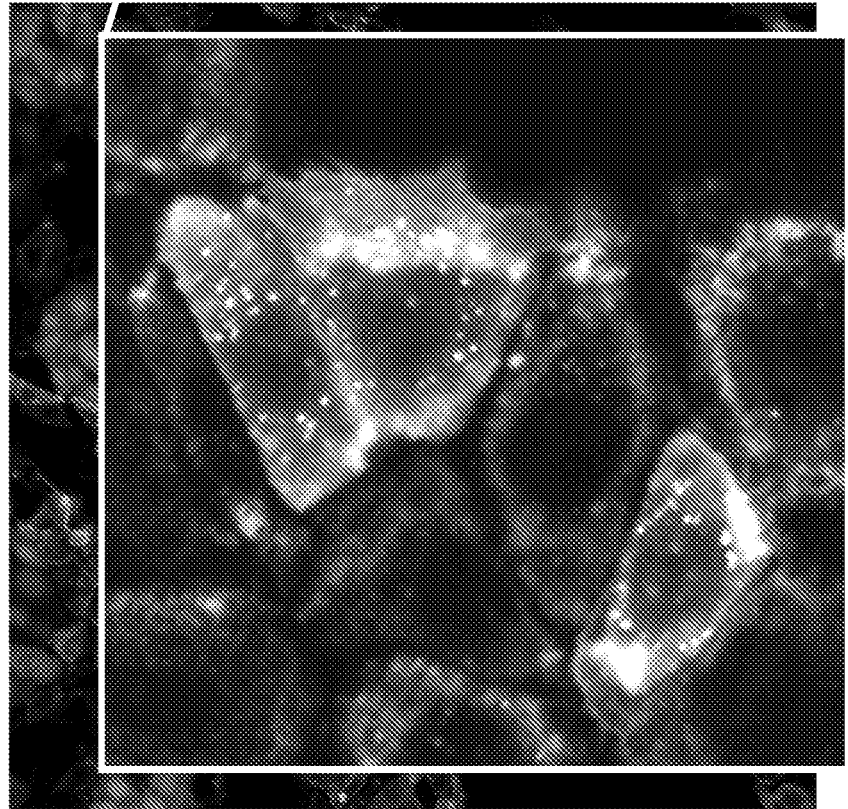

The live cell staining method employed to test for cell binding in the initial hybridoma supernatant screen was also employed to test for internalization of the bound antibodies into endocytic vesicles. This was achieved using the same methods described above with a modification that the immunostained living cells were allowed to incubate in culture for longer times (2 to 4 hours longer) prior to fixation in formalin or kept alive for live cell imaging. With longer incubation times, the bound antibodies have an extended opportunity to enter the endocytic pathway and accumulate in endocytic vesicles. Internalization of antibodies into endocytic vesicles is recognizable as the accumulation of discrete fluorescent foci in the cellular cytoplasm that is excluded from the nucleus, as shown in FIG. 4. With live cell imaging, these foci are observed to be highly mobile and rapidly move about the cell cytoplasm, as is characteristic of endocytic vesicles.

Example 3. Antibody sequencing. Stable positive clones were propagated and 200 mL of hybridoma supernatant from each was then subject to affinity column purification using protein G (ThermoFisher Scientific, cat #20397) according to the manufacturer's protocol. Purified antibody proteins were submitted for amino acid sequencing with Rapid Novor (Ontario, Canada).

Example 4. Immunoprecipitation studies with candidate antibodies. Immunoprecipitation is another method to test antibody recognition of a designated target. DG is presented on the cell surface as a non-covalently bound heterodimer composed of the transmembrane β-DG subunit and the extracellular α-DG subunit. Immunoblotting and immunoprecipitation of DG have been reported for many cell lines, and it has been shown that the β-DG appears at a mass of 42 kDa and the α-DG subunit appears at a broad mass range of 100 kDa to 180 kDa (e.g., see Singh et al., Cancer Research, 64(17):6152-6159, 2004). The highly variable mass of α-DG results from highly variable glycosylation (Singh et al., Cancer Res., 64(17):6152-6159, 2004).

Cell surface biotinylation and immunoprecipitation methods employed here followed protocols as reported in Singh et al., (Cancer Res., 64(17):6152-6159, 2004). Cells cultured in 100-mm dishes were washed twice with ice-cold PBS and then incubated with 0.25 mg/ml of NHSPEO$_4$-biotin in PBS for 30 min. at room temperature. Subsequently, cells were washed three times with PBS and then lysed in immunoprecipitation buffer [50 mmol/L Tris-HCl (pH 7.4), 100 mmol/L NaCl, 0.1% (v/v) Nonidet P-40, 1 mmol/L dithiothreitol, 1 mmol/L phenylmethylsulfonyl fluoride, and protease inhibitor mixture]. Cleared lysate was incubated with monoclonal antibodies overnight at 4° C., followed by the addition of protein A/G-agarose beads (Pierce, cat #20423) and a further incubation for 3 hours with continuous rocking at 4° C. The beads were subsequently washed three times with immunoprecipitation buffer, directly resuspended in protein gel sample buffer, boiled, and processed for SDS-PAGE and immunoblotting for proteins conjugated with biotin using HRP-conjugated streptavidin and imaged by chemiluminescence.

The selected hybridoma clones were tested for their ability to immunoprecipitate the human DG protein expressed in the murine MEpG cells. Six selected hybridoma supernatants were tested along with a commercially available DG antibody as a positive control, anti-β-DG clone 4F7 (Santa Cruz Biotechnologies, catalog #sc33702). The results of these immunoprecipitations are shown in FIG. 1. The positive control (lane Ab+) produced a weak but detectable signal, showing the 42 kDa β-DG band and the typical, wide α-DG band ranging from 140-180 kDa. Three of the tested hybridomas (DG1A11 (A), DGH6 (E) and DG4H4 (F)) also showed immunoprecipitation of these same characteristic dual bands, with DG1A11 and DG4H4 being particularly strong, and stronger than the positive control antibody (+Ab). DGH6 produced a weaker signal, but comparable to the positive control.

Figure 2:
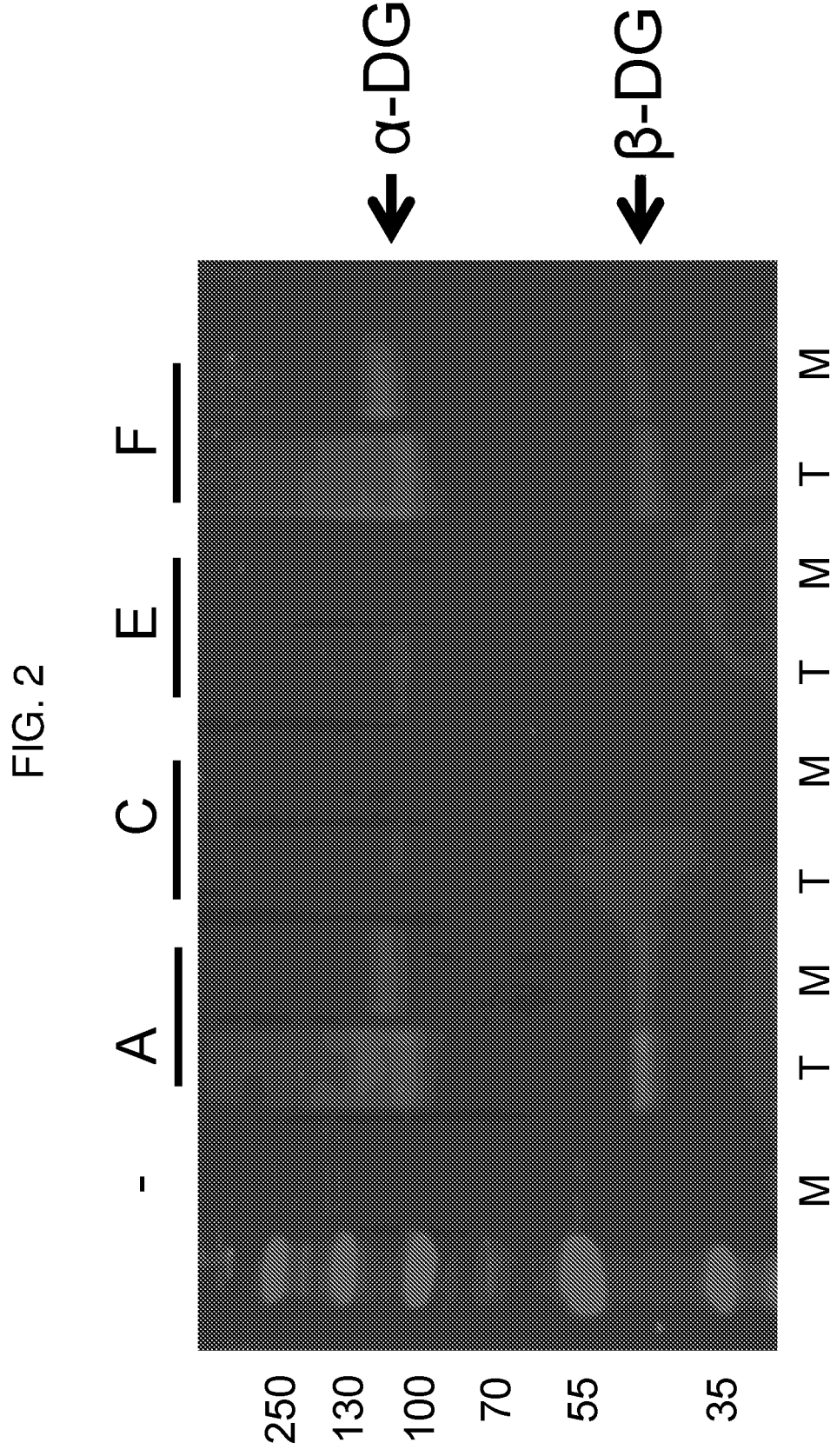
FIG. 2. Immunoprecipitation assays of an antibody from hybridoma DG1A11 (pair of lanes labeled A), candidate clone C (pair of lanes labeled C), an antibody from hybridoma DGH6 (pair of lanes labeled E), and an antibody from hybridoma DG4H4 (pair of lanes labeled F) with DG heterodimer. M=MDA MB 231 human breast cancer cell line. T=T47D human breast cancer cell line. Different cancer cell lines have DG with differing degrees of glycosylation, as revealed by the variable mass of the α-DG subunit between the T47D and MDA-MB-231 cells.

The binding of four selected antibodies to human DG was also tested directly on human cells by immunoprecipitation. At the same time, it was tested whether their binding was sensitive to variable DG glycosylation. Human cancer cell lines have been demonstrated to present DG at their cell surface in variable forms resulting from large variations in α-DG glycosylation (Singh et al., Cancer Res., 64(17):6152-6159, 2004). Two such cell lines are the breast cancer cell lines MDA-MB-231 and T47D which exhibit low and high levels of α-DG glycosylation, respectively (Singh et al., Cancer Res., 64(17):6152-6159, 2004 and Muschler et al., Cancer Res., 62(23):7102-7109, 2002). In FIG. 2, immuno-precipitations from these two cell lines showed that antibodies from hybridomas DG1A11 and DG4H4 immunoprecipitated the β-DG and α-DG proteins from both the MDA-MB-231 cells (M) and the T47D cells (T). The broad variations in the mass of the alpha-DG bands immunoprecipitated by antibodies from hybridomas DG1A11 and DG4H4 reveal that these antibodies can bind to human DG isoforms with highly variable glycosylation. The antibody from hybridoma DGH6 performed weakly, as in FIG. 1, but immunoprecipitated detectable DG heterodimers from the T47D cells. Clone C produced no detectable immunoprecipitation signal, as did the negative control (–) which omitted any antibody.

Figure 5:
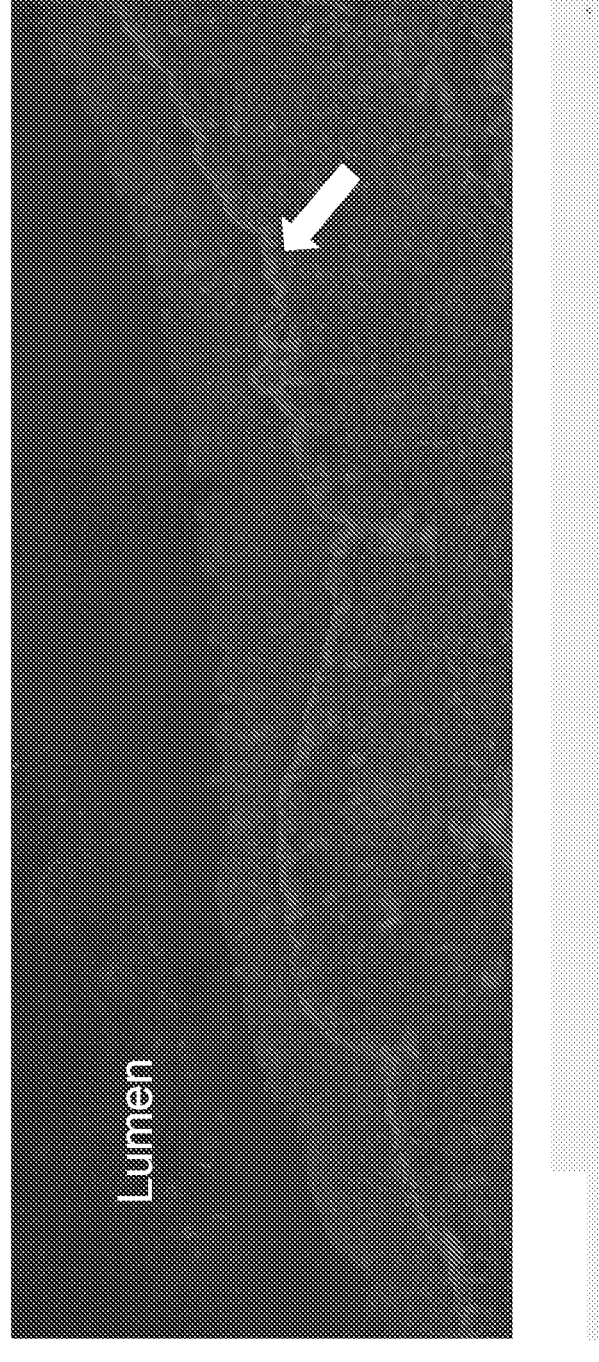
FIG. 5. DG immunostaining in the normal human bladder urothelium shows DG polarization and confinement to the basolateral surface (arrow), and restriction from the lumenal surface (i.e. the bladder lumen).
Figure 5:
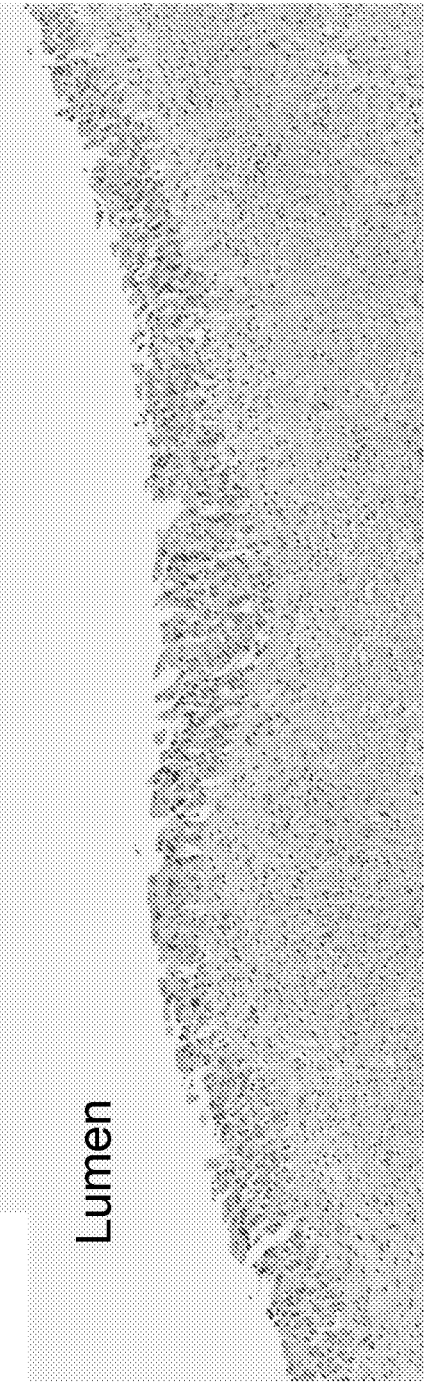

Example 5. DG immunostaining studies of normal bladder tissue. Immunostaining of tissue sections has shown DG to be localized to the basolateral surface of epithelial cell layers. Immunostaining of the normal bladder epithelium of the human bladder shows this same distribution (FIG. 5). In this method adjacent sections of formalin fixed and paraffin embedded (FFPE) human bladder tissue were either stained by Hematoxylin and Eosin (H&E), using standard histochemical methods, or immunostained for DG using standard immunochemical methods. Specifically, immunostaining was performed by tissue de-paraffinization in xylene, followed by re-hydration, pressure cooker for 30 minutes in DAKO buffer (PH 8.0), and blocked in blocking buffer (2% BSA, 1% horse serum and 0.5% Tween 20 in PBS) for 1 hour. The anti-DG antibody clone 4F7 (Santa Cruz, #SC-33702) was diluted 1:25 in blocking buffer and incubated on the slide overnight at 4° C. The slide was them washed in PBS, incubated with the fluorescently labeled anti-mouse secondary for 1 hour at room temperature (RT), washed with PBS and mounted under a glass coverslip in mounting medium containing DAPI. The slide was imaged on a ZEISS Axio Scan.Z1 slide scanner.

Figure 6:
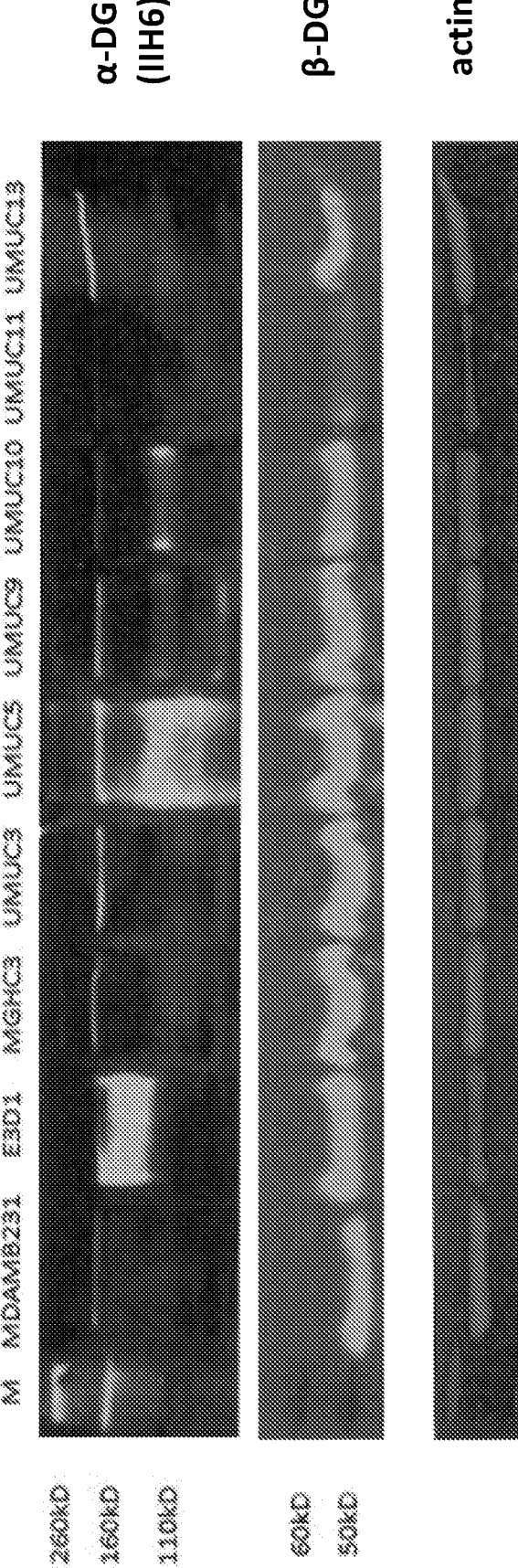
FIG. 6. Immunoblot of α-DG and β-DG from cell lines using a commercial antibody (clone IIH6, Millipore Sigma, Burlington, MA). MGHC3, UMUC3, UMUC5, UMUC9, UMUC10, UMUC11, and UMUC13 are human bladder cancer cell lines; MDA-MB-231 is a human breast cancer cell line; and E3D1 is a normal murine breast epithelial cell line. M=molecular mass marker.

Example 6. Detection of antibody binding and internalization in human bladder cancer cells displaying variable α-DG glycosylation. DG is expressed in all carcinoma cell lines tested, although the glycosylation state is highly variable (see, e.g., Akhavan et al., Cancer Res., 72(10):2578-2588, 2012). Immunoblotting of bladder cancer cell lines shows expression of the DG protein in all cell lines tested, as detected by immunoblotting for the β-DG subunit (FIG. 6). The cell lines included seven human bladder cancer cell lines (MGHC3, UMUC3, UMUC5, UMUC9, UMUC10, UMUC11, and UMUC13), the human breast cancer cell line MDA-MB-231, and a normal murine breast epithelial cell line E3D1, with the molecular mass marker (M) run in the far left lane. Immunoblotting for β-actin (FIG. 6, actin) shows similar protein loading on the gel, although lower protein loading for the UMUC11 cells. Immunoblotting for α-DG was performed using a commercial antibody (clone IIH6, Millipore Sigma, Burlington, MA) that is sensitive to glycosylation levels and fails to detect α-DG when DG is hypo-glycosylated (Hara et al., Proc Natl Acad Sci, 108: 17426-17431, 2011). This antibody strongly detects the α-DG glycoprotein only in the E3D1 and UMUC5 cells, seen as a broad band of variable mass, reflecting variable glycosylation. A relatively weak signal was detected in the UMUC9 and UMUC10 cells, and no signal was detected in MDA-MD-231, MGHC3, and UMUC3 cells. Immunoblots were performed as described in Leonoudakis et al., J. Cell Science, 127:4894-4903, 2014.

Figure 7:
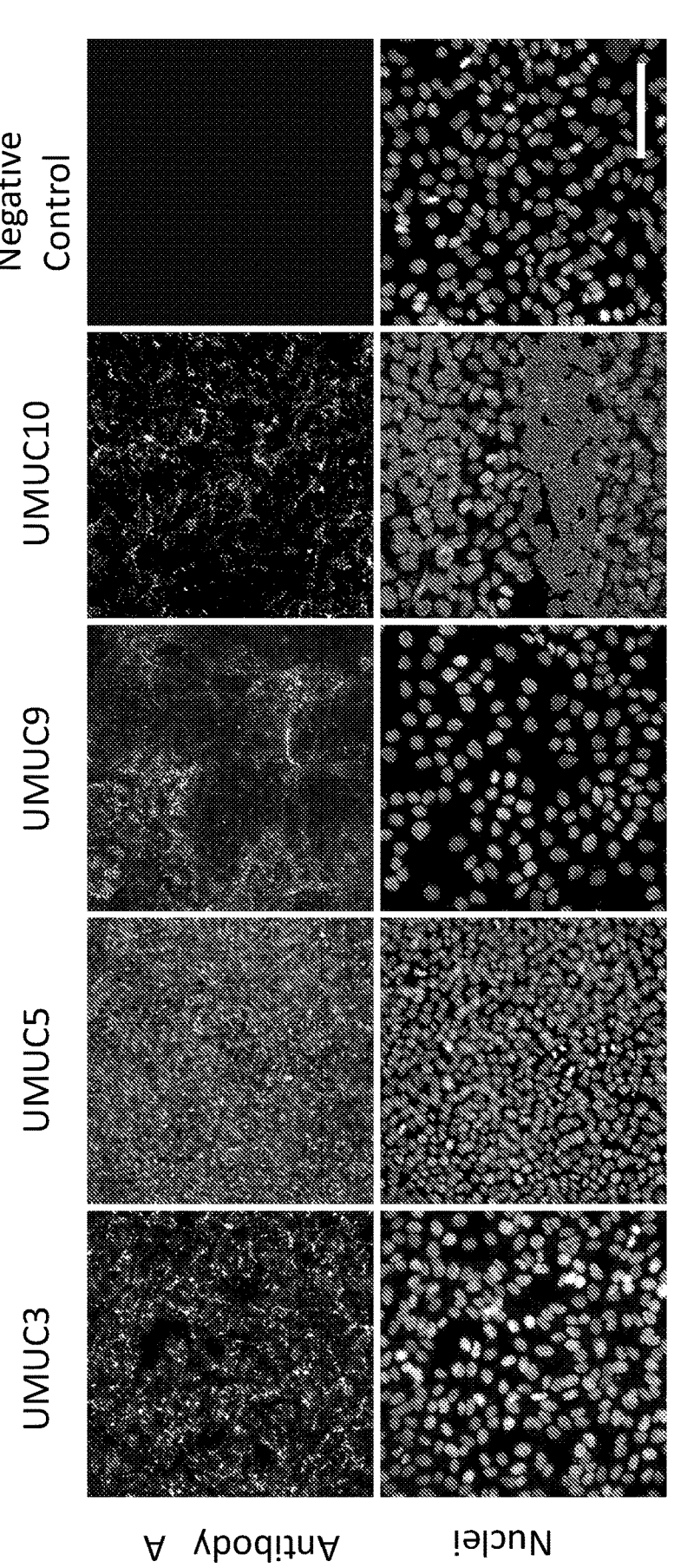
FIG. 7. Immunofluorescence imaging of an antibody from hybridoma DG1A11 on live cells. The top panels show the antibody from hybridoma DG1A11 ('Antibody A') binding to DG on human bladder cancer cell lines but no binding by a negative control antibody. The bottom panels show staining of nuclei by DAPI in the cancer cells and in the negative control. UMUC3, UMUC5, UMUC9, and UMUC10 are human bladder cancer cell lines.
Figures 8A, 8B, 8C:
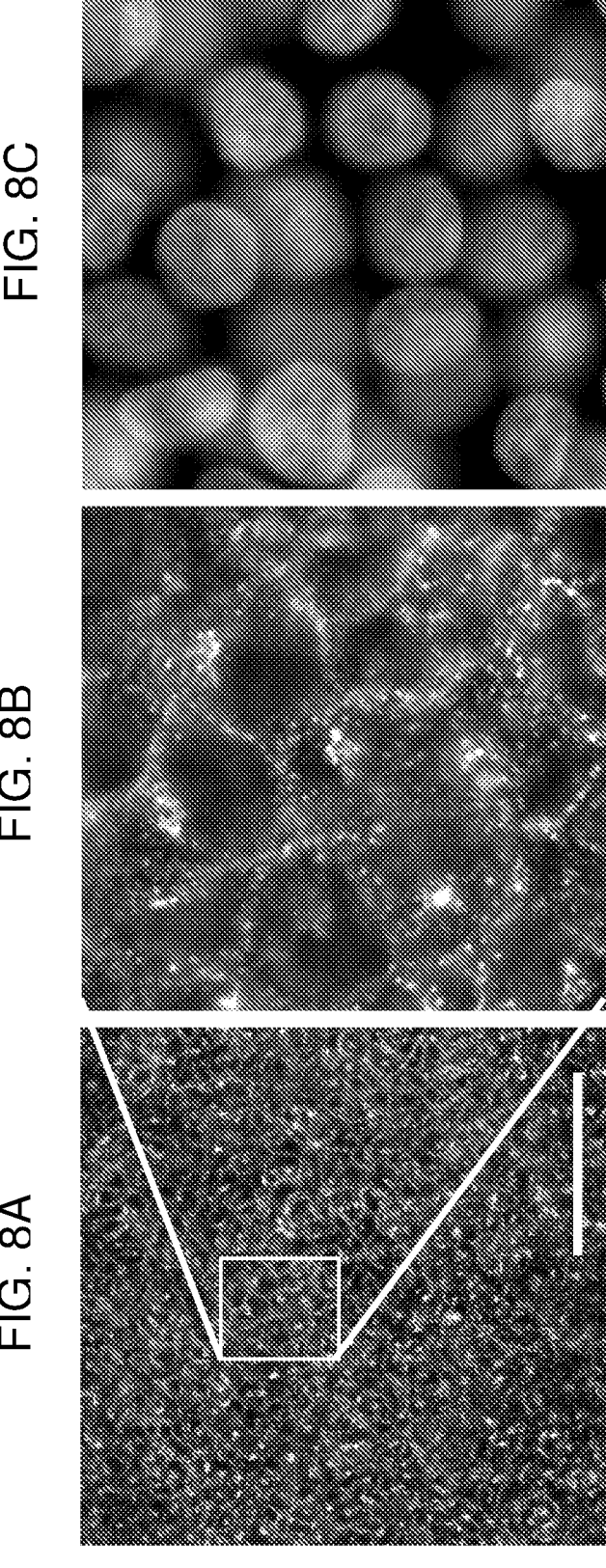
FIGS. 8A-8C. Immunofluorescence imaging of an antibody from hybridoma DG1A11 on live cells.
Figure 9:
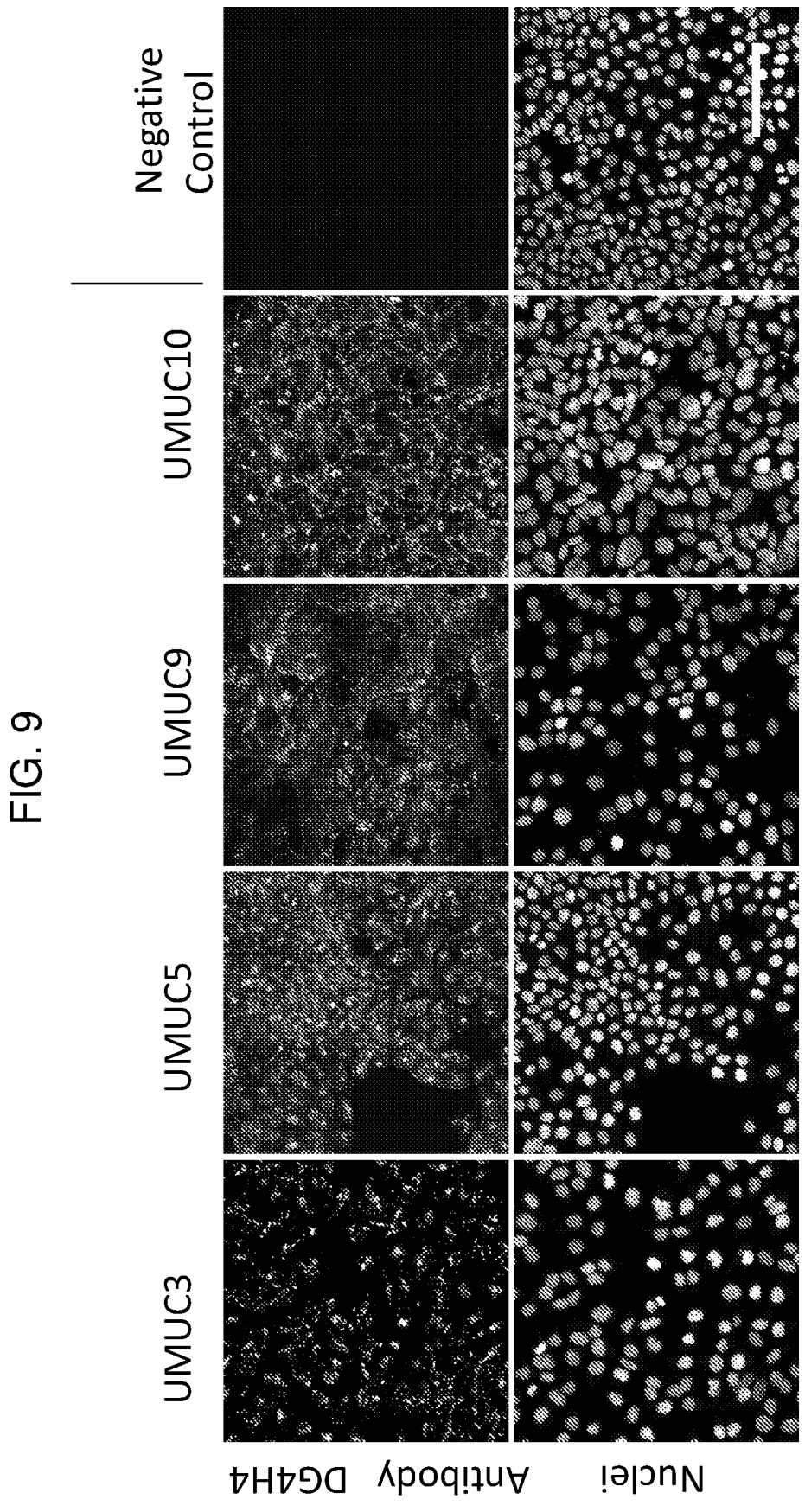
FIG. 9. Immunofluorescence imaging of an antibody from hybridoma DG4H4 on live cells. The top panels show the antibody from hybridoma DG4H4 binding to DG on human bladder cancer cell lines but no binding by a negative control antibody. The bottom panels show staining of nuclei by DAPI in the cancer cells and in the negative control. UMUC3, UMUC5, UMUC9, and UMUC10 are human bladder cancer cell lines.

Binding and internalization of the anti-DG antibodies disclosed herein was tested in human bladder cancer cells. Established cell lines UMUC3, UMUC5, UMUC9 and UMUC10 were tested as described in Example 2 (and FIGS. 3 and 4) and imaged. FIG. 7 shows the positive detection of antibody binding and internalization in all four bladder cancer cell lines after incubation of antibody from hybridoma DG1A11 ('antibody A') with the 4 cell lines, relative to negative controls. The negative controls use the fluorescenated secondary antibody alone, omitting the primary antibody. FIGS. 8A-8C show a higher magnification view of the UMUC5 cells shown in FIG. 7 with clearly visible endocytic vesicle labeling by the internalized antibody.

As also seen previously in FIG. 4 in Example 2, the internalization of antibodies into endocytic vesicles is recognizable as the accumulation of discrete fluorescent foci in the cellular cytoplasm that is excluded from the nucleus. With live cell imaging, these foci are observed to be highly mobile and rapidly move about the cell cytoplasm, as is characteristic of endocytic vesicles. The antibody from hybridoma DG4H4 also shows binding and internalization in these same cell lines (FIGS. 9, and 10A-10C). The negative controls use the fluorescenated secondary antibody alone, omitting the primary antibody. Comparable testing for the antibody from hybridoma DGH6 is pending.

Example 7 (prophetic). Immunostaining of DG localization in bladder cancer tissues using the disclosed anti-DG antibodies. Immunostaining of DG localization will be performed in human bladder carcinoma in situ (CIS) samples and in human micropapillary urothelial (MPUCs) samples derived from FFPE fixed human specimens. This will be performed by the same methods described as in Example 5 (FIG. 5).

Example 8 (prophetic). Molecular imaging of bladder cancer tissue ex vivo. Molecular imaging of bladder cancer tissue ex vivo as described previously (Pan et al., Sci Transl. Med., 6(260): 148, 2014) will be performed with the disclosed anti-DG antibodies. Briefly, the disclosed anti-DG antibodies can be labeled with a fluorescent tag such as a quantum dot. Radical cystectomy will be performed to obtain an intact bladder. After radical cystectomy, an ex vivo intact bladder will be instilled with a fluorescently labeled anti-DG antibody via a urinary catheter. The fluorescently labeled anti-DG antibody will be incubated for 30 min to allow antibody binding. The labeled bladder will be irrigated with saline and any bound anti-DG antibody will be detected by endoscopic imaging of the bladder mucosa. Normal and suspicious regions can be biopsied for histopathological analysis.

Example 9 (prophetic). In vivo studies using the disclosed anti-DG antibodies. For in vivo studies, the antibody will be conjugated to a fluorophore or to a positron-emitting radio-ligand, then instilled into the bladder by catheterization. Ten to twenty mg of antibody-conjugate will be diluted in 50 mL of PBS, instilled in the bladder, and allowed to reside there for two hours, similar to methods described by Kowalski et al., *J Urol.* 188(5):1712-1718, 2012. In vivo studies can also be conducted in the bladder of living monkeys with or without bladder cancer or pre-cancerous lesions. These studies will include intravesicular exposure of a radiolabeled anti-DG antibody, followed by positron emission tomography (PET) imaging. In vivo studies can also be conducted in a clinical trial, for example as a phase 0 study in human bladder cancer patients, using fluorescence detection or positron-emission tomography (PET) imaging of the anti-DG antibodies. Ultimately clinical trials of therapeutic efficacy will be performed in human patient cohorts using antibody-drug conjugates, similar to work described by Kowalski et al., *J Urol.* 188(5):1712-1718, 2012.

Example 10. Detection of antibody binding and internalization in human T cells. Binding and internalization of anti-DG antibodies disclosed herein (the antibodies produced from hybridomas DG1A11 and DG4H4) were tested in human T cells. The antibodies were readily internalized into Jurkat cells, demonstrating that anti-DG antibodies disclosed herein are able to bind DG on the surface of and be internalized into non-epithelial cells.

Live Jurkat T-cells were incubated with the anti-DG and negative control antibodies diluted in Jurkat cell culture medium inside a $CO_2$-controlled cell culture incubator at 37° C. The primary antibodies were incubated with the cells for 40 minutes, then washed with plain medium by centrifugation and medium replacement to remove the unbound primary antibodies. The cells were then exposed to an anti-mouse secondary antibody conjugated to Alexa-568, diluted in Jurkat cell culture medium. These antibody-cell mixtures were placed in a cell culture incubator and incubated for 6 hours before washing away the unbound secondary antibodies. A subset of these treated cells were then treated for 20 minutes at 37° C. with a 0.25% trypsin solution to digest away bound antibodies remaining on the external cell surface. All treated cells were then transferred to a multi-well glass-bottomed plate for imaging using an InCell Analyzer 6000.

Figures 11A, 11B, 11C:
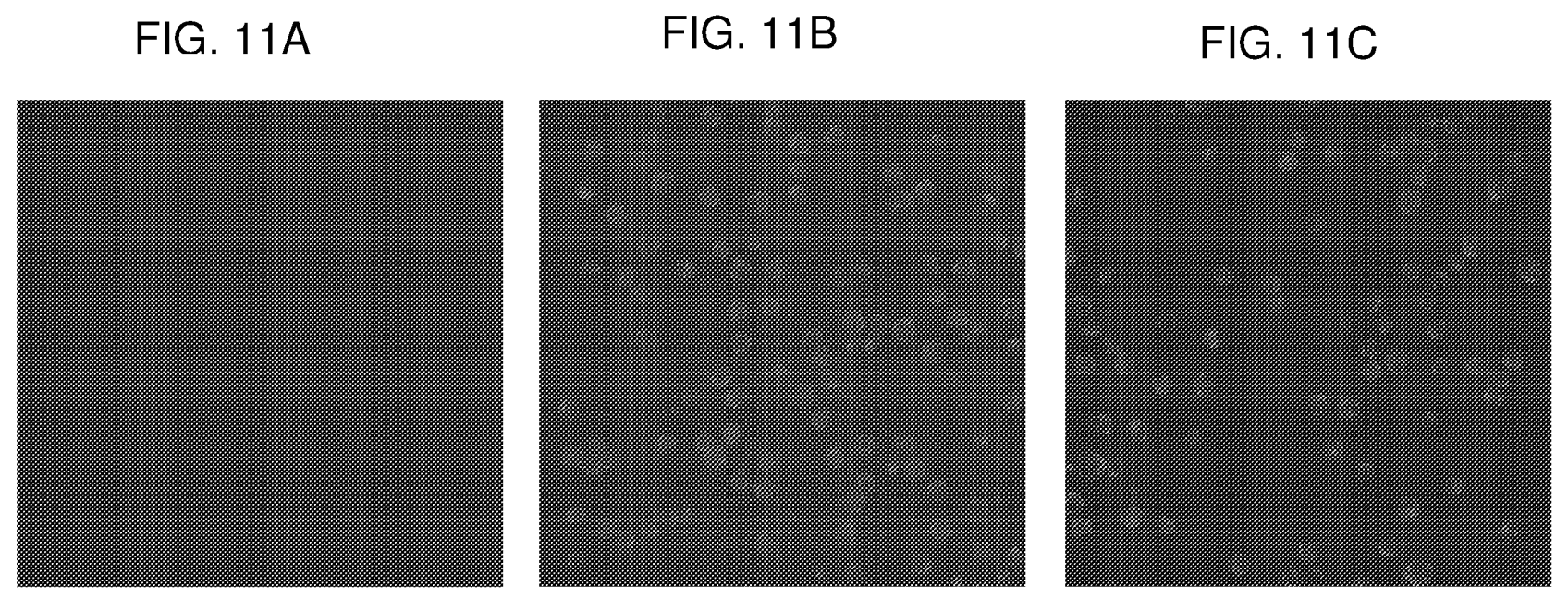
Figures 12A, 12B:
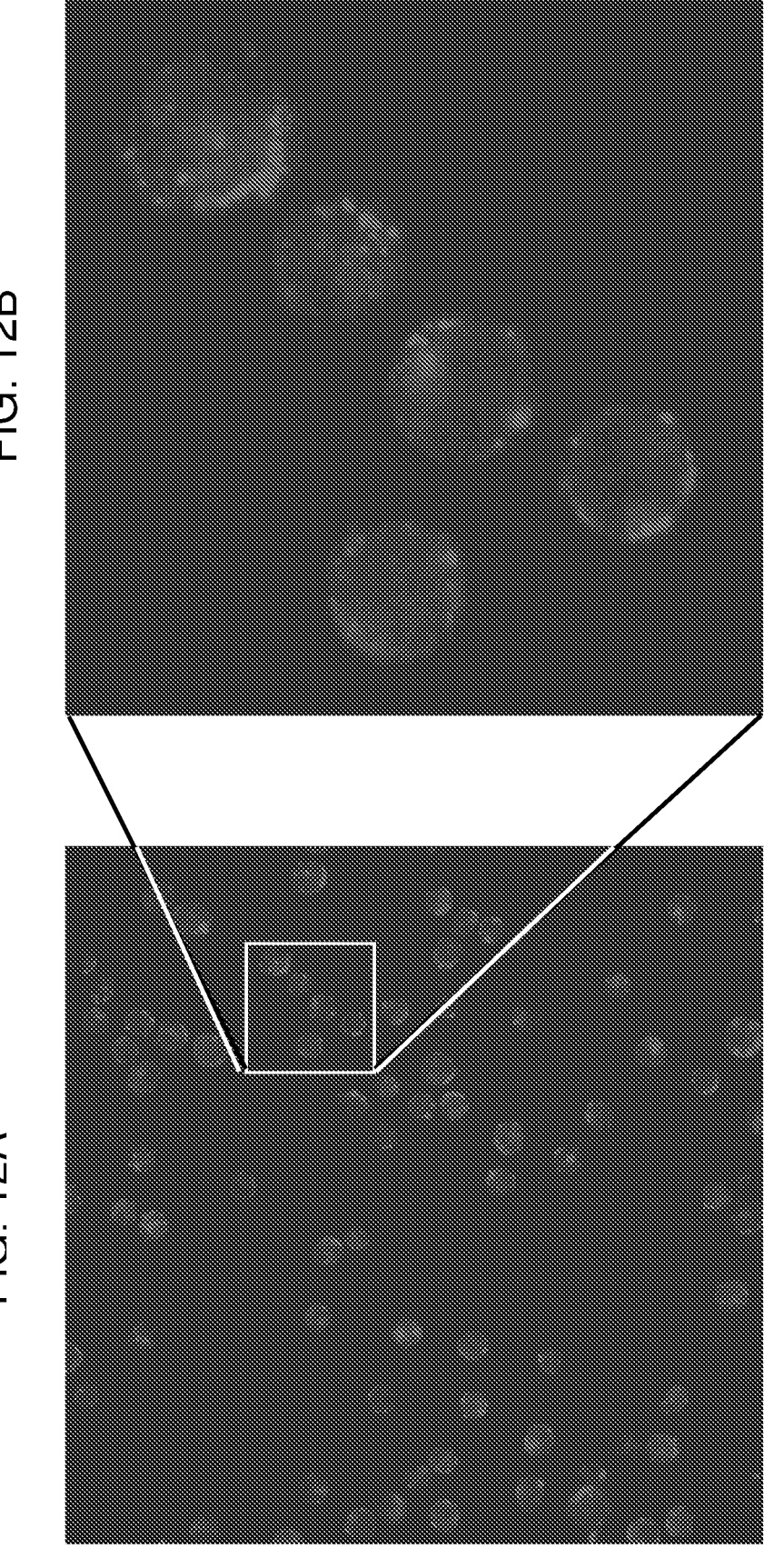
FIGS. 12A, 12B. Immunofluorescence imaging of binding and internalization of an antibody from hybridoma DG1A11 in live Jurkat cells.
Figures 13A, 13B:
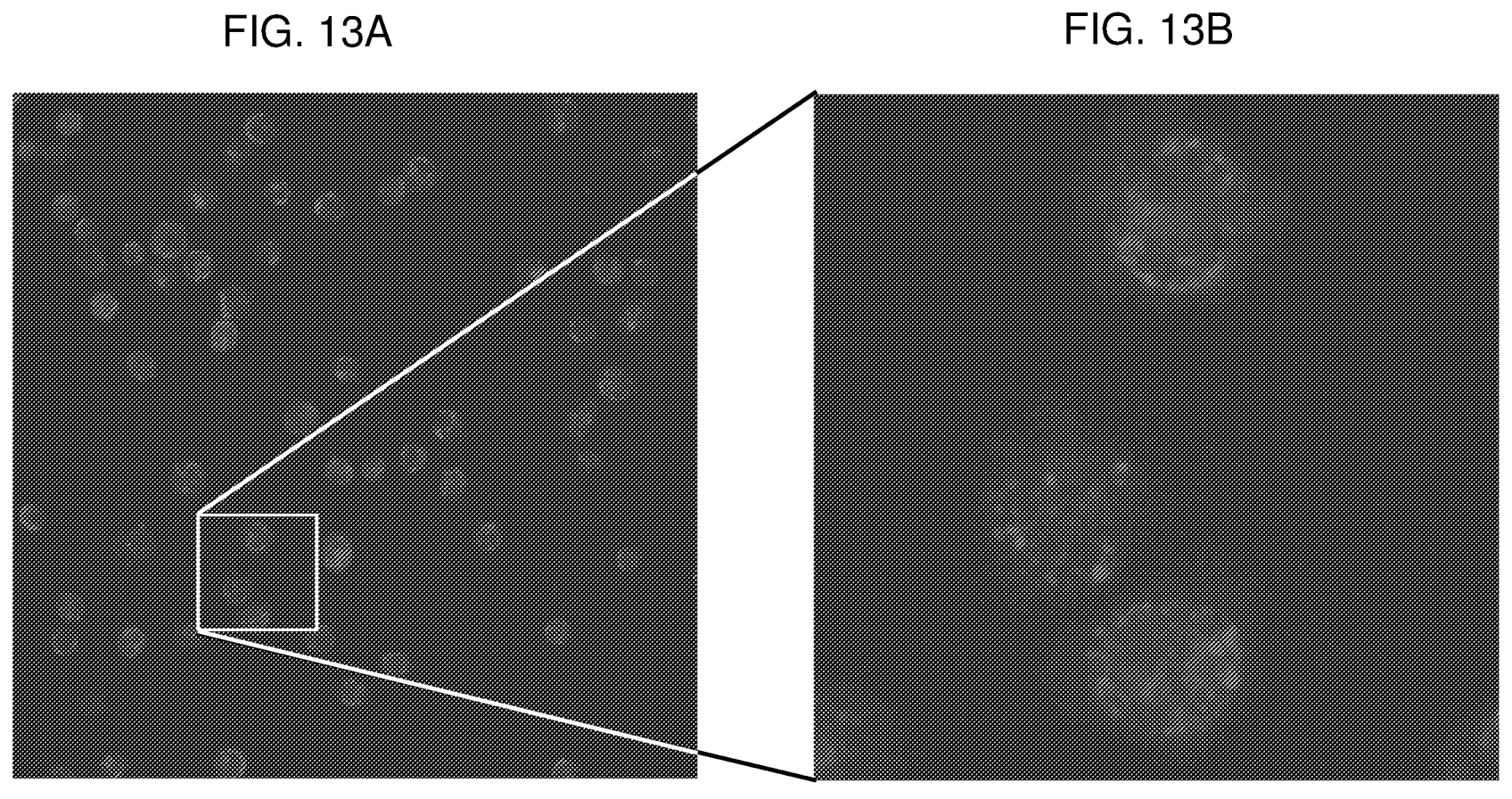

FIGS. 11A-11C show the positive detection of antibody binding and internalization in Jurkat cells after incubation of antibody from hybridoma DG1A11, relative to a negative control. The negative control used the fluorescenated secondary antibody alone, omitting the primary antibody. FIGS. 12A, 12B show a higher magnification view of the Jurkat cells shown in FIG. 11C with clearly visible endocytic vesicle labeling by the internalized antibody. The antibody from hybridoma DG4H4 also shows binding and internalization in Jurkat cells (FIGS. 13A, 13B). Treatment with trypsin in live cells removes all surface-bound antibodies (FIGS. 11C, 12A, 12B, 13A, 13B).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in the ability to target a payload to a cell using one of the disclosed antibodies or an antigen-binding fragment thereof.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

---

I claim:

1. An isolated antibody or antigen-binding fragment thereof that binds to dystroglycan (DG), comprising:
 a heavy chain comprising:
  CDRH1 comprising SEQ ID NO: 1,
  CDRH2 comprising SEQ ID NO: 2, and
  CDRH3 comprising SEQ ID NO: 3;
   and a light chain comprising:
  CDRL1 comprising SEQ ID NO: 4,
  CDRL2 comprising SEQ ID NO: 5, and
  CDRL3 comprising SEQ ID NO: 6;
 a heavy chain comprising:
  CDRH1 comprising SEQ ID NO: 11,
  CDRH2 comprising SEQ ID NO: 12, and
  CDRH3 comprising SEQ ID NO: 13;
   and a light chain comprising:
  CDRL1 comprising SEQ ID NO: 14,
  CDRL2 comprising SEQ ID NO: 15, and
  CDRL3 comprising SEQ ID NO: 16;
or
 a heavy chain comprising:
  CDRH1 comprising SEQ ID NO: 21,
  CDRH2 comprising SEQ ID NO: 22, and
  CDRH3 comprising SEQ ID NO: 23;
   and a light chain comprising:
  CDRL1 comprising SEQ ID NO: 24,
  CDRL2 comprising SEQ ID NO: 25, and
  CDRL3 comprising SEQ ID NO: 26;
wherein the binding is independent of variable DG glycosylation.

2. The isolated antibody or antigen-binding fragment thereof of claim 1, comprising:
 a variable heavy (VH) domain comprising SEQ ID NO: 7 and a variable light (VL) domain comprising SEQ ID NO: 9; or
 a heavy chain comprising SEQ ID NO: 8 and a light chain comprising SEQ ID NO: 10.

3. The isolated antibody or antigen-binding fragment thereof of claim 1, comprising:
 a variable heavy (VH) domain comprising SEQ ID NO: 17 and a variable light (VL) domain comprising SEQ ID NO: 19; or
 a heavy chain set forth in SEQ ID NO: 18 and a light chain comprising SEQ ID NO: 20.

4. The isolated antibody or antigen-binding fragment thereof of claim 1, comprising:
 a variable heavy (VH) domain comprising SEQ ID NO: 27 and a heavy chain comprising SEQ ID NO: 28; or
 a variable light (VL) domain comprising SEQ ID NO: 29 and a light chain comprising SEQ ID NO: 30.

5. The isolated antibody or antigen-binding fragment thereof of claim 1, comprising:
 a heavy chain encoded by SEQ ID NO: 31;
 a light chain encoded by SEQ ID NO: 33; or
 both a heavy chain encoded by SEQ ID NO: 31 and a light chain encoded by SEQ ID NO: 33.

6. The isolated antibody or antigen-binding fragment thereof of claim 1, comprising:
 a heavy chain encoded by SEQ ID NO: 35;
 a light chain encoded by SEQ ID NO: 37; or
 both a heavy chain encoded by SEQ ID NO: 35 and a light chain encoded by SEQ ID NO: 37.

7. The isolated antibody or antigen-binding fragment thereof of claim 1, comprising:
 a heavy chain encoded by SEQ ID NO: 39;
 a light chain encoded by SEQ ID NO: 41; or
 both a heavy chain encoded by SEQ ID NO: 39 and a light chain encoded by SEQ ID NO: 41.

8. The isolated antibody or antigen-binding fragment thereof of claim 1, which is produced by hybridoma DG1A11.

9. The isolated antibody or antigen-binding fragment thereof of claim 1, which is produced by hybridoma DGH6.

10. The isolated antibody or antigen-binding fragment thereof of claim 1, which is produced by hybridoma DG4H4.

11. The isolated antibody or antigen-binding fragment thereof of claim 1, which binds to DG that is expressed on a surface of a living cell.

12. The isolated antibody or antigen-binding fragment thereof of claim 1, wherein the DG is human or non-human primate.

13. A pharmaceutical composition comprising:
 the antibody or antigen-binding fragment thereof of claim 1 covalently or non-covalently bound to one or more payloads; and
 a pharmaceutically acceptable carrier.

14. The pharmaceutical composition of claim 13, wherein the one or more payloads are covalently or non-covalently bound directly or indirectly to the antibody or antigen-binding fragment thereof of claim 1.

15. The pharmaceutical composition of claim 14, wherein the one or more payloads comprises a fluorescent tag, a bioluminescent tag, a chemiluminescent tag, a nucleic acid, a nucleic acid barcode, an affinity tag, an enzyme, a radioisotope, a magnetic resonance imaging contrast agent, a nanoparticle, a nanoparticle comprising a nucleic acid, a toxin, an mRNA, an siRNA, or a small molecule drug.

16. A kit comprising:
 the antibody or antigen-binding fragment thereof of claim 1; and
 instructions on use of the antibody or antigen-binding fragment thereof to detect DG.

17. The kit of claim 16, wherein the antibody or antigen-binding fragment thereof of claim 1 is conjugated to one or more of a fluorescent tag, a bioluminescent tag, a chemiluminescent tag, a nucleic acid, a nucleic acid barcode, an affinity tag, an enzyme, a radioisotope, a magnetic resonance imaging contrast agent, a nanoparticle, a nanoparticle comprising a nucleic acid, a toxin, an mRNA, an siRNA, or a small molecule drug.

* * * * *

SEQUENCE LISTING

```
<160> NUMBER OF SEQ ID NOS: 65

<210> SEQ ID NO 1
<211> LENGTH: 8
<212> TYPE: PRT
<213> ORGANISM: Artificial Sequence
<220> FEATURE:
<223> OTHER INFORMATION: CDRH1 for antibody from hybridoma DG1A11

<400> SEQUENCE: 1

Asp Tyr Ala Ile Thr Ser Asp Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: CDRH2 for antibody from hybridoma DG1A11

<400> SEQUENCE: 2

Ser Tyr Ser Gly Ser
1               5

<210> SEQ ID NO 3
<211> LENGTH: 13
<212> TYPE: PRT
<213> ORGANISM: Artificial Sequence
<220> FEATURE:
<223> OTHER INFORMATION: CDRH3 for antibody from hybridoma DG1A11

<400> SEQUENCE: 3

Ala Ala Pro Phe Thr Thr Leu Thr Asp Phe Phe Asp Tyr
1               5                   10
```

-continued

<210> SEQ ID NO 4
<211> LENGTH: 11
<212> TYPE: PRT
<213> ORGANISM: Artificial Sequence
<220> FEATURE:
<223> OTHER INFORMATION: CDRL1 for antibody from hybridoma DG1A11

<400> SEQUENCE: 4

Lys Ala Ser Gln Asp Val Thr Thr Ala Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDRL2 for antibody from hybridoma DG1A11

<400> SEQUENCE: 5

Trp Ala Ser Ser Arg His Thr
1               5

<210> SEQ ID NO 6
<211> LENGTH: 9
<212> TYPE: PRT
<213> ORGANISM: Artificial Sequence
<220> FEATURE:
<223> OTHER INFORMATION: CDRL3 for antibody from hybridoma DG1A11

<400> SEQUENCE: 6

Gln Gln His Tyr Ser Thr Pro Tyr Thr
1               5

<210> SEQ ID NO 7
<211> LENGTH: 122
<212> TYPE: PRT
<213> ORGANISM: Artificial Sequence
<220> FEATURE:
<223> OTHER INFORMATION: VH amino acid sequence for antibody from
      hybridoma DG1A11

<400> SEQUENCE: 7

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ala Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Ser Thr Ser Tyr Ser Ser Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Tyr Cys
                85                  90                  95

Ala Arg Ala Ala Pro Phe Thr Thr Leu Thr Asp Phe Phe Asp Tyr Trp
            100                 105                 110

Gly Gln Gly Thr Thr Leu Thr Val Ser Ser
        115                 120

<210> SEQ ID NO 8
<211> LENGTH: 446
<212> TYPE: PRT
<213> ORGANISM: Artificial Sequence

```
<220> FEATURE:
<223> OTHER INFORMATION: heavy chain amino acid sequence for antibody
      from hybridoma DG1A11

<400> SEQUENCE: 8

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ala Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Tyr Ser Gly Ser Thr Ser Tyr Ser Ser Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Tyr Cys
                85                  90                  95

Ala Arg Ala Ala Pro Phe Thr Thr Leu Thr Asp Phe Phe Asp Tyr Trp
            100                 105                 110

Gly Gln Gly Thr Thr Leu Thr Val Ser Ser Ala Lys Thr Thr Pro Pro
        115                 120                 125

Ser Val Tyr Pro Leu Ala Pro Gly Ser Ala Ala Gln Thr Asn Ser Met
    130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
            165                 170                 175

Ala Val Leu Gln Ser Asp Leu Tyr Thr Leu Ser Ser Ser Val Thr Val
        180                 185                 190

Pro Ser Ser Thr Trp Pro Ser Glu Thr Val Thr Cys Asn Val Ala His
    195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
            245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
    290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
            325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
    370                 375                 380

Gln Pro Ala Glu Asn Tyr Lys Asn Thr Gln Pro Ile Met Asp Thr Asp
```

-continued

```
385              390              395              400

Gly Ser Tyr Phe Val Tyr Ser Lys Leu Asn Val Gln Lys Ser Asn Trp
            405              410              415

Glu Ala Gly Asn Thr Phe Thr Cys Ser Val Leu His Glu Gly Leu His
            420              425              430

Asn His His Thr Glu Lys Ser Leu Ser His Ser Pro Gly Lys
            435              440              445
```

```
<210> SEQ ID NO 9
<211> LENGTH: 107
<212> TYPE: PRT
<213> ORGANISM: Artificial Sequence
<220> FEATURE:
<223> OTHER INFORMATION: VL amino acid sequence for antibody from
      hybridoma DG1A11

<400> SEQUENCE: 9

Asp Ile Val Met Thr Gln Ser His Lys Phe Met Ser Thr Ser Val Gly
1               5               10              15

Asp Arg Val Thr Ile Thr Cys Lys Ala Ser Gln Asp Val Thr Thr Ala
            20              25              30

Val Ala Trp Tyr Gln Gln Lys Pro Gly Gln Ser Pro Lys Leu Leu Ile
            35              40              45

Tyr Trp Ala Ser Ser Arg His Thr Gly Val Pro Asp Arg Phe Thr Gly
    50              55              60

Ser Gly Ser Gly Thr Asp Tyr Thr Leu Thr Ile Ser Ser Val Gln Ala
65              70              75              80

Glu Asp Leu Ala Leu Tyr Tyr Cys Gln Gln His Tyr Ser Thr Pro Tyr
            85              90              95

Thr Phe Gly Gly Gly Thr Lys Leu Glu Ile Lys
            100             105
```

```
<210> SEQ ID NO 10
<211> LENGTH: 214
<212> TYPE: PRT
<213> ORGANISM: Artificial Sequence
<220> FEATURE:
<223> OTHER INFORMATION: light chain amino acid sequence for antibody
      from hybridoma DG1A11

<400> SEQUENCE: 10

Asp Ile Val Met Thr Gln Ser His Lys Phe Met Ser Thr Ser Val Gly
1               5               10              15

Asp Arg Val Thr Ile Thr Cys Lys Ala Ser Gln Asp Val Thr Thr Ala
            20              25              30

Val Ala Trp Tyr Gln Gln Lys Pro Gly Gln Ser Pro Lys Leu Leu Ile
            35              40              45

Tyr Trp Ala Ser Ser Arg His Thr Gly Val Pro Asp Arg Phe Thr Gly
    50              55              60

Ser Gly Ser Gly Thr Asp Tyr Thr Leu Thr Ile Ser Ser Val Gln Ala
65              70              75              80

Glu Asp Leu Ala Leu Tyr Tyr Cys Gln Gln His Tyr Ser Thr Pro Tyr
            85              90              95

Thr Phe Gly Gly Gly Thr Lys Leu Glu Ile Lys Arg Ala Asp Ala Ala
            100             105             110

Pro Thr Val Ser Ile Phe Pro Pro Ser Ser Glu Gln Leu Thr Ser Gly
            115             120             125

Gly Ala Ser Val Val Cys Phe Leu Asn Asn Phe Tyr Pro Lys Asp Ile
```

-continued

```
              130                 135                 140
Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 11
<211> LENGTH: 7
<212> TYPE: PRT
<213> ORGANISM: Artificial Sequence
<220> FEATURE:
<223> OTHER INFORMATION: CDRH1 for antibody from hybridoma DGH6

<400> SEQUENCE: 11

Gly Tyr Thr Phe Thr Asp Tyr
1               5

<210> SEQ ID NO 12
<211> LENGTH: 6
<212> TYPE: PRT
<213> ORGANISM: Artificial Sequence
<220> FEATURE:
<223> OTHER INFORMATION: CDRH2 for antibody from hybridoma DGH6

<400> SEQUENCE: 12

Asn Thr Glu Thr Gly Glu
1               5

<210> SEQ ID NO 13
<211> LENGTH: 6
<212> TYPE: PRT
<213> ORGANISM: Artificial Sequence
<220> FEATURE:
<223> OTHER INFORMATION: CDRH3 for antibody from hybridoma DGH6

<400> SEQUENCE: 13

Arg Ala Leu Phe Thr Tyr
1               5

<210> SEQ ID NO 14
<211> LENGTH: 17
<212> TYPE: PRT
<213> ORGANISM: Artificial Sequence
<220> FEATURE:
<223> OTHER INFORMATION: CDRL1 for antibody from hybridoma DGH6

<400> SEQUENCE: 14

Lys Ser Ser Gln Ser Leu Leu Asn Ser Gly Asn Gln Lys Asn Tyr Leu
1               5                   10                  15

Ala

<210> SEQ ID NO 15
<211> LENGTH: 7
<212> TYPE: PRT
<213> ORGANISM: Artificial Sequence
<220> FEATURE:
<223> OTHER INFORMATION: CDRL2 for antibody from hybridoma DGH6
```

-continued

```
<400> SEQUENCE: 15

Gly Ala Ser Thr Arg Glu Ser
1               5

<210> SEQ ID NO 16
<211> LENGTH: 9
<212> TYPE: PRT
<213> ORGANISM: Artificial Sequence
<220> FEATURE:
<223> OTHER INFORMATION: CDRL3 for antibody from hybridoma DGH6

<400> SEQUENCE: 16

Gln Asn Asp His Thr Leu Pro Leu Thr
1               5

<210> SEQ ID NO 17
<211> LENGTH: 115
<212> TYPE: PRT
<213> ORGANISM: Artificial Sequence
<220> FEATURE:
<223> OTHER INFORMATION: VH amino acid sequence for antibody from
      hybridoma DGH6

<400> SEQUENCE: 17

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Phe Phe Cys
                85                  90                  95

Thr Arg Arg Ala Leu Phe Thr Tyr Trp Gly Gln Gly Thr Leu Val Thr
            100                 105                 110

Val Ser Ala
        115

<210> SEQ ID NO 18
<211> LENGTH: 438
<212> TYPE: PRT
<213> ORGANISM: Artificial Sequence
<220> FEATURE:
<223> OTHER INFORMATION: heavy chain amino acid sequence for antibody
      from hybridoma DGH6

<400> SEQUENCE: 18

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80
```

-continued

```
Leu Gln Ile Asn Asn Leu Lys Asn Glu Asp Thr Ala Thr Phe Phe Cys
                85                  90                  95

Thr Arg Arg Ala Leu Phe Thr Tyr Trp Gly Gln Gly Thr Leu Val Thr
            100                 105                 110

Val Ser Ala Ala Lys Thr Thr Pro Pro Ser Val Tyr Pro Leu Ala Pro
            115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190

Glu Thr Val Thr Cys Asn Val Ala His Pro Ala Ser Ser Thr Lys Val
            195                 200                 205

Asp Lys Lys Ile Val Pro Arg Asp Cys Gly Cys Lys Pro Cys Ile Cys
    210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
            245                 250                 255

Asp Ile Ser Lys Asp Asp Pro Glu Val Gln Phe Ser Trp Phe Val Asp
            260                 265                 270

Asp Val Glu Val His Thr Ala Gln Thr Gln Pro Arg Glu Glu Gln Phe
            275                 280                 285

Asn Ser Thr Phe Arg Ser Val Ser Glu Leu Pro Ile Met His Gln Asp
    290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
            325                 330                 335

Ala Pro Gln Val Tyr Thr Ile Pro Pro Pro Lys Glu Gln Met Ala Lys
            340                 345                 350

Asp Lys Val Ser Leu Thr Cys Met Ile Thr Asp Phe Phe Pro Glu Asp
            355                 360                 365

Ile Thr Val Glu Trp Gln Trp Asn Gly Gln Pro Ala Glu Asn Tyr Lys
    370                 375                 380

Asn Thr Gln Pro Ile Met Asp Thr Asp Gly Ser Tyr Phe Val Tyr Ser
385                 390                 395                 400

Lys Leu Asn Val Gln Lys Ser Asn Trp Glu Ala Gly Asn Thr Phe Thr
                405                 410                 415

Cys Ser Val Leu His Glu Gly Leu His Asn His His Thr Glu Lys Ser
            420                 425                 430

Leu Ser His Ser Pro Gly
            435
```

```
<210> SEQ ID NO 19
<211> LENGTH: 113
<212> TYPE: PRT
<213> ORGANISM: Artificial Sequence
<220> FEATURE:
<223> OTHER INFORMATION: VL amino acid sequence for antibody from
      hybridoma DGH6

<400> SEQUENCE: 19
```

```
Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Thr Leu Pro Leu Thr Phe Gly Ala Gly Thr Lys Leu Glu Leu
            100                 105                 110

Lys
```

<210> SEQ ID NO 20
<211> LENGTH: 220
<212> TYPE: PRT
<213> ORGANISM: Artificial Sequence
<220> FEATURE:
<223> OTHER INFORMATION: light chain amino acid sequence for antibody
      from hybridoma DGH6

<400> SEQUENCE: 20

```
Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Thr Leu Pro Leu Thr Phe Gly Ala Gly Thr Lys Leu Glu Leu
            100                 105                 110

Lys Arg Ala Asp Ala Ala Pro Thr Val Ser Ile Phe Pro Pro Ser Ser
        115                 120                 125

Glu Gln Leu Thr Ser Gly Gly Ala Ser Val Val Cys Phe Leu Asn Asn
    130                 135                 140

Phe Tyr Pro Lys Asp Ile Asn Val Lys Trp Lys Ile Asp Gly Ser Glu
145                 150                 155                 160

Arg Gln Asn Gly Val Leu Asn Ser Trp Thr Asp Gln Asp Ser Lys Asp
            165                 170                 175

Ser Thr Tyr Ser Met Ser Ser Thr Leu Thr Leu Thr Lys Asp Glu Tyr
            180                 185                 190

Glu Arg His Asn Ser Tyr Thr Cys Glu Ala Thr His Lys Thr Ser Thr
        195                 200                 205

Ser Pro Ile Val Lys Ser Phe Asn Arg Asn Glu Cys
    210                 215                 220
```

<210> SEQ ID NO 21

<211> LENGTH: 9
<212> TYPE: PRT
<213> ORGANISM: Artificial Sequence
<220> FEATURE:
<223> OTHER INFORMATION: CDRH1 for antibody from hybridoma DG4H4

<400> SEQUENCE: 21

Gly Phe Ser Leu Ser Thr Ser Gly Met
1               5

<210> SEQ ID NO 22
<211> LENGTH: 5
<212> TYPE: PRT
<213> ORGANISM: Artificial Sequence
<220> FEATURE:
<223> OTHER INFORMATION: CDRH2 for antibody from hybridoma DG4H4

<400> SEQUENCE: 22

Trp Trp Asp Asp Asp
1               5

<210> SEQ ID NO 23
<211> LENGTH: 13
<212> TYPE: PRT
<213> ORGANISM: Artificial Sequence
<220> FEATURE:
<223> OTHER INFORMATION: CDRH3 for antibody from hybridoma DG4H4

<400> SEQUENCE: 23

Arg Ala Tyr Tyr Tyr Gly Ser Ser Tyr Pro Met Asp Tyr
1               5                   10

<210> SEQ ID NO 24
<211> LENGTH: 15
<212> TYPE: PRT
<213> ORGANISM: Artificial Sequence
<220> FEATURE:
<223> OTHER INFORMATION: CDRL1 for antibody from hybridoma DG4H4

<400> SEQUENCE: 24

Lys Ala Ser Gln Ser Val Asp Tyr Asp Gly Asp Ser Tyr Met Asn
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: CDRL2 for antibody from hybridoma DG4H4

<400> SEQUENCE: 25

Ala Ala Ser Asn Leu Asp Ser
1               5

<210> SEQ ID NO 26
<211> LENGTH: 9
<212> TYPE: PRT
<213> ORGANISM: Artificial Sequence
<220> FEATURE:
<223> OTHER INFORMATION: CDRL3 for antibody from hybridoma DG4H4

<400> SEQUENCE: 26

Gln Gln Ser Asn Glu Asp Pro Leu Thr
1               5

<210> SEQ ID NO 27
<211> LENGTH: 123

```
<212> TYPE: PRT
<213> ORGANISM: Artificial Sequence
<220> FEATURE:
<223> OTHER INFORMATION: VH amino acid sequence for antibody from
      hybridoma DG4H4

<400> SEQUENCE: 27

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Ala Tyr Tyr Tyr Gly Ser Ser Tyr Pro Met Asp Tyr
            100                 105                 110

Trp Gly Gln Gly Thr Ser Val Thr Val Ser Ser
        115                 120

<210> SEQ ID NO 28
<211> LENGTH: 446
<212> TYPE: PRT
<213> ORGANISM: Artificial Sequence
<220> FEATURE:
<223> OTHER INFORMATION: heavy chain amino acid sequence for antibody
      from hybridoma DG4H4

<400> SEQUENCE: 28

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ser
    50                  55                  60

Leu Lys Ser Gln Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Arg Ala Tyr Tyr Tyr Gly Ser Ser Tyr Pro Met Asp Tyr
            100                 105                 110

Trp Gly Gln Gly Thr Ser Val Thr Val Ser Ser Ala Lys Thr Thr Pro
        115                 120                 125

Pro Ser Val Tyr Pro Leu Ala Pro Gly Ser Ala Ala Gln Thr Asn Ser
        130                 135                 140

Met Val Thr Leu Gly Cys Leu Val Lys Gly Tyr Phe Pro Glu Pro Val
145                 150                 155                 160

Thr Val Thr Trp Asn Ser Gly Ser Leu Ser Ser Gly Val His Thr Phe
                165                 170                 175

Pro Ala Val Leu Gln Ser Asp Leu Tyr Thr Leu Ser Ser Ser Val Thr
            180                 185                 190
```

-continued

```
Val Pro Ser Ser Thr Trp Pro Ser Glu Thr Val Thr Cys Asn Val Ala
        195             200             205

His Pro Ala Ser Ser Thr Lys Val Asp Lys Lys Ile Val Pro Arg Asp
        210             215             220

Cys Gly Cys Lys Pro Cys Ile Cys Thr Val Pro Glu Val Ser Ser Val
225             230             235             240

Phe Ile Phe Pro Pro Lys Pro Lys Asp Val Leu Thr Ile Thr Leu Thr
                245             250             255

Pro Lys Val Thr Cys Val Val Val Asp Ile Ser Lys Asp Asp Pro Glu
                260             265             270

Val Gln Phe Ser Trp Phe Val Asp Asp Val Glu Val His Thr Ala Gln
        275             280             285

Thr Gln Pro Arg Glu Glu Gln Phe Asn Ser Thr Phe Arg Ser Val Ser
        290             295             300

Glu Leu Pro Ile Met His Gln Asp Trp Leu Asn Gly Lys Glu Phe Lys
305             310             315             320

Cys Arg Val Asn Ser Ala Ala Phe Pro Ala Pro Ile Glu Lys Thr Ile
                325             330             335

Ser Lys Thr Lys Gly Arg Pro Lys Ala Pro Gln Val Tyr Thr Ile Pro
                340             345             350

Pro Pro Lys Glu Gln Met Ala Lys Asp Lys Val Ser Leu Thr Cys Met
                355             360             365

Ile Thr Asp Phe Phe Pro Glu Asp Ile Thr Val Glu Trp Gln Trp Asn
        370             375             380

Gly Gln Pro Ala Glu Asn Tyr Lys Asn Thr Gln Pro Ile Met Asp Thr
385             390             395             400

Asp Gly Ser Tyr Phe Val Tyr Ser Lys Leu Asn Val Gln Lys Ser Asn
                405             410             415

Trp Glu Ala Gly Asn Thr Phe Thr Cys Ser Val Leu His Glu Gly Leu
                420             425             430

His Asn His His Thr Glu Lys Ser Leu Ser His Ser Pro Gly
        435             440             445

<210> SEQ ID NO 29
<211> LENGTH: 111
<212> TYPE: PRT
<213> ORGANISM: Artificial Sequence
<220> FEATURE:
<223> OTHER INFORMATION: VL amino acid sequence for antibody from
      hybridoma DG4H4

<400> SEQUENCE: 29

Asp Ile Val Leu Thr Gln Ser Pro Thr Ser Leu Ala Val Ser Leu Gly
1               5               10              15

Gln Arg Ala Thr Phe Ser Cys Lys Ala Ser Gln Ser Val Asp Tyr Asp
                20              25              30

Gly Asp Ser Tyr Met Asn Trp Tyr Gln Gln Lys Pro Gly Gln Pro Pro
        35              40              45

Lys Leu Leu Ile Tyr Ala Ala Ser Asn Leu Asp Ser Gly Ile Pro Ala
    50              55              60

Arg Phe Ser Gly Ser Gly Ser Gly Thr Asp Phe Thr Leu Asn Ile His
65              70              75              80

Pro Val Glu Glu Glu Asp Ala Ala Thr Tyr Tyr Cys Gln Gln Ser Asn
                85              90              95

Glu Asp Pro Leu Thr Phe Gly Ala Gly Thr Lys Leu Glu Leu Lys
                100             105             110
```

```
<210> SEQ ID NO 30
<211> LENGTH: 218
<212> TYPE: PRT
<213> ORGANISM: Artificial Sequence
<220> FEATURE:
<223> OTHER INFORMATION: light chain amino acid sequence for antibody
      from hybridoma DG4H4

<400> SEQUENCE: 30

Asp Ile Val Leu Thr Gln Ser Pro Thr Ser Leu Ala Val Ser Leu Gly
1               5                   10                  15

Gln Arg Ala Thr Phe Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Asp Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Leu Thr Phe Gly Ala Gly Thr Lys Leu Glu Leu Lys Arg
            100                 105                 110

Ala Asp Ala Ala Pro Thr Val Ser Ile Phe Pro Pro Ser Ser Glu Gln
            115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
            195                 200                 205

Ile Val Lys Ser Phe Asn Arg Asn Glu Cys
    210                 215

<210> SEQ ID NO 31
<211> LENGTH: 1338
<212> TYPE: DNA
<213> ORGANISM: Artificial Sequence
<220> FEATURE:
<223> OTHER INFORMATION: nucleotide sequence encoding heavy chain of
      antibody from hybridoma DG1A11 reverse translated from SEQ ID NO:
      8 with most likely codons

<400> SEQUENCE: 31
gacgtgcagc tgcaggagag cggccccggc ctggtgaagc ccagccagag cctgagcctg       60
acctgcaccg tgaccgacta cgccatcacc agcgactacg cctggaactg gatcaggcag      120
ttccccggca acaagctgga gtggatgggc tacatcagct acagcggcag caccagctac      180
agcagcagcc tgaagagcag gatcagcatc accagggaca ccagcaagaa ccagttcttc      240
ctgcagctga acagcgtgac ccccgaggac accgccacct actactgcgc cagggccgcc      300
cccttcacca ccctgaccga cttcttcgac tactggggcc agggcaccac cctgaccgtg      360
agcagcgcca agaccacccc cccccagcgtg taccccctgg cccccggcag cgccgcccag      420
```

-continued

```
accaacagca tggtgaccct gggctgcctg gtgaagggct acttccccga gcccgtgacc      480
gtgacctgga acagcggcag cctgagcagc ggcgtgcaca ccttccccgc cgtgctgcag      540
agcgacctgt acaccctgag cagcagcgtg accgtgccca gcagcacctg gcccagcgag      600
accgtgacct gcaacgtggc ccaccccgcc agcagcacca aggtggacaa gaagatcgtg      660
cccagggact gcggctgcaa gccctgcatc tgcaccgtgc ccgaggtgag cagcgtgttc      720
atcttccccc ccaagcccaa ggacgtgctg accatcaccc tgacccccaa ggtgacctgc      780
gtggtggtgg acatcagcaa ggacgacccc gaggtgcagt tcagctggtt cgtggacgac      840
gtggaggtgc acaccgccca gacccagccc agggaggagc agttcaacag caccttcagg      900
agcgtgagcg agctgcccat catgcaccag gactggctga acggcaagga gttcaagtgc      960
agggtgaaca cgccgccctt ccccgccccc atcgagaaga ccatcagcaa gaccaagggc     1020
aggcccaagg cccccccaggt gtacaccatc cccccccccca aggagcagat ggccaaggac     1080
aaggtgagcc tgacctgcat gatcaccgac ttcttccccg aggacatcac cgtggagtgg     1140
cagtggaacg gccagcccgc cgagaactac aagaacaccc agcccatcat ggacaccgac     1200
ggcagctact cgtgtacag caagctgaac gtgcagaaga gcaactggga ggccggcaac     1260
accttcacct gcagcgtgct gcacgagggc ctgcacaacc accacaccga gaagagcctg     1320
agccacagcc ccggcaag                                                  1338
```

```
<210> SEQ ID NO 32
<211> LENGTH: 1338
<212> TYPE: DNA
<213> ORGANISM: Artificial Sequence
<220> FEATURE:
<223> OTHER INFORMATION: nucleotide sequence encoding heavy chain of
      antibody from hybridoma DG1A11 reverse translated from SEQ ID NO:
      8 with consensus codons
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
```

-continued

```
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
```

```
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (261)..(261)
```

-continued

```
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
```

-continued

```
<222> LOCATION: (360)..(360)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
```

-continued

```
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
```

-continued

```
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (588)..(588)
```

```
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
```

```
<222> LOCATION: (699)..(699)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (774)..(774)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
```

```
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (858)..(858)
<223> OTHER INFORMATION: n is a, c, g, or t
<220> FEATURE:
<221> NAME/KEY: misc_feature
<222> LOCATION: (864)..(864)
<223> OTHER INFORMATION: n is a, c, g, or t
<220> FEATURE:
<221> NAME/KEY: misc_feature
<222> LOCATION: (870)..(870)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (891)..(891)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (915)..(915)
<223> OTHER INFORMATION: n is a, c, g, or t
```

-continued

```
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (939)..(939)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (984)..(984)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
<221> NAME/KEY: misc_feature
<222> LOCATION: (990)..(990)
<223> OTHER INFORMATION: n is a, c, g, or t
<220> FEATURE:
<221> NAME/KEY: misc_feature
<222> LOCATION: (1002)..(1002)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1026)..(1026)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1035)..(1035)
<223> OTHER INFORMATION: n is a, c, g, or t
<220> FEATURE:
<221> NAME/KEY: misc_feature
<222> LOCATION: (1041)..(1041)
```

-continued

```
<223> OTHER INFORMATION: n is a, c, g, or t
<220> FEATURE:
<221> NAME/KEY: misc_feature
<222> LOCATION: (1047)..(1047)
<223> OTHER INFORMATION: n is a, c, g, or t
<220> FEATURE:
<221> NAME/KEY: misc_feature
<222> LOCATION: (1053)..(1053)
<223> OTHER INFORMATION: n is a, c, g, or t
<220> FEATURE:
<221> NAME/KEY: misc_feature
<222> LOCATION: (1056)..(1056)
<223> OTHER INFORMATION: n is a, c, g, or t
<220> FEATURE:
<221> NAME/KEY: misc_feature
<222> LOCATION: (1059)..(1059)
<223> OTHER INFORMATION: n is a, c, g, or t
<220> FEATURE:
<221> NAME/KEY: misc_feature
<222> LOCATION: (1074)..(1074)
<223> OTHER INFORMATION: n is a, c, g, or t
<220> FEATURE:
<221> NAME/KEY: misc_feature
<222> LOCATION: (1086)..(1086)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1092)..(1092)
<223> OTHER INFORMATION: n is a, c, g, or t
<220> FEATURE:
<221> NAME/KEY: misc_feature
<222> LOCATION: (1095)..(1095)
<223> OTHER INFORMATION: n is a, c, g, or t
<220> FEATURE:
<221> NAME/KEY: misc_feature
<222> LOCATION: (1107)..(1107)
<223> OTHER INFORMATION: n is a, c, g, or t
<220> FEATURE:
<221> NAME/KEY: misc_feature
<222> LOCATION: (1119)..(1119)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1134)..(1134)
<223> OTHER INFORMATION: n is a, c, g, or t
<220> FEATURE:
<221> NAME/KEY: misc_feature
<222> LOCATION: (1152)..(1152)
<223> OTHER INFORMATION: n is a, c, g, or t
<220> FEATURE:
<221> NAME/KEY: misc_feature
<222> LOCATION: (1158)..(1158)
<223> OTHER INFORMATION: n is a, c, g, or t
<220> FEATURE:
<221> NAME/KEY: misc_feature
<222> LOCATION: (1161)..(1161)
<223> OTHER INFORMATION: n is a, c, g, or t
<220> FEATURE:
<221> NAME/KEY: misc_feature
<222> LOCATION: (1179)..(1179)
<223> OTHER INFORMATION: n is a, c, g, or t
<220> FEATURE:
<221> NAME/KEY: misc_feature
<222> LOCATION: (1185)..(1185)
<223> OTHER INFORMATION: n is a, c, g, or t
<220> FEATURE:
<221> NAME/KEY: misc_feature
<222> LOCATION: (1197)..(1197)
<223> OTHER INFORMATION: n is a, c, g, or t
<220> FEATURE:
<221> NAME/KEY: misc_feature
```

```
<222> LOCATION: (1203)..(1203)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1221)..(1221)
<223> OTHER INFORMATION: n is a, c, g, or t
<220> FEATURE:
<221> NAME/KEY: misc_feature
<222> LOCATION: (1227)..(1227)
<223> OTHER INFORMATION: n is a, c, g, or t
<220> FEATURE:
<221> NAME/KEY: misc_feature
<222> LOCATION: (1233)..(1233)
<223> OTHER INFORMATION: n is a, c, g, or t
<220> FEATURE:
<221> NAME/KEY: misc_feature
<222> LOCATION: (1242)..(1242)
<223> OTHER INFORMATION: n is a, c, g, or t
<220> FEATURE:
<221> NAME/KEY: misc_feature
<222> LOCATION: (1254)..(1254)
<223> OTHER INFORMATION: n is a, c, g, or t
<220> FEATURE:
<221> NAME/KEY: misc_feature
<222> LOCATION: (1257)..(1257)
<223> OTHER INFORMATION: n is a, c, g, or t
<220> FEATURE:
<221> NAME/KEY: misc_feature
<222> LOCATION: (1263)..(1263)
<223> OTHER INFORMATION: n is a, c, g, or t
<220> FEATURE:
<221> NAME/KEY: misc_feature
<222> LOCATION: (1269)..(1269)
<223> OTHER INFORMATION: n is a, c, g, or t
<220> FEATURE:
<221> NAME/KEY: misc_feature
<222> LOCATION: (1275)..(1275)
<223> OTHER INFORMATION: n is a, c, g, or t
<220> FEATURE:
<221> NAME/KEY: misc_feature
<222> LOCATION: (1278)..(1278)
<223> OTHER INFORMATION: n is a, c, g, or t
<220> FEATURE:
<221> NAME/KEY: misc_feature
<222> LOCATION: (1281)..(1281)
<223> OTHER INFORMATION: n is a, c, g, or t
<220> FEATURE:
<221> NAME/KEY: misc_feature
<222> LOCATION: (1290)..(1290)
<223> OTHER INFORMATION: n is a, c, g, or t
<220> FEATURE:
<221> NAME/KEY: misc_feature
<222> LOCATION: (1293)..(1293)
<223> OTHER INFORMATION: n is a, c, g, or t
<220> FEATURE:
<221> NAME/KEY: misc_feature
<222> LOCATION: (1308)..(1308)
<223> OTHER INFORMATION: n is a, c, g, or t
<220> FEATURE:
<221> NAME/KEY: misc_feature
<222> LOCATION: (1317)..(1317)
<223> OTHER INFORMATION: n is a, c, g, or t
<220> FEATURE:
<221> NAME/KEY: misc_feature
<222> LOCATION: (1320)..(1320)
<223> OTHER INFORMATION: n is a, c, g, or t
<220> FEATURE:
<221> NAME/KEY: misc_feature
<222> LOCATION: (1323)..(1323)
<223> OTHER INFORMATION: n is a, c, g, or t
<220> FEATURE:
```

```
<221> NAME/KEY: misc_feature
<222> LOCATION: (1329)..(1329)
<223> OTHER INFORMATION: n is a, c, g, or t
<220> FEATURE:
<221> NAME/KEY: misc_feature
<222> LOCATION: (1332)..(1332)
<223> OTHER INFORMATION: n is a, c, g, or t
<220> FEATURE:
<221> NAME/KEY: misc_feature
<222> LOCATION: (1335)..(1335)
<223> OTHER INFORMATION: n is a, c, g, or t

<400> SEQUENCE: 32
gaygtncary tncargarws nggnccnggn ytngtnaarc cnwsncarws nytnwsnytn      60
acntgyacng tnacngayta ygcnathacn wsngaytayg cntggaaytg gathmgncar     120
ttyccnggna ayaarytnga rtggatgggn tayathwsnt aywsnggnws nacnwsntay     180
wsnwsnwsny tnaarwsnmg nathwsnath acnmgngaya cnwsnaaraa ycarttytty     240
ytncarytna aywsngtnac nccngargay acngcnacnt aytaytgygc nmgngcngcn     300
ccnttyacna cnytnacnga yttyttygay taytgggggnc arggnacnac nytnacngtn    360
wsnwsngcna aracnacncc nccnwsngtn tayccnytng cnccnggnws ngcngcncar     420
acnaaywsna tggtnacnyt nggntgyytn gtnaarggnt ayttyccnga rccngtnacn     480
gtnacntgga aywsnggnws nytnwsnwsn ggngtncaya cnttyccngc ngtnytncar     540
wsngayytnt ayacnytnws nwsnwsngtn acngtnccnw snwsnacntg gccnwsngar     600
acngtnacnt gyaaygtngc ncayccngcn wsnwsnacna argtngayaa raarathgtn     660
ccnmgngayt gyggntgyaa rccntgyath tgyacngtnc cngargtnws nwsngtntty    720
athttyccnc cnaarccnaa rgaygtnytn acnathacny tnacnccnaa rgtnacntgy     780
gtngtngtng ayathwsnaa rgaygaycn gargtncart tywsntggtt ygtngaygay     840
gtngargtnc ayacngcnca racncarcn mgngargarc arttyaayws nacnttymgn      900
wsngtnwsng arytnccnat hatgcaycar gaytggytna ayggnaarga rttyaartgy     960
mgngtnaayw sngcngcntt yccngcnccn athgaraara cnathwsnaa racnaarggn    1020
mgnccnaarg cnccncargt ntayacnath ccnccnccna argarcarat ggcnaargay    1080
aargtnwsny tnacntgyat gathacngay ttyttyccng argayathac ngtngartgg    1140
cartggaayg gncarccngc ngaraaytay aaraayacnc arccnathat ggayacngay    1200
ggnwsntayt tygtntaytws naarytnaay gtncaraarw snaaytggga rgcnggnaay    1260
acnttyacnt gywsngtnyt ncaygarggn ytncayaayc aycayacnga raarwsnytn    1320
wsncaywsnc cnggnaar                                                   1338

<210> SEQ ID NO 33
<211> LENGTH: 642
<212> TYPE: DNA
<213> ORGANISM: Artificial Sequence
<220> FEATURE:
<223> OTHER INFORMATION: nucleotide sequence encoding light chain of
      antibody from hybridoma DG1A11 reverse translated from SEQ ID NO:
      10 with most likely codons

<400> SEQUENCE: 33
gacatcgtga tgacccagag ccacaagttc atgagcacca gcgtgggcga cagggtgacc      60
atcacctgca aggccagcca ggacgtgacc accgccgtgg cctggtacca gcagaagccc     120
ggccagagcc ccaagctgct gatctactgg gccagcagca ggcacaccgg cgtgcccgac     180
aggttcaccg gcagcggcag cggcaccgac tacaccctga ccatcagcag cgtgcaggcc     240
```

```
gaggacctgg ccctgtacta ctgccagcag cactacagca cccccctacac cttcggcggc      300 ggcaccaagc tggagatcaa gagggccgac gccgcccccca ccgtgagcat cttccccccc      360
agcagcgagc agctgaccag cggcggcgcc agcgtggtgt gcttcctgaa caacttctac      420
cccaaggaca tcaacgtgaa gtggaagatc gacggcagcg agaggcagaa cggcgtgctg      480
aacagctgga ccgaccagga cagcaaggac agcacctaca gcatgagcag caccctgacc      540
ctgaccaagg acgagtacga gaggcacaac agctacacct gcgaggccac ccacaagacc      600
agcaccagcc ccatcgtgaa gagcttcaac aggaacgagt gc                          642
```

```
<210> SEQ ID NO 34
<211> LENGTH: 642
<212> TYPE: DNA
<213> ORGANISM: Artificial Sequence
<220> FEATURE:
<223> OTHER INFORMATION: nucleotide sequence encoding light chain of
      antibody from hybridoma DG1A11 reverse translated from SEQ ID NO:
      10 with consensus codons
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
```

-continued

```
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
```

-continued

```
<222> LOCATION: (177)..(177)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
```

-continued

```
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
```

-continued

```
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (492)..(492)
```

-continued

```
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
```

```
<222> LOCATION: (609)..(609)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t

<400> SEQUENCE: 34
gayathgtna tgacncarws ncayaartty atgwsnacnw sngtnggnga ymgngtnacn        60
athacntgya argcnwsnca rgaygtnacn acngcngtng cntggtayca rcaraarccn       120
ggncarwsnc cnaarytnyt nathtaytgg gcnwsnwsnm gncayacngg ngtnccngay       180
mgnttyacng gnwsnggnws nggnacngay tayacnytna cnathwsnws ngtncargcn       240
gargayytng cnytntayta ytgycarcar caytaywsna cnccntayac nttyggnggn       300
ggnacnaary tngarathaa rmgngcngay gcngcnccna cngtnwsnat httyccnccn       360
wsnwsngarc arytnacnws nggnggngcn wsngtngtnt gyttyytnaa yaayttytay       420
ccnaargaya thaaygtnaa rtggaarath gayggnwsng armgncaraa yggngtnytn       480
aaywsntgga cngaycarga ywsnaargay wsnacntayw snatgwsnws nacnytnacn       540
ytnacnaarg aygartayga rmgncayaay wsntayacnt gygargcnac ncayaaracn       600
wsnacnwsnc cnathgtnaa rwsnttyaay mgnaaygart gy                         642

<210> SEQ ID NO 35
<211> LENGTH: 1314
<212> TYPE: DNA
<213> ORGANISM: Artificial Sequence
<220> FEATURE:
<223> OTHER INFORMATION: nucleotide sequence encoding heavy chain of
      antibody from hybridoma DGH6 reverse translated from SEQ ID NO: 18
      with most likely codons

<400> SEQUENCE: 35
cagatccagc tggtgcagag cggccccgag ctgaagaagc ccggcgagac cgtgaagatc        60
agctgcaagg ccagcggcta caccttcacc gactacagca tgcactgggt gaagcaggcc       120
cccggcaagg gcctgaagtg gatgggctgg atcaacaccg agaccggcga gcccacctac       180
gccgacgact tcaagggcag gttcgccttc agcctggaga ccagcgccag caccgcctac       240
ctgcagatca caacctgaa gaacgaggac accgccacct tcttctgcac caggagggcc       300
ctgttcacct actggggcca gggcaccctg gtgaccgtga gcgccgccaa gaccacccc       360 cccagcgtgt accccctggc ccccggcagc gccgcccaga ccaacagcat ggtgaccctg       420
ggctgcctgg tgaagggcta cttccccgag cccgtgaccg tgacctggaa cagcggcagc       480
ctgagcagcg gcgtgcacac cttccccgcc gtgctgcaga gcgacctgta caccctgagc       540
agcagcgtga ccgtgcccag cagcacctgg cccagcgaga ccgtgacctg caacgtggcc       600
caccccgcca gcagcaccaa ggtggacaag aagatcgtgc ccagggactg cggctgcaag       660
ccctgcatct gcaccgtgcc cgaggtgagc agcgtgttca tcttcccccc caagcccaag       720
```

-continued

```
gacgtgctga ccatcaccct gacccccaag gtgacctgcg tggtggtgga catcagcaag      780
gacgaccccg aggtgcagtt cagctggttc gtggacgacg tggaggtgca caccgcccag      840
acccagccca gggaggagca gttcaacagc accttcagga gcgtgagcga gctgcccatc      900
atgcaccagg actggctgaa cggcaaggag ttcaagtgca gggtgaacag cgccgccttc      960
cccgccccca tcgagaagac catcagcaag accaagggca ggcccaaggc cccccaggtg     1020
tacaccatcc cccccccaa ggagcagatg gccaaggaca aggtgagcct gacctgcatg     1080
atcaccgact tcttccccga ggacatcacc gtggagtggc agtggaacgg ccagcccgcc     1140
gagaactaca agaacaccca gcccatcatg gacaccgacg gcagctactt cgtgtacagc     1200
aagctgaacg tgcagaagag caactgggag gccggcaaca ccttcacctg cagcgtgctg     1260
cacgagggcc tgcacaacca ccacaccgag aagagcctga gccacagccc cggc          1314
```

```
<210> SEQ ID NO 36
<211> LENGTH: 1314
<212> TYPE: DNA
<213> ORGANISM: Artificial Sequence
<220> FEATURE:
<223> OTHER INFORMATION: nucleotide sequence encoding heavy chain of
      antibody from hybridoma DGH6 reverse translated from SEQ ID NO: 18
      with consensus codons
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
```

```
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
```

-continued

```
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
```

-continued

```
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
```

-continued

```
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
```

```
<222> LOCATION: (474)..(474)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
```

-continued

```
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
```

-continued

```
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (690)..(690)
<223> OTHER INFORMATION: n is a, c, g, or t
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (708)..(708)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (726)..(726)
<223> OTHER INFORMATION: n is a, c, g, or t
<220> FEATURE:
<221> NAME/KEY: misc_feature
<222> LOCATION: (729)..(729)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (741)..(741)
```

```
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (747)..(747)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (795)..(795)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (834)..(834)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (849)..(849)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
```

```
<222> LOCATION: (870)..(870)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (879)..(879)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (885)..(885)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t
<220> FEATURE:
<221> NAME/KEY: misc_feature
<222> LOCATION: (942)..(942)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (951)..(951)
<223> OTHER INFORMATION: n is a, c, g, or t
<220> FEATURE:
<221> NAME/KEY: misc_feature
<222> LOCATION: (954)..(954)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (981)..(981)
<223> OTHER INFORMATION: n is a, c, g, or t
<220> FEATURE:
<221> NAME/KEY: misc_feature
<222> LOCATION: (987)..(987)
<223> OTHER INFORMATION: n is a, c, g, or t
<220> FEATURE:
```

-continued

```
<221> NAME/KEY: misc_feature
<222> LOCATION: (993)..(993)
<223> OTHER INFORMATION: n is a, c, g, or t
<220> FEATURE:
<221> NAME/KEY: misc_feature
<222> LOCATION: (999)..(999)
<223> OTHER INFORMATION: n is a, c, g, or t
<220> FEATURE:
<221> NAME/KEY: misc_feature
<222> LOCATION: (1002)..(1002)
<223> OTHER INFORMATION: n is a, c, g, or t
<220> FEATURE:
<221> NAME/KEY: misc_feature
<222> LOCATION: (1005)..(1005)
<223> OTHER INFORMATION: n is a, c, g, or t
<220> FEATURE:
<221> NAME/KEY: misc_feature
<222> LOCATION: (1011)..(1011)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1020)..(1020)
<223> OTHER INFORMATION: n is a, c, g, or t
<220> FEATURE:
<221> NAME/KEY: misc_feature
<222> LOCATION: (1026)..(1026)
<223> OTHER INFORMATION: n is a, c, g, or t
<220> FEATURE:
<221> NAME/KEY: misc_feature
<222> LOCATION: (1032)..(1032)
<223> OTHER INFORMATION: n is a, c, g, or t
<220> FEATURE:
<221> NAME/KEY: misc_feature
<222> LOCATION: (1035)..(1035)
<223> OTHER INFORMATION: n is a, c, g, or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1053)..(1053)
<223> OTHER INFORMATION: n is a, c, g, or t
<220> FEATURE:
<221> NAME/KEY: misc_feature
<222> LOCATION: (1065)..(1065)
<223> OTHER INFORMATION: n is a, c, g, or t
<220> FEATURE:
<221> NAME/KEY: misc_feature
<222> LOCATION: (1068)..(1068)
<223> OTHER INFORMATION: n is a, c, g, or t
<220> FEATURE:
<221> NAME/KEY: misc_feature
<222> LOCATION: (1071)..(1071)
<223> OTHER INFORMATION: n is a, c, g, or t
<220> FEATURE:
<221> NAME/KEY: misc_feature
<222> LOCATION: (1074)..(1074)
<223> OTHER INFORMATION: n is a, c, g, or t
<220> FEATURE:
<221> NAME/KEY: misc_feature
<222> LOCATION: (1086)..(1086)
<223> OTHER INFORMATION: n is a, c, g, or t
<220> FEATURE:
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
```

-continued

```
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1137)..(1137)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1158)..(1158)
<223> OTHER INFORMATION: n is a, c, g, or t
<220> FEATURE:
<221> NAME/KEY: misc_feature
<222> LOCATION: (1164)..(1164)
<223> OTHER INFORMATION: n is a, c, g, or t
<220> FEATURE:
<221> NAME/KEY: misc_feature
<222> LOCATION: (1176)..(1176)
<223> OTHER INFORMATION: n is a, c, g, or t
<220> FEATURE:
<221> NAME/KEY: misc_feature
<222> LOCATION: (1182)..(1182)
<223> OTHER INFORMATION: n is a, c, g, or t
<220> FEATURE:
<221> NAME/KEY: misc_feature
<222> LOCATION: (1185)..(1185)
<223> OTHER INFORMATION: n is a, c, g, or t
<220> FEATURE:
<221> NAME/KEY: misc_feature
<222> LOCATION: (1194)..(1194)
<223> OTHER INFORMATION: n is a, c, g, or t
<220> FEATURE:
<221> NAME/KEY: misc_feature
<222> LOCATION: (1200)..(1200)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1212)..(1212)
<223> OTHER INFORMATION: n is a, c, g, or t
<220> FEATURE:
<221> NAME/KEY: misc_feature
<222> LOCATION: (1221)..(1221)
<223> OTHER INFORMATION: n is a, c, g, or t
<220> FEATURE:
<221> NAME/KEY: misc_feature
<222> LOCATION: (1233)..(1233)
<223> OTHER INFORMATION: n is a, c, g, or t
<220> FEATURE:
<221> NAME/KEY: misc_feature
<222> LOCATION: (1236)..(1236)
<223> OTHER INFORMATION: n is a, c, g, or t
<220> FEATURE:
<221> NAME/KEY: misc_feature
<222> LOCATION: (1242)..(1242)
<223> OTHER INFORMATION: n is a, c, g, or t
<220> FEATURE:
<221> NAME/KEY: misc_feature
<222> LOCATION: (1248)..(1248)
<223> OTHER INFORMATION: n is a, c, g, or t
<220> FEATURE:
<221> NAME/KEY: misc_feature
<222> LOCATION: (1254)..(1254)
<223> OTHER INFORMATION: n is a, c, g, or t
<220> FEATURE:
<221> NAME/KEY: misc_feature
<222> LOCATION: (1257)..(1257)
<223> OTHER INFORMATION: n is a, c, g, or t
<220> FEATURE:
<221> NAME/KEY: misc_feature
<222> LOCATION: (1260)..(1260)
```

```
<223> OTHER INFORMATION: n is a, c, g, or t
<220> FEATURE:
<221> NAME/KEY: misc_feature
<222> LOCATION: (1269)..(1269)
<223> OTHER INFORMATION: n is a, c, g, or t
<220> FEATURE:
<221> NAME/KEY: misc_feature
<222> LOCATION: (1272)..(1272)
<223> OTHER INFORMATION: n is a, c, g, or t
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: misc_feature
<222> LOCATION: (1296)..(1296)
<223> OTHER INFORMATION: n is a, c, g, or t
<220> FEATURE:
<221> NAME/KEY: misc_feature
<222> LOCATION: (1299)..(1299)
<223> OTHER INFORMATION: n is a, c, g, or t
<220> FEATURE:
<221> NAME/KEY: misc_feature
<222> LOCATION: (1302)..(1302)
<223> OTHER INFORMATION: n is a, c, g, or t
<220> FEATURE:
<221> NAME/KEY: misc_feature
<222> LOCATION: (1308)..(1308)
<223> OTHER INFORMATION: n is a, c, g, or t
<220> FEATURE:
<221> NAME/KEY: misc_feature
<222> LOCATION: (1311)..(1311)
<223> OTHER INFORMATION: n is a, c, g, or t
<220> FEATURE:
<221> NAME/KEY: misc_feature
<222> LOCATION: (1314)..(1314)
<223> OTHER INFORMATION: n is a, c, g, or t

<400> SEQUENCE: 36
carathcary tngtncarws nggnccngar ytnaaraarc cnggngarac ngtnaarath      60
wsntgyaarg cnwsnggnta yacnttyacn gaytaywsna tgcaytgggt naarcargcn     120
ccnggnaarg gnytnaartg datgggntgg athaayacng aracnggnga rccnacntay     180
gcngaygayt tyaarggnmg nttygcntty wsnytngara cnwsngcnws nacngcntay     240
ytncaratha ayaayytnaa raaygargay acngcnacnt tyttytgyac nmgnmgngcn     300
ytnttyacnt aytggggnca rggnacnytn gtnacngtnw sngcngcnaa racnacnccn     360
ccnwsngtnt ayccnytngc nccnggnwsn gcngcncara cnaaywsnat ggtnacnytn     420
ggntgyytng tnaarggnta yttyccngar ccngtnacng tnacntggaa ywsnggnwsn     480
ytnwsnwsng gngtncayac nttyccngcn gtnytncarw sngayytnta yacnytnwsn     540
wsnwsngtna cngtnccnws nwsnacntgg ccnwsngara cngtnacntg yaaygtngcn     600
cayccngcnw snwsnacnaa rgtngayaar aarathgtnc cnmgngaytg yggntgyaar     660
ccntgyatht gyacngtncc ngargtnwsn wsngtnttya thttyccncc naarccnaar     720
gaygtnytna cnathacnyt nacnccnaar gtnacntgyg tngtngtnga yathwsnaar     780
gaygayccng argtncartt ywsntggtty gtngaygayg tngargtnca yacngcncar     840
acncarccnm gngargarca rttyaaywsn acnttymgnw sngtnwsnga rytnccnath     900
atgcaycarg aytggytnaa yggnaargar ttyaartgym gngtnaayws ngcngcntty     960
ccngcnccna thgaraaarac nathwsnaar acnaarggnm gnccnaargc nccncargtn    1020
tayacnathc cncncccnaa rgarcaratg gcnaargaya argtnwsnyt nacntgyatg    1080
athacngayt tyttyccnga rgayathacn gtngartggc artggaaygg ncarccngcn    1140
garaaytaya araaytacnca rccnathatg gayacngayg gnwsntaytt ygtntaywsn    1200
```

```
aarytnaayg tncaraarws naaytgggar gcnggnaaya cnttyacntg ywsngtnytn      1260
caygarggny tncayaayca ycayacngar aarwsnytnw sncaywsncc nggn            1314
```

<210> SEQ ID NO 37
<211> LENGTH: 660
<212> TYPE: DNA
<213> ORGANISM: Artificial Sequence
<220> FEATURE:
<223> OTHER INFORMATION: nucleotide sequence encoding light chain of
      antibody from hybridoma DGH6 reverse translated from SEQ ID NO: 20
      with most likely codons

<400> SEQUENCE: 37

```
gacatcgtga tgacccagag ccccagcagc ctgagcgtga gcgccggcga gaaggtgacc        60
atgagctgca agagcagcca gagcctgctg aacagcggca accagaagaa ctacctggcc       120
tggtaccagc agaagcccgg ccagcccccc aagctgctga tctacggcgc cagcaccagg       180
gagagcggcg tgcccgacag gttcaccggc agcggcagcg gcaccgactt caccctgacc       240
atcagcagcg tgcaggccga ggacctggcc gtgtactact gccagaacga ccacaccctg       300
cccctgacct tcggcgccgg caccaagctg gagctgaaga gggccgacgc cgcccccacc       360
gtgagcatct ccccccccag cagcgagcag ctgaccagcg gcggcgccag cgtggtgtgc       420
ttcctgaaca acttctaccc caaggacatc aacgtgaagt ggaagatcga cggcagcgag       480
aggcagaacg gcgtgctgaa cagctggacc gaccaggaca gcaaggacag cacctacagc       540
atgagcagca ccctgaccct gaccaaggac gagtacgaga ggcacaacag ctacacctgc       600
gaggccaccc acaagaccag caccagcccc atcgtgaaga gcttcaacag gaacgagtgc       660
```

<210> SEQ ID NO 38
<211> LENGTH: 660
<212> TYPE: DNA
<213> ORGANISM: Artificial Sequence
<220> FEATURE:
<223> OTHER INFORMATION: nucleotide sequence encoding light chain of
      antibody from hybridoma DGH6 reverse translated from SEQ ID NO: 20
      with consensus codons
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)

```
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
```

```
<222> LOCATION: (150)..(150)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
```

```
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
```

-continued

```
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (411)..(411)
```

-continued

```
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
```

-continued

```
<222> LOCATION: (552)..(552)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t

<400> SEQUENCE: 38
gayathgtna tgacncarws nccnwsnwsn ytnwsngtnw sngcnggnga raargtnacn      60
atgwsntgya arwsnwsnca rwsnytnytn aaywsnggna aycaraaraa ytayytngcn     120
tggtaycarc araarccngg ncarccnccn aarytnytna thtayggngc nwsnacnmgn     180
```

```
garwsnggng tnccngaymg nttyacnggn wsnggnwsng gnacngaytt yacnytnacn      240
athwsnwsng tncargcnga rgayytngcn gtntaytayt gycaraayga ycayacnytn      300
ccnytnacnt tyggngcngg nacnaarytn garytnaarm gngcngaygc ngcnccnacn      360
gtnwsnatht tyccnccnws nwsngarcar ytnacnwsng gnggngcnws ngtngtntgy      420
ttyytnaaya ayttytaycc naargayath aaygtnaart ggaarathga yggnwsngar      480
mgncaraayg gngtnytnaa ywsntggacn gaycargayw snaargayws nacntaywsn      540
atgwsnwsna cnytnacnyt nacnaargay gartaygarm gncayaayws ntayacntgy      600
gargcnacnc ayaaracnws nacnwsnccn athgtnaarw snttyaaymg naaygartgy      660
```

```
<210> SEQ ID NO 39
<211> LENGTH: 1338
<212> TYPE: DNA
<213> ORGANISM: Artificial Sequence
<220> FEATURE:
<223> OTHER INFORMATION: nucleotide sequence encoding heavy chain of
      antibody from hybridoma DG4H4 reverse translated from SEQ ID NO:
      28 with most likely codons

<400> SEQUENCE: 39
```

```
caggtgaccc tgaaggagag cggccccggc atcctgaagc ccagccagac cctgagcctg       60
acctgcagct tcagcggctt cagcctgagc accagcggca tgggcgtggg ctggatcagg      120
cagcccagcg gcaagggcct ggagtggctg gcccacatct ggtgggacga cgacaagtac      180
tacaacccca gcctgaagag ccagctgacc atcagcaagg acaccagcag gaaccaggtg      240
ttcctgaaga tcaccagcgt ggacaccgcc gacaccgcca cctactactg cgccaggagg      300
gcctactact acggcagcag ctaccccatg gactactggg gccagggcac cagcgtgacc      360
gtgagcagcg ccaagaccac ccccccagc gtgtaccccc tggccccggg cagcgccgcc      420
cagaccaaca gcatggtgac cctgggctgc ctggtgaagg gctacttccc cgagcccgtg      480
accgtgacct ggaacagcgg cagcctgagc agcggcgtgc acaccttccc cgccgtgctg      540
cagagcgacc tgtacaccct gagcagcagc gtgaccgtgc ccagcagcac ctggcccagc      600
gagaccgtga cctgcaacgt ggcccacccc gccagcagca ccaaggtgga caagaagatc      660
gtgcccaggg actgcggctg caagccctgc atctgcaccg tgcccgaggt gagcagcgtg      720
ttcatcttcc ccccaagcc caaggacgtg ctgaccatca ccctgacccc caaggtgacc      780
tgcgtggtgg tggacatcag caaggacgac cccgaggtgc agttcagctg gttcgtggac      840
gacgtggagg tgcacaccgc ccagacccag cccagggagg agcagttcaa cagcaccttc      900
aggagcgtga gcgagctgcc catcatgcac caggactggc tgaacggcaa ggagttcaag      960
tgcagggtga acagcgccgc cttccccgcc cccatcgaga gaccatcag caagaccaag     1020 ggcaggccca aggccccca ggtgtacacc atcccccccc ccaaggagca gatggccaag     1080
gacaaggtga gcctgacctg catgatcacc gacttcttcc ccgaggacat caccgtggag     1140
tggcagtgga cggccagcc cgccgagaac tacaagaaca cccagcccat catggacacc     1200
gacggcagct acttcgtgta cagcaagctg aacgtgcaga gagcaactg ggaggccggc     1260 aacaccttca cctgcagcgt gctgcacgag ggcctgcaca ccaccacac cgagaagagc     1320 ctgagccaca gccccggc                                                1338
```

```
<210> SEQ ID NO 40
<211> LENGTH: 1338
<212> TYPE: DNA
<213> ORGANISM: Artificial Sequence
```

```
<220> FEATURE:
<223> OTHER INFORMATION: nucleotide sequence encoding heavy chain of
      antibody from hybridoma DG4H4 reverse translated from SEQ ID NO:
      28 with consensus codons
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (84)..(84)
```

-continued

```
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (93)..(93)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t
<220> FEATURE:
<221> NAME/KEY: misc_feature
<222> LOCATION: (111)..(111)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
```

-continued

```
<222> LOCATION: (201)..(201)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
```

-continued

```
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
```

-continued

```
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (453)..(453)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (477)..(477)
```

-continued

```
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
```

```
<222> LOCATION: (558)..(558)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (567)..(567)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (588)..(588)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
```

-continued

```
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (639)..(639)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t
<220> FEATURE:
<221> NAME/KEY: misc_feature
<222> LOCATION: (678)..(678)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (705)..(705)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (717)..(717)
<223> OTHER INFORMATION: n is a, c, g, or t
<220> FEATURE:
<221> NAME/KEY: misc_feature
<222> LOCATION: (720)..(720)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (735)..(735)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
```

-continued

```
<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (753)..(753)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (762)..(762)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (777)..(777)
<223> OTHER INFORMATION: n is a, c, g, or t
<220> FEATURE:
<221> NAME/KEY: misc_feature
<222> LOCATION: (780)..(780)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (846)..(846)
<223> OTHER INFORMATION: n is a, c, g, or t
<220> FEATURE:
<221> NAME/KEY: misc_feature
<222> LOCATION: (852)..(852)
<223> OTHER INFORMATION: n is a, c, g, or t
<220> FEATURE:
<221> NAME/KEY: misc_feature
<222> LOCATION: (858)..(858)
```

-continued

```
<223> OTHER INFORMATION: n is a, c, g, or t
<220> FEATURE:
<221> NAME/KEY: misc_feature
<222> LOCATION: (861)..(861)
<223> OTHER INFORMATION: n is a, c, g, or t
<220> FEATURE:
<221> NAME/KEY: misc_feature
<222> LOCATION: (867)..(867)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (894)..(894)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t
<220> FEATURE:
<221> NAME/KEY: misc_feature
<222> LOCATION: (903)..(903)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (912)..(912)
<223> OTHER INFORMATION: n is a, c, g, or t
<220> FEATURE:
<221> NAME/KEY: misc_feature
<222> LOCATION: (918)..(918)
<223> OTHER INFORMATION: n is a, c, g, or t
<220> FEATURE:
<221> NAME/KEY: misc_feature
<222> LOCATION: (921)..(921)
<223> OTHER INFORMATION: n is a, c, g, or t
<220> FEATURE:
<221> NAME/KEY: misc_feature
<222> LOCATION: (942)..(942)
<223> OTHER INFORMATION: n is a, c, g, or t
<220> FEATURE:
<221> NAME/KEY: misc_feature
<222> LOCATION: (948)..(948)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (975)..(975)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t
<220> FEATURE:
<221> NAME/KEY: misc_feature
<222> LOCATION: (981)..(981)
<223> OTHER INFORMATION: n is a, c, g, or t
<220> FEATURE:
<221> NAME/KEY: misc_feature
```

-continued

```
<222> LOCATION: (987)..(987)
<223> OTHER INFORMATION: n is a, c, g, or t
<220> FEATURE:
<221> NAME/KEY: misc_feature
<222> LOCATION: (990)..(990)
<223> OTHER INFORMATION: n is a, c, g, or t
<220> FEATURE:
<221> NAME/KEY: misc_feature
<222> LOCATION: (993)..(993)
<223> OTHER INFORMATION: n is a, c, g, or t
<220> FEATURE:
<221> NAME/KEY: misc_feature
<222> LOCATION: (1005)..(1005)
<223> OTHER INFORMATION: n is a, c, g, or t
<220> FEATURE:
<221> NAME/KEY: misc_feature
<222> LOCATION: (1011)..(1011)
<223> OTHER INFORMATION: n is a, c, g, or t
<220> FEATURE:
<221> NAME/KEY: misc_feature
<222> LOCATION: (1017)..(1017)
<223> OTHER INFORMATION: n is a, c, g, or t
<220> FEATURE:
<221> NAME/KEY: misc_feature
<222> LOCATION: (1023)..(1023)
<223> OTHER INFORMATION: n is a, c, g, or t
<220> FEATURE:
<221> NAME/KEY: misc_feature
<222> LOCATION: (1026)..(1026)
<223> OTHER INFORMATION: n is a, c, g, or t
<220> FEATURE:
<221> NAME/KEY: misc_feature
<222> LOCATION: (1029)..(1029)
<223> OTHER INFORMATION: n is a, c, g, or t
<220> FEATURE:
<221> NAME/KEY: misc_feature
<222> LOCATION: (1035)..(1035)
<223> OTHER INFORMATION: n is a, c, g, or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1044)..(1044)
<223> OTHER INFORMATION: n is a, c, g, or t
<220> FEATURE:
<221> NAME/KEY: misc_feature
<222> LOCATION: (1050)..(1050)
<223> OTHER INFORMATION: n is a, c, g, or t
<220> FEATURE:
<221> NAME/KEY: misc_feature
<222> LOCATION: (1056)..(1056)
<223> OTHER INFORMATION: n is a, c, g, or t
<220> FEATURE:
<221> NAME/KEY: misc_feature
<222> LOCATION: (1059)..(1059)
<223> OTHER INFORMATION: n is a, c, g, or t
<220> FEATURE:
<221> NAME/KEY: misc_feature
<222> LOCATION: (1062)..(1062)
<223> OTHER INFORMATION: n is a, c, g, or t
<220> FEATURE:
<221> NAME/KEY: misc_feature
<222> LOCATION: (1077)..(1077)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1092)..(1092)
<223> OTHER INFORMATION: n is a, c, g, or t
<220> FEATURE:
<221> NAME/KEY: misc_feature
<222> LOCATION: (1095)..(1095)
<223> OTHER INFORMATION: n is a, c, g, or t
<220> FEATURE:
```

-continued

```
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1122)..(1122)
<223> OTHER INFORMATION: n is a, c, g, or t
<220> FEATURE:
<221> NAME/KEY: misc_feature
<222> LOCATION: (1134)..(1134)
<223> OTHER INFORMATION: n is a, c, g, or t
<220> FEATURE:
<221> NAME/KEY: misc_feature
<222> LOCATION: (1137)..(1137)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1161)..(1161)
<223> OTHER INFORMATION: n is a, c, g, or t
<220> FEATURE:
<221> NAME/KEY: misc_feature
<222> LOCATION: (1164)..(1164)
<223> OTHER INFORMATION: n is a, c, g, or t
<220> FEATURE:
<221> NAME/KEY: misc_feature
<222> LOCATION: (1182)..(1182)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1200)..(1200)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1209)..(1209)
<223> OTHER INFORMATION: n is a, c, g, or t
<220> FEATURE:
<221> NAME/KEY: misc_feature
<222> LOCATION: (1218)..(1218)
<223> OTHER INFORMATION: n is a, c, g, or t
<220> FEATURE:
<221> NAME/KEY: misc_feature
<222> LOCATION: (1224)..(1224)
<223> OTHER INFORMATION: n is a, c, g, or t
<220> FEATURE:
<221> NAME/KEY: misc_feature
<222> LOCATION: (1230)..(1230)
<223> OTHER INFORMATION: n is a, c, g, or t
<220> FEATURE:
<221> NAME/KEY: misc_feature
<222> LOCATION: (1236)..(1236)
<223> OTHER INFORMATION: n is a, c, g, or t
<220> FEATURE:
<221> NAME/KEY: misc_feature
<222> LOCATION: (1245)..(1245)
<223> OTHER INFORMATION: n is a, c, g, or t
<220> FEATURE:
<221> NAME/KEY: misc_feature
<222> LOCATION: (1257)..(1257)
<223> OTHER INFORMATION: n is a, c, g, or t
<220> FEATURE:
<221> NAME/KEY: misc_feature
<222> LOCATION: (1260)..(1260)
<223> OTHER INFORMATION: n is a, c, g, or t
```

```
<220> FEATURE:
<221> NAME/KEY: misc_feature
<222> LOCATION: (1266)..(1266)
<223> OTHER INFORMATION: n is a, c, g, or t
<220> FEATURE:
<221> NAME/KEY: misc_feature
<222> LOCATION: (1272)..(1272)
<223> OTHER INFORMATION: n is a, c, g, or t
<220> FEATURE:
<221> NAME/KEY: misc_feature
<222> LOCATION: (1278)..(1278)
<223> OTHER INFORMATION: n is a, c, g, or t
<220> FEATURE:
<221> NAME/KEY: misc_feature
<222> LOCATION: (1281)..(1281)
<223> OTHER INFORMATION: n is a, c, g, or t
<220> FEATURE:
<221> NAME/KEY: misc_feature
<222> LOCATION: (1284)..(1284)
<223> OTHER INFORMATION: n is a, c, g, or t
<220> FEATURE:
<221> NAME/KEY: misc_feature
<222> LOCATION: (1293)..(1293)
<223> OTHER INFORMATION: n is a, c, g, or t
<220> FEATURE:
<221> NAME/KEY: misc_feature
<222> LOCATION: (1296)..(1296)
<223> OTHER INFORMATION: n is a, c, g, or t
<220> FEATURE:
<221> NAME/KEY: misc_feature
<222> LOCATION: (1311)..(1311)
<223> OTHER INFORMATION: n is a, c, g, or t
<220> FEATURE:
<221> NAME/KEY: misc_feature
<222> LOCATION: (1320)..(1320)
<223> OTHER INFORMATION: n is a, c, g, or t
<220> FEATURE:
<221> NAME/KEY: misc_feature
<222> LOCATION: (1323)..(1323)
<223> OTHER INFORMATION: n is a, c, g, or t
<220> FEATURE:
<221> NAME/KEY: misc_feature
<222> LOCATION: (1326)..(1326)
<223> OTHER INFORMATION: n is a, c, g, or t
<220> FEATURE:
<221> NAME/KEY: misc_feature
<222> LOCATION: (1332)..(1332)
<223> OTHER INFORMATION: n is a, c, g, or t
<220> FEATURE:
<221> NAME/KEY: misc_feature
<222> LOCATION: (1335)..(1335)
<223> OTHER INFORMATION: n is a, c, g, or t
<220> FEATURE:
<221> NAME/KEY: misc_feature
<222> LOCATION: (1338)..(1338)
<223> OTHER INFORMATION: n is a, c, g, or t

<400> SEQUENCE: 40
cargtnacny tnaargarws nggnccnggn athytnaarc cnwsncarac nytnwsnytn      60
acntgywsnt tywsnggntt ywsnytnwsn acnwsnggna tgggngtngg ntggathmgn     120
carccnwsng gnaarggnyt ngartggytn gcncayatht ggtgggayga ygayaartay     180
tayaayccnw snytnaarws ncarytnacn athwsnaarg ayacnwsnmg naaycargtn     240
ttyytnaara thacnwsngt ngayacngcn gayacngcna cntaytaytg ygcnmgnmgn     300
gcntaytayt ayggnwsnws ntayccnatg gaytaytggg gncarggnac nwsngtnacn     360
gtnwsnwsng cnaaracnac nccnccnwsn gtntayccny tngcnccngg nwsngcngcn     420
caracnaayw snatggtnac nytnggntgy ytngtnaarg gntayttycc ngarccngtn     480
acngtnacnt ggaaywsngg nwsnytnwsn wsnggngtnc ayacnttycc ngcngtnytn     540
carwsngayy tntayacnyt nwsnwsnwsn gtnacngtnc cnwsnwsnac ntggccnwsn     600
```

-continued

```
garacngtna cntgyaaygt ngcncayccn gcnwsnwsna cnaargtnga yaaraarath      660
gtnccnmgng aytgyggntg yaarccntgy athtgyacng tnccngargt nwsnwsngtn      720
ttyathttyc cnccnaarcc naargaygtn ytnacnatha cnytnacncc naargtnacn      780
tgygtngtng tngayathws naargaygay ccngargtnc arttywsntg gttygtngay      840
gaygtngarg tncayacngc ncaracncar ccnmgngarg arcarttyaa ywsnacntty      900
mgnwsngtnw sngarytncc nathatgcay cargaytggy tnaayggnaa rgarttyaar      960
tgymgngtna aywsngcngc nttyccngcn ccnathgara aracnathws naaracnaar     1020
ggnmgnccna argcnccnca rgtntayacn athccnccnc cnaargarca ratggcnaar     1080
gayaargtnw snytnacntg yatgathacn gayttyttyc cngargayat hacngtngar     1140
tggcartgga ayggncarcc ngcngaraay tayaaraaya cncarccnat hatggayacn     1200
gayggnwsnt ayttygtnta ywsnaarytn aaygtncara arwsnaaytg ggargcnggn     1260
aayacnttya cntgywsngt nytncaygar ggnytncaya aycaycayac ngaraarwsn     1320
ytnwsncayw snccnggn                                                   1338
```

```
<210> SEQ ID NO 41
<211> LENGTH: 654
<212> TYPE: DNA
<213> ORGANISM: Artificial Sequence
<220> FEATURE:
<223> OTHER INFORMATION: nucleotide sequence encoding light chain of
      antibody from hybridoma DG4H4 reverse translated from SEQ ID NO:
      30 with most likely codons

<400> SEQUENCE: 41
```

```
gacatcgtgc tgacccagag ccccaccagc ctggccgtga gcctgggcca gagggccacc       60
ttcagctgca aggccagcca gagcgtggac tacgacggcg acagctacat gaactggtac      120
cagcagaagc ccggccagcc ccccaagctg ctgatctacg ccgccagcaa cctggacagc      180
ggcatccccg ccaggttcag cggcagcggc agcggcaccg acttcaccct gaacatccac      240
cccgtggagg aggaggacgc cgccacctac tactgccagc agagcaacga ggacccctg      300 accttcggcg ccggcaccaa gctggagctg aagagggccg acgccgcccc caccgtgagc      360
atcttccccc ccagcagcga gcagctgacc agcggcggcg ccagcgtggt gtgcttcctg      420
aacaacttct accccaagga catcaacgtg aagtggaaga tcgacggcag cgagaggcag      480
aacggcgtgc tgaacagctg gaccgaccag gacagcaagg acagcaccta cagcatgagc      540
agcaccctga ccctgaccaa ggacgagtac gagaggcaca cagctacac ctgcgaggcc      600 acccacaaga ccagcaccag ccccatcgtg aagagcttca acaggaacga gtgc            654
```

```
<210> SEQ ID NO 42
<211> LENGTH: 654
<212> TYPE: DNA
<213> ORGANISM: Artificial Sequence
<220> FEATURE:
<223> OTHER INFORMATION: nucleotide sequence encoding light chain of
      antibody from hybridoma DG4H4 reverse translated from SEQ ID NO:
      30 with consensus codons
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
```

-continued

```
<222> LOCATION: (15)..(15)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (66)..(66)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (99)..(99)
<223> OTHER INFORMATION: n is a, c, g, or t
<220> FEATURE:
```

-continued

```
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (153)..(153)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
```

-continued

```
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (330)..(330)
```

-continued

```
<223> OTHER INFORMATION: n is a, c, g, or t
<220> FEATURE:
<221> NAME/KEY: misc_feature
<222> LOCATION: (336)..(336)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (351)..(351)
<223> OTHER INFORMATION: n is a, c, g, or t
<220> FEATURE:
<221> NAME/KEY: misc_feature
<222> LOCATION: (354)..(354)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
```

```
<222> LOCATION: (408)..(408)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
```

-continued

<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (630)..(630)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t

<400> SEQUENCE: 42
gayathgtny tnacncarws nccnacnwsn ytngcngtnw snytnggnca rmgngcnacn          60
ttywsntgya argcnwsnca rwsngtngay taygayggng aywsntayat gaaytggtay         120
carcaraarc cnggncarcc nccnaarytn ytnathtayg cngcnwsnaa yytngaywsn         180
ggnathccng cnmgnttyws nggnwsnggn wsnggnacng ayttyacnyt naayathcay         240
ccngtngarg argargaygc ngcnacntay taytgycarc arwsnaayga rgayccnytn         300

```
acnttyggng cnggnacnaa rytngarytn aarmgngcng aygcngcncc nacngtnwsn     360
athttyccnc cnwsnwsnga rcarytnacn wsnggnggng cnwsngtngt ntgyttyytn     420
aayaayttyt ayccnaarga yathaaygtn aartggaara thgayggnws ngarmgncar     480
aayggngtny tnaaywsntg dacngaycar gaywsnaarg aywsnacnta ywsnatgwsn     540
wsnacnytna cnytnacnaa rgaygartay garmgncaya aywsntayac ntgygargcn     600
acncayaara cnwsnacnws nccnathgtn aarwsnttya aymgnaayga rtgy          654
```

```
<210> SEQ ID NO 43
<211> LENGTH: 895
<212> TYPE: PRT
<213> ORGANISM: Homo sapiens

<400> SEQUENCE: 43

Met Arg Met Ser Val Gly Leu Ser Leu Leu Leu Pro Leu Ser Gly Arg
1               5                   10                  15

Thr Phe Leu Leu Leu Leu Ser Val Val Met Ala Gln Ser His Trp Pro
            20                  25                  30

Ser Glu Pro Ser Glu Ala Val Arg Asp Trp Glu Asn Gln Leu Glu Ala
        35                  40                  45

Ser Met His Ser Val Leu Ser Asp Leu His Glu Ala Val Pro Thr Val
    50                  55                  60

Val Gly Ile Pro Asp Gly Thr Ala Val Val Gly Arg Ser Phe Arg Val
65                  70                  75                  80

Thr Ile Pro Thr Asp Leu Ile Ala Ser Ser Gly Asp Ile Ile Lys Val
                85                  90                  95

Ser Ala Ala Gly Lys Glu Ala Leu Pro Ser Trp Leu His Trp Asp Ser
            100                 105                 110

Gln Ser His Thr Leu Glu Gly Leu Pro Leu Asp Thr Asp Lys Gly Val
        115                 120                 125

His Tyr Ile Ser Val Ser Ala Thr Arg Leu Gly Ala Asn Gly Ser His
    130                 135                 140

Ile Pro Gln Thr Ser Ser Val Phe Ser Ile Glu Val Tyr Pro Glu Asp
145                 150                 155                 160

His Ser Glu Leu Gln Ser Val Arg Thr Ala Ser Pro Asp Pro Gly Glu
                165                 170                 175

Val Val Ser Ser Ala Cys Ala Ala Asp Glu Pro Val Thr Val Leu Thr
            180                 185                 190

Val Ile Leu Asp Ala Asp Leu Thr Lys Met Thr Pro Lys Gln Arg Ile
        195                 200                 205

Asp Leu Leu His Arg Met Arg Ser Phe Ser Glu Val Glu Leu His Asn
    210                 215                 220

Met Lys Leu Val Pro Val Val Asn Asn Arg Leu Phe Asp Met Ser Ala
225                 230                 235                 240

Phe Met Ala Gly Pro Gly Asn Ala Lys Lys Val Val Glu Asn Gly Ala
                245                 250                 255

Leu Leu Ser Trp Lys Leu Gly Cys Ser Leu Asn Gln Asn Ser Val Pro
            260                 265                 270

Asp Ile His Gly Val Glu Ala Pro Ala Arg Glu Gly Ala Met Ser Ala
        275                 280                 285

Gln Leu Gly Tyr Pro Val Val Gly Trp His Ile Ala Asn Lys Lys Pro
    290                 295                 300

Pro Leu Pro Lys Arg Val Arg Arg Gln Ile His Ala Thr Pro Thr Pro
```

-continued

```
305                310                315                320

Val Thr Ala Ile Gly Pro Pro Thr Thr Ala Ile Gln Glu Pro Pro Ser
                325                330                335

Arg Ile Val Pro Thr Pro Thr Ser Pro Ala Ile Ala Pro Pro Thr Glu
                340                345                350

Thr Met Ala Pro Pro Val Arg Asp Pro Val Pro Gly Lys Pro Thr Val
                355                360                365

Thr Ile Arg Thr Arg Gly Ala Ile Ile Gln Thr Pro Thr Leu Gly Pro
                370                375                380

Ile Gln Pro Thr Arg Val Ser Glu Ala Gly Thr Thr Val Pro Gly Gln
385                390                395                400

Ile Arg Pro Thr Met Thr Ile Pro Gly Tyr Val Glu Pro Thr Ala Val
                405                410                415

Ala Thr Pro Pro Thr Thr Thr Thr Lys Lys Pro Arg Val Ser Thr Pro
                420                425                430

Lys Pro Ala Thr Pro Ser Thr Asp Ser Thr Thr Thr Thr Arg Arg
                435                440                445

Pro Thr Lys Lys Pro Arg Thr Pro Arg Pro Val Pro Arg Val Thr Thr
                450                455                460

Lys Val Ser Ile Thr Arg Leu Glu Thr Ala Ser Pro Pro Thr Arg Ile
465                470                475                480

Arg Thr Thr Thr Ser Gly Val Pro Arg Gly Gly Glu Pro Asn Gln Arg
                485                490                495

Pro Glu Leu Lys Asn His Ile Asp Arg Val Asp Ala Trp Val Gly Thr
                500                505                510

Tyr Phe Glu Val Lys Ile Pro Ser Asp Thr Phe Tyr Asp His Glu Asp
                515                520                525

Thr Thr Thr Asp Lys Leu Lys Leu Thr Leu Lys Leu Arg Glu Gln Gln
                530                535                540

Leu Val Gly Glu Lys Ser Trp Val Gln Phe Asn Ser Asn Ser Gln Leu
545                550                555                560

Met Tyr Gly Leu Pro Asp Ser Ser His Val Gly Lys His Glu Tyr Phe
                565                570                575

Met His Ala Thr Asp Lys Gly Gly Leu Ser Ala Val Asp Ala Phe Glu
                580                585                590

Ile His Val His Arg Arg Pro Gln Gly Asp Arg Ala Pro Ala Arg Phe
                595                600                605

Lys Ala Lys Phe Val Gly Asp Pro Ala Leu Val Leu Asn Asp Ile His
                610                615                620

Lys Lys Ile Ala Leu Val Lys Lys Leu Ala Phe Ala Phe Gly Asp Arg
625                630                635                640

Asn Cys Ser Thr Ile Thr Leu Gln Asn Ile Thr Arg Gly Ser Ile Val
                645                650                655

Val Glu Trp Thr Asn Asn Thr Leu Pro Leu Glu Pro Cys Pro Lys Glu
                660                665                670

Gln Ile Ala Gly Leu Ser Arg Arg Ile Ala Glu Asp Asp Gly Lys Pro
                675                680                685

Arg Pro Ala Phe Ser Asn Ala Leu Glu Pro Asp Phe Lys Ala Thr Ser
                690                695                700

Ile Thr Val Thr Gly Ser Gly Ser Cys Arg His Leu Gln Phe Ile Pro
705                710                715                720

Val Val Pro Pro Arg Arg Val Pro Ser Glu Ala Pro Pro Thr Glu Val
                725                730                735
```

-continued

```
Pro Asp Arg Asp Pro Glu Lys Ser Ser Glu Asp Asp Val Tyr Leu His
        740                 745                 750

Thr Val Ile Pro Ala Val Val Val Ala Ala Ile Leu Leu Ile Ala Gly
        755                 760                 765

Ile Ile Ala Met Ile Cys Tyr Arg Lys Arg Lys Gly Lys Leu Thr
        770                 775                 780

Leu Glu Asp Gln Ala Thr Phe Ile Lys Lys Gly Val Pro Ile Ile Phe
785                 790                 795                 800

Ala Asp Glu Leu Asp Asp Ser Lys Pro Pro Pro Ser Ser Ser Met Pro
                805                 810                 815

Leu Ile Leu Gln Glu Glu Lys Ala Pro Leu Pro Pro Pro Glu Tyr Pro
                820                 825                 830

Asn Gln Ser Val Pro Glu Thr Thr Pro Leu Asn Gln Asp Thr Met Gly
        835                 840                 845

Glu Tyr Thr Pro Leu Arg Asp Glu Asp Pro Asn Ala Pro Pro Tyr Gln
    850                 855                 860

Pro Pro Pro Pro Phe Thr Ala Pro Met Glu Gly Lys Gly Ser Arg Pro
865                 870                 875                 880

Lys Asn Met Thr Pro Tyr Arg Ser Pro Pro Pro Tyr Val Pro Pro
                885                 890                 895

<210> SEQ ID NO 44
<211> LENGTH: 15
<212> TYPE: PRT
<213> ORGANISM: Artificial Sequence
<220> FEATURE:
<223> OTHER INFORMATION: Exemplary AviTag(TM)

<400> SEQUENCE: 44

Gly Leu Asn Asp Ile Phe Glu Ala Gln Lys Ile Glu Trp His Glu
1               5                   10                  15

<210> SEQ ID NO 45
<211> LENGTH: 26
<212> TYPE: PRT
<213> ORGANISM: Artificial Sequence
<220> FEATURE:
<223> OTHER INFORMATION: Exemplary CBP (calmodulin binding peptide)

<400> SEQUENCE: 45

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 46
<211> LENGTH: 6
<212> TYPE: PRT
<213> ORGANISM: Artificial Sequence
<220> FEATURE:
<223> OTHER INFORMATION: Exemplary polyglutamate tag

<400> SEQUENCE: 46

Glu Glu Glu Glu Glu Glu
1               5

<210> SEQ ID NO 47
<211> LENGTH: 13
<212> TYPE: PRT
<213> ORGANISM: Artificial Sequence
<220> FEATURE:
```

<223> OTHER INFORMATION: Exemplary E tag

<400> SEQUENCE: 47

Gly Ala Pro Val Pro Tyr Pro Asp Pro Leu Glu Pro Arg
1               5                   10

<210> SEQ ID NO 48
<211> LENGTH: 7
<212> TYPE: PRT
<213> ORGANISM: Artificial Sequence
<220> FEATURE:
<223> OTHER INFORMATION: Exemplary FLAG tag

<400> SEQUENCE: 48

Asp Tyr Lys Asp Asp Asp Asp
1               5

<210> SEQ ID NO 49
<211> LENGTH: 8
<212> TYPE: PRT
<213> ORGANISM: Artificial Sequence
<220> FEATURE:
<223> OTHER INFORMATION: Exemplary FLAG tag

<400> SEQUENCE: 49

Asp Tyr Lys Asp Asp Asp Asp Lys
1               5

<210> SEQ ID NO 50
<211> LENGTH: 7
<212> TYPE: PRT
<213> ORGANISM: Artificial Sequence
<220> FEATURE:
<223> OTHER INFORMATION: Exemplary FLAG tag

<400> SEQUENCE: 50

Asp Tyr Lys Asp Asp Asp Lys
1               5

<210> SEQ ID NO 51
<211> LENGTH: 9
<212> TYPE: PRT
<213> ORGANISM: Artificial Sequence
<220> FEATURE:
<223> OTHER INFORMATION: Exemplary HA tag

<400> SEQUENCE: 51

Tyr Pro Tyr Asp Val Pro Asp Tyr Ala
1               5

<210> SEQ ID NO 52
<211> LENGTH: 9
<212> TYPE: PRT
<213> ORGANISM: Artificial Sequence
<220> FEATURE:
<223> OTHER INFORMATION: Exemplary HA tag

<400> SEQUENCE: 52

Tyr Ala Tyr Asp Val Pro Asp Tyr Ala
1               5

<210> SEQ ID NO 53
<211> LENGTH: 9
<212> TYPE: PRT
<213> ORGANISM: Artificial Sequence
<220> FEATURE:
<223> OTHER INFORMATION: Exemplary HA tag

<400> SEQUENCE: 53

Tyr Asp Val Pro Asp Tyr Ala Ser Leu
1               5

<210> SEQ ID NO 54
<211> LENGTH: 10
<212> TYPE: PRT
<213> ORGANISM: Artificial Sequence
<220> FEATURE:
<223> OTHER INFORMATION: Exemplary Myc tag

<400> SEQUENCE: 54

Glu Gln Lys Leu Ile Ser Glu Glu Asp Leu
1               5                   10

<210> SEQ ID NO 55
<211> LENGTH: 6
<212> TYPE: PRT
<213> ORGANISM: Artificial Sequence
<220> FEATURE:
<223> OTHER INFORMATION: Exemplary poly His tag

<400> SEQUENCE: 55

His His His His His His
1               5

<210> SEQ ID NO 56
<211> LENGTH: 15
<212> TYPE: PRT
<213> ORGANISM: Artificial Sequence
<220> FEATURE:
<223> OTHER INFORMATION: Exemplary S tag

<400> SEQUENCE: 56

Lys Glu Thr Ala Ala Ala Lys Phe Glu Arg Gln His Met Asp Ser
1               5                   10                  15

<210> SEQ ID NO 57
<211> LENGTH: 38
<212> TYPE: PRT
<213> ORGANISM: Artificial Sequence
<220> FEATURE:
<223> OTHER INFORMATION: Exemplary SBP (streptavidin binding peptide)

<400> SEQUENCE: 57

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 58
<211> LENGTH: 13
<212> TYPE: PRT
<213> ORGANISM: Artificial Sequence
<220> FEATURE:
<223> OTHER INFORMATION: Exemplary Softag 1

<400> SEQUENCE: 58

Ser Leu Ala Glu Leu Leu Asn Ala Gly Leu Gly Gly Ser
1               5                   10

<210> SEQ ID NO 59

```
<211> LENGTH: 8
<212> TYPE: PRT
<213> ORGANISM: Artificial Sequence
<220> FEATURE:
<223> OTHER INFORMATION: Exemplary Softag 3

<400> SEQUENCE: 59

Thr Gln Asp Pro Ser Arg Val Gly
1               5

<210> SEQ ID NO 60
<211> LENGTH: 8
<212> TYPE: PRT
<213> ORGANISM: Artificial Sequence
<220> FEATURE:
<223> OTHER INFORMATION: Exemplary Strep tag

<400> SEQUENCE: 60

Trp Ser His Pro Gln Phe Glu Lys
1               5

<210> SEQ ID NO 61
<211> LENGTH: 8
<212> TYPE: PRT
<213> ORGANISM: Artificial Sequence
<220> FEATURE:
<223> OTHER INFORMATION: Exemplary Strep tag

<400> SEQUENCE: 61

Trp Arg His Pro Gln Phe Gly Gly
1               5

<210> SEQ ID NO 62
<211> LENGTH: 6
<212> TYPE: PRT
<213> ORGANISM: Artificial Sequence
<220> FEATURE:
<223> OTHER INFORMATION: Exemplary TC tag

<400> SEQUENCE: 62

Cys Cys Pro Gly Cys Cys
1               5

<210> SEQ ID NO 63
<211> LENGTH: 14
<212> TYPE: PRT
<213> ORGANISM: Artificial Sequence
<220> FEATURE:
<223> OTHER INFORMATION: Exemplary V5 tag

<400> SEQUENCE: 63

Gly Lys Pro Ile Pro Asn Pro Leu Leu Gly Leu Asp Ser Thr
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Exemplary VSV tag

<400> SEQUENCE: 64

Tyr Thr Asp Ile Glu Met Asn Arg Leu Gly Lys
1               5                   10

<210> SEQ ID NO 65
<211> LENGTH: 8
```

-continued

```
<212> TYPE: PRT
<213> ORGANISM: Artificial Sequence
<220> FEATURE:
<223> OTHER INFORMATION: Exemplary Xpress tag

<400> SEQUENCE: 65

Asp Leu Tyr Asp Asp Asp Asp Lys
1               5
```